United States Patent
Taremi et al.

(10) Patent No.: US 8,034,907 B2
(45) Date of Patent: Oct. 11, 2011

(54) POLYNUCLEOTIDES ENCODING SOLUBLE, STABLE FORMS OF HUMAN DOUBLE MINUTE 2 POLYPEPTIDES

(75) Inventors: Shahriar Shane Taremi, Cambridge, MA (US); Gaolian Xie, Edison, NJ (US); Thomas Hesson, Cambridge, MA (US); Jose S. Duca, Cranford, NJ (US); Corey Strickland, Martinsville, NJ (US); William T. Windsor, East Brunswick, NJ (US); Vincent S. Madison, Ukiah, CA (US); Rumin Zhang, Edison, NJ (US); Paul Reichert, Montville, NJ (US); Yaolin Wang, Short Hills, NJ (US)

(73) Assignee: Schering Corp., Kenilworth, NJ (US)

( * ) Notice: Subject to any disclaimer, the term of this patent is extended or adjusted under 35 U.S.C. 154(b) by 0 days.

(21) Appl. No.: 12/621,241

(22) Filed: Nov. 18, 2009

(65) Prior Publication Data
US 2010/0136620 A1 Jun. 3, 2010

Related U.S. Application Data

(62) Division of application No. 10/822,254, filed on Apr. 9, 2004, now Pat. No. 7,632,920.

(60) Provisional application No. 60/461,787, filed on Apr. 10, 2003, provisional application No. 60/547,265, filed on Feb. 24, 2004.

(51) Int. Cl.
*C07K 1/14* (2006.01)
*C12P 21/06* (2006.01)
*C12N 1/20* (2006.01)
*C12N 1/00* (2006.01)
*C12N 5/00* (2006.01)
*C07H 21/00* (2006.01)

(52) U.S. Cl. ............. 530/412; 435/69.1; 435/252.3; 435/252.33; 435/254.11; 435/325; 435/320.1; 536/23.1

(58) Field of Classification Search .................. None
See application file for complete search history.

(56) References Cited

U.S. PATENT DOCUMENTS

| 5,420,263 | A | 5/1995 | Burrell et al. |
| 2002/0045192 | A1 | 4/2002 | Kriwacki et al. |
| 2004/0005686 | A1 | 1/2004 | Kurumbail et al. |
| 2004/0197893 | A1 | 10/2004 | Schubert et al. |

OTHER PUBLICATIONS

Cherepanov et al., J. Biochem. 129:61-68, 2001.*
GenBank Accession No. M92424, Jan. 1995, 2 pages.*
Böttger, Angelika, et al., "Molecular Characterization of the hdm2-p53 Interaction," *J. Mol. Biol.* 269:744-756 (1997).
Chéne, Patrick, et al., "A Small Synthetic Peptide, which Inhibits the p53-hdm2 Interaction, Stimulates the p53 Pathway in Tumour Cell Lines," *J. Am. Biol.* 299:245-253 (2000).
Chéne, Patrick, "Inhibiting the p53-MDM2 Interaction: An Important Target for Cancer Therapy," *Nature. Reviews Cancer* 3:102-109 (Feb. 2003).
Kussie, Paul H., et al., "Structure of the MDM2 Oncoprotein Bound to the p53 Tumor Suppressor Transactivation Domain," *Science* 274:948-53 (Nov. 8, 1996).
Webster's online dictionary (Webster.com) definition of "represent", last viewed on Oct. 23, 2007.
Kundrot et al., "Which strategy for a protein crystallization project?", Cell. Mol. Life Sci. 2004, 61:525-536.
Weber, "Overview of Protein Crystallization Methods", Methods in Enzymology, 1997, vol. 276, pp. 13-22.
Cudney, "Protein Crytallization and Dumb Luck", Rigaku Journal, 1999, vol. 16, No. 1, pp. 1-7.
McPherson et al., "Current approaches to macromolecular crystallization", Eur. J. Biochem. 189:1-12, 1990.
Drenth et al., "Principles of X-ray Crystallography", Springer, New York, 1999, pp. 1-21.
Wiencek, "New Strategies for Protein Crystal Growth", Ann Rev Biomed Eng 1:505-534, 1999.
Skarzynski et al., "Industrial perspective on X-ray data collection and analysis", Acta Cryst D62:102-107, 2006.
Kierzek et al., Biophys Chem 91:1-20, 2001.
Buts et al., Acta Crystallogr. D. 61:1149-1159, 2005.
"Encyclopedia of Molecular Biology", Creighton, T., John Wiley and Sons, Inc. New York, 1999, pp. 586 and 2725.
"Introduction to Protein Structure", Branden and Tooze, Garland Publishing Inc., New York, 1991, p. 247.
Witkowski et al. (1999) Biochemistry 38:11643-11650.
"Introduction to Protein Structure Second Edition", Branden and Tooze, Garland Publishing Inc., New York, pp. 374-375, 1999.
Grasberger et al., (2005) J Med Chem 48:909-912 and S1-S7.

* cited by examiner

*Primary Examiner* — David J Steadman

(57) ABSTRACT

The present invention discloses modified Hdm2 proteins that are soluble. In addition, the present invention discloses nucleic acids that encode the modified Hdm2 proteins of the present invention. The invention also provides crystals of modified Hdm2 proteins that are suitable for X-ray crystallization analysis. The present invention also discloses methods of using the modified Hdm2 proteins and crystals thereof to identify, select and/or design compounds that may be used as anticancer agents. The present invention further discloses compounds that bind to modified Hdm2 proteins in protein-ligand complexes.

7 Claims, No Drawings

POLYNUCLEOTIDES ENCODING SOLUBLE, STABLE FORMS OF HUMAN DOUBLE MINUTE 2 POLYPEPTIDES

The present application is a divisional of U.S. application Ser. No. 10/822,254, filed Apr. 9, 2004, (now U.S. Pat. No. 7,632,920) which claims the benefit of U.S. Provisional Applications 60/461,787, filed Apr. 10, 2003, and 60/547,265, filed Feb. 24, 2004. These applications are hereby incorporated by reference in their entirety.

FIELD OF THE INVENTION

The present invention relates to a soluble and stable form of human Double Minute 2 protein, Hdm2. The present invention further pertains to nucleic acids encoding these proteins. The present invention also relates to a process of obtaining specific samples of Hdm2 that are amenable to forming homogeneous crystals for X-ray crystallization analysis and the crystals formed thereby. The present invention also pertains to methods of using the X-ray diffractable crystals in structure-based drug design to identify compounds that can modulate the activity of the protein.

BACKGROUND OF THE INVENTION

The most commonly inactivated tumor suppressor gene in human cancer encodes the p53 protein, a transcription factor that is intimately involved in maintaining the integrity of the genome in a cell [Hall and Peters, *Adv. Cancer Res.*, 68:67-108 (1996); Hainaut et al., *Nucleic Acid Res.*, 25:151-157 (1997); Sherr, *Cancer Res.*, 60:3689-95 (2000)]. In response to oncogenic stress signals, the cell triggers the p53 transcription factor to initiate either apoptosis or cell cycle arrest. Apoptosis facilitates the elimination of damaged cells from the organism, while cell cycle arrest enables damaged cells to repair genetic damage [reviewed in Ko et al., *Genes & Devel.* 10:1054-1072 (1996); Levine, *Cell* 88:323-331 (1997)]. The loss of the safeguard functions of p53 predisposes damaged cells to progress to a cancerous state. Inactivating p53 in mice consistently leads to an unusually high rate of tumors [Donehower et al., *Nature*, 356:215-221 (1992)].

The p53 transcription factor promotes the expression of a number of cell cycle regulatory genes, including the gene encoding the Mouse Double Minute (Mdm2) protein [see, Chene, *Nature Reviews Cancer* 3:102-109 (2003)]. The Mdm2 protein (designated Hdm2 in humans and Mdm2 in mice) acts to down-regulate p53 activity in an auto-regulatory manner [Wu et al., *Genes Dev.*, 7:1126-1132 (1993); Barak et al., *EMBO J*, 12:461-468 (1993)]. In the absence of oncogenic stress signals, i.e., under normal cellular conditions, the Mdm2 protein serves to maintain p53 activity at low levels [Wu et al., *Genes Dev.*, 7:1126-1132 (1993); Barak et al., *EMBO J*, 12:461-468 (1993)].

Interestingly, whereas Mdm2 negative (Mdm2$^{-/-}$) mice are not viable [Jones et al., *Nature*, 378:206-208 (1995); Montes de Oca Luna et al., *Nature*, 378:203-206 (1995)], additional inactivation of the p53 gene rescues Mdm2$^{-/-}$ mice [Jones et al., *Nature*, 378:206-208 (1995); Montes de Oca Luna et al., *Nature*, 378:203-206 (1995)]. These results indicate that the misregulation of the p53 transcription factor in the Mdm2 negative mice is the root cause of the observed lethality of the Mdm2$^{-/-}$ genotype, and that the regulation of p53 function relies on an appropriate balance between the two components of this p53-Mdm2 auto-regulatory system. Indeed, this balance appears to be essential for cell survival.

There are at least three ways that Mdm2 acts to downregulate p53 activity. First, Mdm2 can bind to the N-terminal transcriptional activation domain of p53 to block expression of p53-responsive genes [Kussie et al., *Science*, 274:948-953 (1996); Oliner et al., *Nature*, 362:857-860 (1993); Momand et al., *Cell*, 69:1237-1245 (1992)]. Second, Mdm2 shuttles p53 from the nucleus to the cytoplasm to facilitate the proteolytic degradation of p53 [Roth et al., *EMBO J*, 17:554-564 (1998); Freedman et al., *Mol Cell Biol*, 18:7288-7293 (1998); Tao and Levine, *Proc. Natl. Acad. Sci.* 96:3077-3080 (1999)]. Finally, Mdm2 possesses an intrinsic E3 ligase activity for conjugating ubiquitin to p53 within the ubiquitin-dependent 26S proteosome pathway [Honda et al., *FEBS Lett*, 420:25-27 (1997); Yasuda, *Oncogene* 19:1473-1476 (2000)]. Thus, Mdm2 impedes the ability of the p53 transcription factor to promote the expression of its target genes through binding p53 in the nucleus.

Attenuating the p53-Mdm2 auto-regulatory system can have a critical effect on cell homeostasis. Consistently, a correlation between the overexpression of Mdm2 and tumor formation has been reported [Chene, *Nature* 3:102-109 (2003)]. Since Mdm2 acts as a post-translational regulatory effector of the p53 transcription factor, compounds that hinder the ability of Hdm2/Mdm2, to interact with p53 would be anticipated to cause an immediate increase in p53 activity, and thereby rapidly promote either cell cycle arrest or apoptosis in damaged cells. Not surprisingly then, there is currently a substantial effort being made to identify new anticancer agents that hinder the ability of Hdm2 to interact with p53 [Chene, *Nature* 3:102-109 (2003)]. However, to date, no suitable anticancer agent has been found.

Structure-based drug design is one way to optimize the success of identifying useful antagonists of Hdm2, but use of this powerful methodology requires the three-dimensional structure of the target protein. So far, little information has been provided regarding the three-dimensional structure of Hdm2. Indeed, the only structures of Hdm2 currently available are those of Hdm2 and *Xenopus* Mdm2 (XMdm2), complexed with a p53 peptide, but neither crystalline form is suitable for structure-based drug design [Kussie, et al. *Science*, 274(5289): 948-953 (1996)]. Moreover, most of the protein-protein contacts in these crystal lattices are formed through the interaction of the exposed residues in the bound p53 peptide (D21, K24, and L25), making the p53 peptide difficult to displace, which makes it inaccessible to potential inhibitors.

In direct contrast, a successful structure-based drug design program focusing on Hdm2 requires a form of the Hdm2 protein that is amenable to crystallization in the absence of any particular binding partner. Further, the crystal form of the p53-binding pocket of the Hdm2 protein should be accessible to potential inhibitors used for testing binding or for co-structural determination. However, up until now, the solubility and stability of the free Hdm2 protein has been significantly less than that of the Hdm2-p53 peptide complex.

Thus, there is a need to obtain nucleic acids that encode an Hdm2 protein that is soluble and stable at high protein concentrations even when the protein is free of p53 or fragments thereof. In addition, there is a need to design purification procedures that lead to the preparation of an isolated active Hdm2 protein that is soluble and stable when independent of p53 or fragments thereof. In addition, there is a need to obtain reproducible crystals of Hdm2 that are of sufficient quality for X-ray crystallization analyses and structural determinations. There is also a need to provide methods for identifying inhibitors of Hdm2 through structure-based drug design and for combining potential inhibitors with the crystals of Hdm2 and analyzing their binding. Further, there is a need to obtain Hdm2 protein samples that, when combined with potential inhibitors, are amenable to forming homogenous crystals.

SUMMARY OF THE INVENTION

The present invention provides modified Hdm2 proteins that are amenable to crystallization and are soluble in *E. coli* extracts. The present invention further discloses a set of amino acid substitutions of the Hdm2 protein that improve its solubility and/or stability without compromising its ability to bind p53. It is a further object of the present invention to provide a modified Hdm2 protein having an amino acid substitution at one or more of the seven sites defined in Table 1. In one embodiment, the modified Hdm2 protein comprises the amino acid of SEQ ID NO: 4, wherein one or more of the seven specific amino acid residues denoted as $X_1$-$X_7$ of SEQ ID NO: 4 differs from that of wild-type Hdm2(17-125) (SEQ ID NO: 2) or said amino acid sequence comprising one or more conservative amino acid substitutions at sites other than that of $X_1$-$X_7$ of SEQ ID NO: 4. In other embodiments, the modified Hdm2 protein comprises an amino acid sequence selected from the group consisting of SEQ ID NOS: 6, 8 10 and 12; or said amino acid sequence comprising one or more conservative amino acid substitutions at sites other than that of $X_1$-$X_7$ of SEQ ID NO: 4.

The present invention further provides isolated and/or recombinant nucleic acids that encode the modified Hdm2 proteins of the present invention, as well as specific peptide fragments and fusion proteins thereof. In one embodiment, the nucleic acid encodes a modified Hdm2 protein comprising the amino acid of SEQ ID NO: 4, wherein one or more of the seven specific amino acid residues denoted as $X_1$-$X_7$ of SEQ ID NO: 4 differs from that of wild-type Hdm2(17-125) (SEQ ID NO: 2) or said amino acid sequence comprising one or more conservative amino acid substitutions at sites other than that of $X_1$-$X_7$ of SEQ ID NO: 4. In other embodiments, the nucleic acid encodes a modified Hdm2 protein comprising an amino acid sequence selected from the group consisting of SEQ ID NOS: 6, 8 10 and 12; or said amino acid sequence comprising one or more conservative amino acid substitutions at sites other than that of $X_1$-$X_7$ of SEQ ID NO: 4. In certain embodiments, the nucleic acid may comprise a nucleotide sequence selected from the group consisting of SEQ ID NOS: 5, 7, 9 and 11. The present invention further provides expression vectors that can comprise any of the nucleic acids of the present invention and a transcriptional control sequence. Preferably the nucleic acids of the present invention are operatively linked to a transcriptional control sequence in expression vectors. Host cells comprising the expression vectors are also part of the present invention. In one particular embodiment, the host cell is an *E. coli* cell.

In addition, the present invention provides methods for producing the above-mentioned modified Hdm2 proteins. One such embodiment comprises culturing a host cell of the present invention that expresses a nucleic acid encoding a modified Hdm2 protein of the present invention, thereby producing the modified Hdm2 protein. Methods for purifying and/or obtaining the resulting recombinant modified Hdm2 proteins are also included in the present invention, as are the purified recombinant modified Hdm2 proteins.

The present invention further provides compounds that bind to Hdm2. In one such embodiment the compound is an acetylated tripeptide. In a particular embodiment of this type the compound is Ac-$^{6Cl}$WAC$_{3c}$E. In another embodiment the compound is Ac-$^{6Br}$WAC$_{3c}$E.

The present invention further provides protein-ligand complexes between the modified Hdm2 proteins of the present invention and their ligands. Preferred ligands in the complex are Ac-$^{6Cl}$WAC$_{3c}$E and Ac-$^{6Br}$WAC$_{3c}$E.

Crystals comprising a modified Hdm2 protein, and/or one of the protein-ligand complexes of the present invention, also are part of the present invention. Preferably, such crystals effectively diffract X-rays for the determination of the atomic coordinates of the protein and/or of the protein-ligand complex to a resolution of greater than 5.0 Å (e.g., at least 3.0 Å, at least 2.5 Å, at least 2.0 Å, or at least 1.5 Å).

The invention provides a crystal comprising a polypeptide selected from (a) a modified Hdm2 protein, characterized by structural coordinates comprising a root mean square deviation of conserved residue backbone atoms of less than about 1.5 Å (e.g., less than about 1.0 Å, less than about 0.5 Å, or less than about 0.1 Å) when superimposed on backbone atoms described by structural coordinates of Table 3 or (b) a modified Hdm2 protein characterized by structural coordinates comprising a root mean square deviation of conserved residue backbone atoms of less than about 1.5 Å (e.g., less than about 1.0 Å, less than about 0.5 Å, or less than about 0.1 Å) when superimposed on backbone atoms described by structural coordinates of Table 4. In certain embodiments, the crystal may be complexed with a compound that binds to modified Hdm2 (e.g., SCH549128, Ac-$^{6Cl}$WAC$_{3c}$E or Ac-$^{6Br}$WAC$_{3c}$E)

The invention also provides the three-dimensional structure of the modified Hdm2 protein. In one embodiment, the three-dimensional structure is characterized by structural coordinates comprising a root mean square deviation of conserved residue backbone atoms of less than about 1.5 Å (e.g., less than about 1.0 Å, less than about 0.5 Å, or less than about 0.1 Å) when superimposed on backbone atoms described by structural coordinates of Table 3 or 4. The present invention further provides methods of using this three-dimensional structural information in drug discovery and/or to solve corresponding structures of Hdm2 homologues, other crystalline forms of Hdm2 mutants, and co-complexes of Hdm2 and its ligands.

In another aspect of the present invention, methods are provided for obtaining a crystal comprising a modified Hdm2 protein. In one embodiment, the crystal is obtained by vapor diffusion.

In another aspect, the present invention provides a crystalline form of Hdm2 protein that is amenable to ligand soaking experiments, which enables X-ray crystallographic structural determinations to be performed on multiple Hdm2-ligand complexes in rapid succession.

The present invention further provides methods of obtaining a crystal comprising a protein-ligand complex between a ligand and a polypeptide comprising a modified Hdm2 protein. The present invention further provides methods for exchanging ligands within a crystal.

In yet another aspect, the present invention provides a method for designing, selecting and/or optimizing a compound and then evaluating it for use as an inhibitor of Hdm2. One such embodiment comprises obtaining a set of atomic coordinates that define the three-dimensional structure of the modified Hdm2 protein from a crystal of the present invention. In a related embodiment, a set of atomic coordinates that define the three-dimensional structure of the protein-ligand binding complex from a crystal of the present invention is obtained. In either case, a potential agent is then designed, selected or optimized by performing structure-based drug design with the atomic coordinates obtained. Preferably, the design or selection is performed in conjunction with computer modeling.

In another aspect, the invention provides a method for evaluating the ability of a potential inhibitor to associate with Hdm2 comprising employing computational means to perform a fitting operation between the potential inhibitor and the structure coordinates of Hdm2 and quantitating the association between the potential inhibitor and Hdm2.

A compound that is predicted to inhibit Hdm2 can be synthesized, if necessary, and subsequently contacted with Hdm2 or an active fragment thereof. The activity of the compound is then determined by an assay that measures one or more of Hdm2's activities, as described above. A compound that is predicted to inhibit Hdm2 is identified as an inhibitor of Hdm2 when there is a decrease in the activity of Hdm2 in the presence of the agent relative to in its absence.

In a related aspect of the present invention, a computer is provided that comprises a three-dimensional representation of a modified Hdm2 protein in computer memory. One such computer comprises a machine-readable data storage medium comprising a data storage material encoded with machine-readable data, comprising the atomic coordinates of Table 3 or 4. In another embodiment, the computer comprises a machine-readable data storage medium comprising a data storage material encoded with machine-readable data, comprising the atomic coordinates of Table 3 or 4. In yet another embodiment, the computer comprises a machine-readable data storage medium comprising a data storage material encoded with machine-readable data, comprising the atomic coordinates of Table 3 or 4. Preferably, the computer further comprises a working memory for storing instructions for processing the machine-readable data, a central-processing unit coupled to the working memory and to the machine-readable data storage medium for processing the machine readable data into a three-dimensional representation of the modified Hdm2 protein and/or Hdm2 protein-ligand complex. More preferably, the computer includes a display coupled to the central-processing unit for displaying the three-dimensional representation.

DETAILED DESCRIPTION OF THE INVENTION

The present invention provides stable modified Hdm2 proteins produced by introducing an amino acid substitution into one or more of a unique set of amino acid residues of Hdm2. The modified Hdm2 proteins of the present invention have an improved solubility and form novel crystals that heretofore were unattainable with the wild-type Hdm2 protein. The present invention further provides methods for generating and purifying these modified Hdm2 proteins. The modified Hdm2 proteins of the present invention may be used for the structural determination of Hdm2 by X-ray crystallography and/or NMR.

Crystals of the modified Hdm2 protein and their resulting structures can be used to design high affinity inhibitors of Hdm2 that may be used in the treatment of cancer. Such drugs may be particularly useful to treat soft-tissue tumors, osteosarcomas and oesophageal carcinomas.

Structure-based drug design is the most efficient method for such drug development. In one common paradigm, a three dimensional structure is determined for a protein, e.g., the modified Hdm2, and/or a corresponding protein-ligand complex. Potential antagonists (e.g., inhibitors and/or potential drugs) of the protein are then identified and/or designed with the aid of computer modeling [Bugg et al., *Scientific American*, Dec.: 92-98 (1993); West et al., *TIPS*, 16:67-74 (1995); Dunbrack et al., *Folding & Design*, 2:27-42 (1997)]. The drug candidates are then selected and tested. The most promising drug candidates are identified and then combined with the protein in a crystalline protein-ligand complex. The three-dimensional structure of the protein-ligand complex is then determined, and new potential antagonists of the protein are identified and/or designed with the aid of computer modeling. This process can then be continued in successive iterations until a lead drug candidate is identified.

Heretofore, the ability to perform structure based drug design with Hdm2 was severely hampered due to the lack of a crystalline form of the Hdm2 that is conducive for such studies. The expression and purification of a modified Hdm2 protein that when placed in a protein-ligand complex can form a monodisperse preparation, as disclosed herein, is therefore critical for the initiation of a structure based drug design program.

In addition, the present invention provides two specific ligands for Hdm2, the acetylated tripeptides, Ac-$^{6Cl}$WAC$_{3c}$E and Ac-$^{6Br}$WAC$_{3c}$E. Their precise chemical structures are provided below. These tripeptides can be used to bind the modified Hdm2 proteins of the present invention to form a protein-ligand complex that is then crystallized. Such X-ray diffractable crystals can be used for structure based drug design to identify anti-tumor drugs.

Patches of hydrophobic amino acid residues on the surface of the Hdm2 protein were initially determined to be a critical factor leading to the relative insolubility of the wild-type Hdm2 protein. Interrupting these hydrophobic patches by replacing selected surface hydrophobic amino acid residues with hydrophilic amino acid alternatives were found to increase the solubility of the ensuing modified Hdm2 protein, as well as create new crystal contact sites.

The present invention therefore provides several approaches for identifying appropriate hydrophobic amino acid residues to be replaced by more hydrophilic alternatives. One such approach entails employing the Clustalw program to align the amino acid sequences of Hdm2 and Hdm4 analogs from a number of species to identify natural amino acid variations. In one particular alignment, protocol Hdm2 or Hdm4 sequences from the following species were used: *Brachydanio rerio* (Zebrafish), *Canis familiaris* (Dog), *Equus caballus* (Horse), *Homo sapiens* (Human), *Mesocricetus auratus* (Golden Hamster), *Mus musculus* (Mouse), *Xenopus laevis* (African Clawed Frog) and *Gallus gallus* (Chicken). Seven Hdm2 surface amino acid residues in the hydrophobic patches of Hdm2 were identified and the preferred alternative amino acids at those sites noted, see Table 1 below. In a related approach, the seven amino acid substitutions were selected to specifically increase Hdm2 solubility, see modified Hdm2 (HK$_5$) having the amino acid sequence of SEQ ID NO: 12.

In still another approach, the amino acid sequences of Hdm2 and XMdm2 were compared to identify the positions of surface, solvent exposed, hydrophobic amino acid residues of the human protein that were occupied by more hydrophilic residues in the corresponding *Xenopus laevis* amino acid sequence. From this protein surface analysis, four potential amino acid substitutions were chosen: Human: *Xenopus laevis*: F55Y, Y76H, Y104S, V109S.

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization*

[B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

As used herein the following terms shall have the definitions set out below:

As used herein the term "polypeptide" is used interchangeably with the term "protein" and is further meant to encompass peptides. Therefore, as used herein, a polypeptide is a polymer of two or more amino acids joined together by peptide linkages. Preferably, a polypeptide is a polymer comprising twenty or more amino acid residues joined together by peptide linkages, whereas a peptide comprises five to twenty amino acid residues joined together by peptide linkages.

As used herein a polypeptide "consisting essentially of" or that "consists essentially of" a specified amino acid sequence is a polypeptide that (i) retains an important characteristic of the polypeptide comprising that amino acid sequence, e.g., the ability to bind p53 and/or act as a ligase for conjugating ubiquitin to p53, and (ii) further comprises the identical amino acid sequence, except it consists of plus or minus 10% (or a lower percentage), and preferably plus or minus 5% (or a lower percentage) of the amino acid residues. In a particular embodiment, additional amino acid residues included as part of the polypeptide are part of a linked Tag, such as a C-terminal His$_6$ Tag.

The term "generic Mdm2" is used herein to refer to the double minute 2 polypeptide from any species. When used by itself, Mdm2 refers to mouse Mdm2. When used with another species name appended to it, it refers to the Mdm2 ortholog from the named species, e.g., *Xenopus* Mdm2 refers to the Mdm2 ortholog from *Xenopus*. "Mdm2" also encompass modified forms thereof.

As used herein the terms "human Mdm2" and "Hdm2" are used interchangeably to denote the human ortholog of Mdm2. "Hdm2" also encompass modified forms thereof. Hdm2 has the GenBank accession number of M92424. Mouse Mdm2 has the GenBank accession number of X58876 [see also, published U.S. patent application 2002/0045192, published Apr. 18, 2002, the contents of which are hereby incorporated by reference in their entirety.] The amino acid sequences provided herein correspond to amino acid residues 17-125 of the full-length Hdm2 protein and retain their numerical designation from that full-length sequence. Therefore, the first amino acid residue of the wild-type Hdm2(17-125) sequence, SEQ ID NO: 2, corresponds to amino acid 17 of the full-length Hdm2 protein.

As used herein a "modified Hdm2" is identical to the wild-type Hdm2(17-125) except it has at least one amino acid substitution, i.e., it has one or more amino acid substitutions. Furthermore, a modified Hmd2 of the present invention comprises an amino acid substitution at one or more of the seven positions listed in Table 1 and denoted in SEQ ID NO: 4. Preferably, that amino acid substitution is one that is specifically defined in Table 1 (and denoted in SEQ ID NO: 4). It is also preferable that a modified Hdm2 protein of the present invention comprises 109 amino acid residues and that the positions of these 109 residues correspond to amino acid residues 17-125 of the full-length wild-type Hdm2 protein.

As used herein, a "conservative amino acid substitution" is the substitution of a functionally equivalent amino acid for an amino acid within the sequence of Hdm2. The conservative amino acid substitution can be at any position in the Hdm2 sequence except for the seven positions identified in Table 1, for which the alternatives are specifically defined. In general, a functionally equivalent amino acid is one having a similar polarity and/or molecular properties for the amino acid within the sequence. Specifically, an amino acid substitute may be selected from other members of the class to which the amino acid belongs. The class of nonpolar amino acids includes alanine, leucine, isoleucine, valine, proline, phenylalanine, tryptophan and methionine. The class of polar neutral amino acids includes glycine, serine, threonine, cysteine, tyrosine, asparagine, and glutamine. The class of positively charged (basic) amino acids includes arginine, and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained; and (e) Ile for Leu or for Val or vice versa as roughly equivalent hydrophobic amino acids.

As used herein the term "specific peptide fragment" is a peptide that comprises at least six amino acid residues, and preferably at least twelve amino acid residues of a modified Hdm2 protein that differs from the corresponding fragment of the wild-type Hdm2 by at least one amino acid residue. Furthermore, the different amino acid residue (or different residues) is located at a position that corresponds to one (or more) of the seven variable sites denoted in SEQ ID NO: 4 and listed Table 1 below.

As used herein the term "chimeric" protein is meant to include fusion proteins. "Chimeric" proteins of the present invention comprise at least a portion of a non-Hdm2 protein or peptide joined via a peptide bond to at least a portion of an Hdm2 protein, preferably a modified Hdm2. Chimeric proteins can have additional structural, regulatory, and/or catalytic properties. As used herein a chimeric protein can contain multiple additions to at least a portion of a modified Hdm2 protein, e.g., it can comprise both a His$_6$Tag and a signal sequence. In a particular embodiment the chimeric protein functions as a means of detecting and/or isolating the polypeptide or fragment thereof after a recombinant nucleic acid encoding the modified Hdm2 protein or fragment thereof is expressed. Non-Hdm2 amino acid sequences are preferably either amino- or carboxy-terminal to the modified Hdm2 sequence.

As used herein, DNA and protein sequence percent identity can be determined using C, MacVector 6.0.1, Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein a "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is double stranded both the "sense" strand and the complementary "antisense" strand are intended to be included. Thus a nucleic acid that is hybridizable to SEQ ID NO: 1, for example, can be either hybridizable to the "sense" strand of SEQ ID NO: 1, which is particularly listed in the SEQUENCE LISTING, or to the "antisense" strand which can be readily determined from that SEQUENCE LISTING.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which can then be trans-RNA spliced and translated into the protein encoded by the coding sequence.

A nucleic acid sequence is "operatively linked" to an expression control sequence when the expression control sequence controls or regulates the transcription and translation of that nucleic acid sequence. The term operatively linked includes having an appropriate start signal.

A "heterologous nucleotide sequence" as used herein is a nucleotide sequence that is added by recombinant methods to a nucleotide sequence encoding a modified Hdm2 of the present invention or encoding a fragment thereof, to form a nucleic acid that is not naturally formed in nature. Such nucleic acids can encode chimeric proteins. In addition, as used herein, a heterologous nucleotide sequence need not be a single contiguous nucleotide sequence, but can include multiple non-contiguous nucleotide sequences that have been combined with a nucleotide sequence encoding a modified Hdm2 protein of the present invention, or a portion thereof. A heterologous nucleotide sequence can comprise non-coding sequences including restriction sites, regulatory sites, promoters and the like. In still another embodiment the heterologous nucleotide can function as a means of detecting a nucleotide sequence of the present invention. The present invention provides heterologous nucleotide sequences that, when combined with nucleotide sequences encoding a modified Hdm2 protein or a fragment thereof, are necessary and sufficient to encode all of the chimeric proteins of the present invention.

The phrase "binding to" in regard to a ligand binding to a polypeptide is used herein to include any or all such specific interactions that lead to a protein-ligand binding complex. This can include processes such as covalent, ionic (electrostatic and/or charged), hydrophobic and hydrogen bonding, but does not include non-specific associations such solvent preferences.

As used herein a "ligand" of a Mdm2 protein, e.g., a modified Hdm2 protein, is a compound that binds to the polypeptide in a protein-ligand binding complex. In a specific embodiment of the present invention the ligand inhibits the ability of the Mdm2 protein to bind p53 when the ligand is bound to the Mdm2 protein in a protein-ligand binding complex. In another embodiment, the ligand inhibits the ability of Mdm2 to act as an E3 ligase for conjugating ubiquitin to p53 when the ligand is bound to the Mdm2 protein in a protein-ligand binding complex. Such ligands may also be termed an "inhibitor".

As used herein, a "protein-ligand binding complex" or polypeptide-compound complex" is a specific association between a polypeptide and the compound that binds to it. In a preferred embodiment of the present invention, the ligand or compound is an inhibitor of the polypeptide. In a particular embodiment of this type, the binding of the inhibitor to the polypeptide occurs at the active site of the polypeptide.

As used herein "incubating a ligand with a crystal" is used interchangeably with "soaking a crystal with a ligand". Incubating a ligand with a crystal is the contacting of a ligand with a crystal of a polypeptide under the appropriate conditions and for a sufficient time period (e.g., hours to several days) for the ligand to bind to the crystalline polypeptide and form a crystalline protein-ligand complex. Such incubating can further include contacting an excess of a substitute ligand with a crystal of a protein-ligand complex under the appropriate conditions and for a sufficient time period (e.g., hours to several days) for the substitute ligand to replace the initial ligand and form the new crystalline protein-ligand complex.

As used herein the terms "displacing", "replacing", and "exchanging" are used interchangeably in regard to the substitution of one ligand in a protein-ligand complex for another.

As used herein an "excess of a substitute ligand" is an amount of that ligand that is sufficient to replace 80% or more, and preferably 90% or more, of the initial ligand in a protein-ligand complex. In a particular embodiment of this type, the concentration of the substitute ligand is about ten-fold higher than the concentration of the protein-ligand complex. In a preferred embodiment, the concentration of the substitute ligand is about one hundred-fold higher than the concentration of the protein-ligand complex.

As used herein the term "X-ray diffractable crystal" is a crystal of a compound, e.g., a protein that yields a discernable diffraction pattern when subjected to 0.5 to 2.5 Å incident X-ray radiation.

As used herein an "X-ray quality crystal" is an X-ray diffractable crystal that can yield meaningful structural data of its crystalline composition when subjected to X-ray crystallographic analysis.

As used herein, and unless otherwise specified, the terms "agent", "potential drug", "compound", or "test compound" are used interchangeably, and refer to chemicals that have or potentially have a use as a modulator of the activity of Mdm2.

Preferably the modulator is an inhibitor of the binding complex formed between p53 and Mdm2. Preferably such agents include drugs for the treatment or prevention of a disease and/or condition involving the p53 transcription factor, e.g., cancer. Therefore, such agents may be used, as described herein, in drug assays and drug screens and the like.

As used herein a "small organic molecule" is an organic compound [or organic compound complexed with an inorganic compound (e.g., metal)] that has a molecular weight of less than 3 Kd.

As used herein the terms "approximately" and "about" are used to signify that a value is within twenty percent of the indicated value i.e., an amino acid sequence containing "approximately" 110 amino acid residues can contain between 88 and 132 amino acid residues.

As used herein the phrases "structure based rational drug design", "structure based drug design" and "structure assisted drug design" are used interchangeably. These phrases are meant to convey a particular method of identifying and/or designing a ligand (preferably an inhibitor) for a specific target protein that includes the use of the three-dimensional structure of that protein and/or its corresponding protein-ligand complex.

Nucleic Acids Encoding Mdm2 Proteins

The nucleic acids can further comprise heterologous nucleotide sequences. In one embodiment, the nucleic acid encodes a modified Hdm2 protein comprising the amino acid of SEQ ID NO: 4, wherein one or more of the seven specific amino acid residues denoted as $X_1$-$X_7$ of SEQ ID NO: 4 differs from that of wild-type Hdm2(17-125) (SEQ ID NO: 2). In a particular embodiment of this type the nucleic acid comprises the nucleotide sequence of SEQ ID NO: 3, wherein at least one nucleotide of one of the codons encoding one or more of the seven specific amino acid residues denoted as $X_1$-$X_7$ of SEQ ID NO: 4 differs from the nucleic acid sequence of wild-type Hdm2(17-125) (SEQ ID NO: 1) and wherein said codon encodes a different amino acid from that of wild-type Hdm2(17-125) (SEQ ID NO: 2).

In one embodiment, the nucleic acid encodes a modified Hdm2 protein comprising the amino acid sequence of SEQ ID NO: 6. In a particular embodiment of this type, the nucleic acid comprises the nucleotide sequence of SEQ ID NO: 5. In another embodiment, the nucleic acid encodes a modified Hdm2 protein comprising the amino acid sequence of SEQ ID NO: 8. In a particular embodiment of this type, the nucleic acid comprises the nucleotide sequence of SEQ ID NO: 7. In still another embodiment, the nucleic acid encodes a modified Hdm2 protein comprising the amino acid sequence of SEQ ID NO: 10. In a particular embodiment of this type, the nucleic acid comprises the nucleotide sequence of SEQ ID NO: 9. In yet another embodiment, the nucleic acid encodes a modified Hdm2 protein comprising the amino acid sequence of SEQ ID NO: 12. In a particular embodiment of this type, the nucleic acid comprises the nucleotide sequence of SEQ ID NO: 11. Nucleic acids that consist of the nucleotide sequences that encode the modified Hdm2 proteins of the present invention or that consist of nucleotide sequences that encode specific peptide fragments of those proteins are also provided. The present invention also includes those nucleic acids that encode a modified Hdm2 comprising one or more conservative amino acid substitutions. In certain embodiments, there may be 1-11 conservative amino acid substitutions, preferably 1, 2 or 3 conservative amino acid substitutions. In a related embodiment, the present invention provides nucleic acids that further comprise a heterologous nucleotide sequence.

Obtaining and/or constructing a cDNA that encodes a Mdm2 protein, including Hdm2 proteins and the modified Hdm2 proteins of the present invention, facilitates the production of the large quantities of protein required to perform standard enzyme assays and/or X-ray crystallographic analysis.

The present invention provides specific nucleic acid constructs that allow for the expression and isolation of large quantities of stable and active modified Hmd2 proteins. These nucleic acids can further contain heterologous nucleotide sequences. To express a recombinant protein of the present invention in a host cell, an expression vector can be constructed comprising the corresponding cDNA. The present invention therefore, provides expression vectors containing nucleic acids encoding the modified Hmd2 proteins of the present invention. Due to the degeneracy of nucleotide coding sequences, other DNA sequences that encode the same or substantially the same amino acid sequence as a nucleic acid encoding a modified Hmd2 protein of the present invention may be used in the practice of the present invention. These include, but are not limited to, allelic genes, homologous genes from other species, which are altered by the substitution of different codons that encode the same amino acid residue within the sequence, thus producing a silent change. Host cells comprising the expression vectors of the present invention are also provided. One particular host cell, an *E. coli* cell, is specifically exemplified below.

General methods for the cloning of cDNAs and expression of their corresponding recombinant proteins have been described [see Sambrook and Russell, *Molecular Cloning, A Laboratory Manual*, 3$^{rd}$ edition, Cold Spring Harbor Laboratory Press, Cold Spring Harbor L.I. (2000)]. The particular methodology used herein is described in Example 1 below. Preferably, all of the nucleic acid constructs of the present invention are sequence confirmed.

Any technique for mutagenesis known in the art can be used to convert the native (wild-type) Hdm2 to a modified Hdm2 of the present invention, including but not limited to, in vitro site-directed mutagenesis [Hutchinson et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986)]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61-70 (1989)].

Preferably mutagenesis (i.e., modification) of an Hdm2 transcript is performed in a two step process [Wang and Malcolm, *BioTechniques* 26:680-682 (1999)]. In Examples 2 and 3 below, two extension reactions were performed in separate tubes in the first stage: (i) one containing the forward primer, and (ii) the other containing the reverse primer. After two cycles, the two reactions are mixed and the standard QuickChange mutagenesis procedure was carried out for an additional 18 cycles. Following amplification, the parental strand was digested with 1 Unit of Dpn1 for 2 hours and an aliquot was transformed into DH5-alpha cells [GeneWiz, New York, N.Y.]. The pET32 Xa/LIC-hdm2 (17-125) vector was used as a template.

When the modified Hdm2 has three amino acid substitutions, as described in the Example 1 below, the GENETAILOR Site-directed Mutagenesis system (Invitrogen, Carlsbad, Calif., USA) was used with the pET32 Xa/LIC-hdm2 (17-125) as the template. In this case the GENETAILOR mutagenesis was performed according to the manufacture's instruction manual, with the lone exception being the use of the pfu turbo DNA polymerase.

The Modified Hdm2 Proteins

In one embodiment, the modified Hdm2 polypeptide of the invention comprises the amino acid sequence SEQ ID NO: 4, wherein one or more of the seven specific amino acid residues denoted as $X_1$-$X_7$ of SEQ ID NO: 4 differs from that of wild-type Hdm2(17-125) (SEQ ID NO: 2). In another embodiment, the modified Hdm2 polypeptide comprises one or more conservative amino acid substitutions at sites other than that of $X_1$-$X_7$ of SEQ ID NO: 4. In certain embodiments, there may be 1, 2, 3, 4, 5, 6, 7, 8, 9 or 10 conservative amino acid substitutions in the sequence at sites other than those indicated in Table 1. In preferred embodiments, there may be 1, 2 or 3 conservative amino acid substitutions at sites other than those indicated in Table 1.

In particular embodiments, the amino acid residues at all seven of the variable positions in the amino acid sequence of SEQ ID NO: 4 are different than that of SEQ ID NO: 2. In a specific embodiment of this type, the modified Hdm2 protein is the Hdm2(HK5) comprising the amino acid sequence of SEQ ID NO: 12 or said modified Hdm2 protein comprising the amino acid sequence of SEQ ID NO: 12 comprising one or more conservative amino acid substitutions at sites other than that of $X_1$-$X_7$ of SEQ ID NO: 4 as described above. In other embodiments, the modified Hdm2 protein comprises the amino acid sequence SEQ ID NO: 4 wherein the amino acid residues at six, five, four or three of the seven variable positions ($X_1$-$X_7$) in the amino acid sequence of SEQ ID NO: 4 are different than that of SEQ ID NO: 2. In certain embodiments, the modified Hdm2 protein comprises one or more conservative amino acid substitutions at sites other than that of $X_1$-$X_7$ of SEQ ID NO: 4.

In yet another embodiment, the amino acid residues at two of the seven variable positions in the amino acid sequence of SEQ ID NO: 4 are different than that of SEQ ID NO: 2. In a particular embodiment of this type the modified Hdm2 protein is Hdm2(F55Y/Y76H) protein comprising the amino acid sequence of SEQ ID NO: 10 or said modified Hdm2 protein comprising one or more conservative amino acid substitutions at sites other than that of $X_1$-$X_7$ of SEQ ID NO: 4. In another embodiment, only one of the amino acid residues at the seven variable positions in the amino acid sequence of SEQ ID NO: 4 is different than that of SEQ ID NO: 2. In a particular embodiment of this type, the modified Hdm2 protein is the Hdm2(F55Y) protein comprising the amino acid sequence of SEQ ID NO: 8 or said modified Hdm2 protein comprising one or more conservative amino acid substitutions at sites other than that of $X_1$-$X_7$ of SEQ ID NO: 4. In another particular embodiment, the modified Hdm2 protein is Hdm2(Y76H) protein comprising the amino acid sequence of SEQ ID NO: 6 or said modified Hdm2 protein comprising one or more conservative amino acid substitutions at sites other than that of $X_1$-$X_7$ of SEQ ID NO: 4.

The present invention further provides a modified Hdm2 protein consisting of, or consisting essentially of, SEQ ID NOs: 4, wherein one or more of the seven specific amino acid residues denoted as $X_1$-$X_7$ of SEQ ID NO: 4 differs from that of wild-type Hdm2(17-125) (SEQ ID NO: 2). In certain embodiments, said modified Hdm2 protein comprises one or more conservative amino acid substitutions at sites other than that of $X_1$-$X_7$ of SEQ ID NO: 4. A modified Hdm2 protein is further provided that consists of, or consists essentially of, SEQ ID NOs: 6, 8, 10 or 12, or said modified Hdm2 protein comprising one or more conservative amino acid substitutions at sites other than that of $X_1$-$X_7$ of SEQ ID NO: 4.

Fusion proteins that comprise the modified Hdm2 proteins of the present invention are also provided, as well as specific peptide fragments of those proteins.

In one such embodiment, the modified Hdm2 protein comprises the amino acid sequence of SEQ ID NO: 4. In a preferred embodiment, the modified Hdm2 protein comprises the amino acid sequence of SEQ ID NO: 6. In one embodiment the compound is Ac-$^{6Br}$WAC$_{3c}$E. In a preferred embodiment, the compound is Ac-$^{6Cl}$WAC$_{3c}$E.

The amino acid sequences of the wild-type (WT) Hdm2 and the following modified Hdm2 proteins corresponding to amino acid residues 17-125 of the full-length wild-type Hdm2 are provided below:

```
WT Hdm2(17-125):
                                        SEQ ID NO: 2
SQIPASEQETLVRPKPLLLKLLKSVGAQKDTYTMKEVLFYLGQYIMTKRL

YDEKQQHIVYCSNDLLGDLFGVPSFSVKEHRKIYTMIYRNLVVVNQQESS

DSGTSVSEN

Modified Hdm2 (X1-X7):
                                        SEQ ID NO: 4
SQIPASEQET_{X1}VRPKP_{X2}LLKLLKSVGAQKDTYTMKEVL_{X3}YLGQYIMTK

RLYDEKQQHIV_{X4}CSND_{X5}LGDLFGV_{X6}SFSVKEHRKIYTMI_{X7}RNLVVV

NQQESSDSGTSVSEN

Modified Hdm2 (Y76H):
                                        SEQ ID NO: 6
SQIPASEQETLVRPKPLLLKLLKSVGAQKDTYTMKEVLFYLGQYIMTKRL

YDEKQQHIVHCSNDLLGDLFGVPSFSVKEHRKIYTMIYRNLVVVNQQESS

DSGTSVSEN

Modified Hdm2 (F55Y):
                                        SEQ ID NO: 8
SQIPASEQETLVRPKPLLLKLLKSVGAQKDTYTMKEVLYYLGQYIMTKRL

YDEKQQHIVYCSNDLLGDLFGVPSFSVKEHRKIYTMIYRNLVVVNQQESS

DSGTSVSEN

Modified Hdm2 (F55Y/Y76H):
                                        SEQ ID NO: 10
SQIPASEQETLVRPKPLLLKLLKSVGAQKDTYTMKEVLYYLGQYIMTKRL

YDEKQQHIVHCSNDLLGDLFGVPSFSVKEHRKIYTMIYRNLVVVNQQESS

DSGTSVSEN

Modified Hdm2 (HK_5):
                                        SEQ ID NO: 12
SQIPASEQETKVRPKPKLLKLLKSVGAQKDTYTMKEVLHYLGQYIMTKR

LYDEKQQHIVKCSNDKLGDLFGVKSFSVKEHRKIYTMIYRNLVVVNQQES

SDSGTSVSEN
```

Modified Hdm2 (HK$_5$) as indicated above has six amino acid substitutions (L27K, L33K, F55H, Y76K, L81K, and P89K) selected to specifically increase Hdm2 solubility; only two are derived from natural variants.

Column 1 of Table 1 denotes the seven variable amino acid positions in the sequence of SEQ ID NO: 4, and presents the numbering of the amino acid positions in relation to both the full-length wild-type Hdm2 and the corresponding numbering of the wild-type Hdm2(17-125) having the amino acid sequence of SEQ ID NO: 2 (in parentheses). The seven defined positions in SEQ ID NO: 4 in which the amino acid residue can specifically vary are denoted as $X_1$-$X_7$ (column 2). The amino acid residues in the full-length wild-type Hmd2 occupying those seven positions are listed in column 3. All of the natural variants identified by the Clustalw alignment of the amino acid sequences of Hdm2 and Hdm4 analogs using *Brachydanio rerio* (Zebrafish), *Canis familiaris* (Dog), *Equus caballus* (Horse), *Homo sapiens* (Human), *Mesocricetus auratus* (Golden Hamster), *Mus musculus* (Mouse), *Xenopus laevis* (African Clawed Frog) and *Gallus gallus* (Chicken) are provided in column 4. All acceptable amino acids are listed in Column 5, including the amino acid residues for the seven respective positions of the wild-type Hmd2, which are in bold.

TABLE 1

Amino Acid Substitutions for SEQ ID NO: 4

| A.A. Position | A.A. Name | Hdm2 | Species Variants | Acceptable Variants |
|---|---|---|---|---|
| 27 (11) | $X_1$ | L27 | Q | L, K, R, Q, E, D, S |
| 33 (17) | $X_2$ | L33 | Q | L, K, R, Q, E, D, S |
| 55 (39) | $X_3$ | F55 | L, Y, H | F, H, Y, K, R, Q, E, D, S |
| 76 (60) | $X_4$ | Y76 | H | Y, H, K, R, Q, E, D, S |
| 81 (65) | $X_5$ | L81 | A, P, C | L, K, R, Q, E, D, S, P, A |
| 89 (73) | $X_6$ | P89 | K, V, Q, T | P, K, R, Q, E, D, S |
| 104 (88) | $X_7$ | Y104 | I, N, R, S | Y, K, R, Q, E, D, S, N |

In addition, the modified Hdm2 proteins of the present invention may include conservative amino acid substitutions relative to the wild type sequence of Hdm2 (other than those at the seven positions identified in Table 1, for which the alternatives are specifically defined). In general, there are no more than 11 conservative amino acid substitutions (e.g., no more than 10, 9, 8, 7, 6, 5, 4, 3, 2, 1 or 0 conservative amino acid substitutions). In a preferred embodiment, there are no more than 3 conservative amino acid substitutions (0, 1, 2 or 3).

All of the modified Hdm2 proteins of the present invention also can be part of a chimeric protein. In a specific embodiment, a chimeric modified Hdm2 protein is expressed in a prokaryotic cell. Such a chimeric protein can be a fusion protein used to isolate a modified Hdm2 protein of the present invention, through the use of an affinity column that is specific for the protein fused to the modified Hdm2 protein. Examples of such fusion proteins include: a glutathione-S-transferase (GST) fusion protein, a maltose-binding protein (MBP) fusion protein, a FLAG-tagged fusion protein, or a poly-histidine-tagged fusion protein. Specific linker sequences such as a Ser-Gly linker can also be part of such a fusion protein. A chimeric modified Hdm2 protein of the present invention also can be expressed in a eukaryotic cell.

Expression of a chimeric, modified Hdm2 protein, or fragment thereof, as a fusion protein can facilitate stable expression, and/or allow for purification based on the properties of the fusion partner. Thus the purification of the recombinant polypeptides of the present invention can be simplified through the use of fusion proteins having affinity Tags. For example, GST binds glutathione conjugated to a solid support matrix, MBP binds to a maltose matrix, and poly-histidine chelates to a Ni-chelation support matrix [see Hochuli et al., *Biotechnology* 6:1321-1325 (1998)]. The fusion protein can be eluted from the specific matrix with appropriate buffers, or by treating with a protease that is specific for a cleavage site that has been genetically engineered in between the modified Hdm2 protein and its fusion partner. Alternatively, a modified Hdm2 protein can be combined with a marker protein such as green fluorescent protein [Waldo et al., *Nature Biotech.* 17:691-695 (1999); U.S. Pat. No. 5,625,048 and WO 97/26333].

Alternatively or in addition, other column chromatography steps (e.g., gel filtration, ion exchange, affinity chromatography etc.) can be used to purify the recombinant modified Hdm2 proteins of the present invention. In many cases, such column chromatography steps employ high performance liquid chromatography or analogous methods in place of the more classical gravity-based procedures. The specific details for the preferred purification procedure of the modified Hdm2 proteins of the present invention are provided in Example 1 below.

In addition, the modified Hdm2 proteins of the present invention and proteins thereof including, specific peptide fragment thereof can be chemically synthesized [see e.g., Synthetic Peptides: *A User's Guide*, W.H. Freeman & Co., New York, N.Y., pp. 382, Grant, ed. (1992)].

Crystallization of Protein

The modified Hdm2 proteins result in novel crystal forms not obtained with the wild-type protein. In one embodiment, the modified Hdm2 protein may be crystallized in the presence of one of a variety of different compounds (e.g., an small molecule inhibitor or a peptide from p53). Further, a compound complexed to modified Hdm2 may be exchanged in the crystal by a second compound (e.g., a potential inhibitor) by soaking the crystal in a solution containing the second compound. These crystals and the resulting structures can be used to obtain a detailed view of various inhibitors that bind to Hdm2, providing a basis for further design of potent inhibitors of Hdm2 to be used as anticancer agents.

Crystallization may be accomplished by using any of the known methods in the art (Giegé, et al., (1994) Acta Crystallogr. D50: 339-350; McPherson, (1990) Eur. J. Biochem. 189: 1-23). Such techniques include microbatch, hanging drop, seeding and dialysis. Preferably, hanging-drop vapor diffusion (McPherson, (1976) J. Biol. Chem. 251: 6300-6303) or microbatch methods (Chayen (1997) Structure 5: 1269-1274) are used. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane that is placed into a solution containing precipitant. Equilibration across the membrane increases the precipitant concentration thereby causing the polypeptide to reach supersaturation levels. It is desirable to use a modified Hdm2 protein preparation having a concentration of at least about 1 mg/mL and preferably about 5 mg/mL to about 60 mg/mL, more preferably about 20 mg/mL to about 50 mg/mL, even more preferably about 30 mg/mL to about 40 mg/mL. Crystallization may be achieved in precipitant solutions containing polyethylene glycol 1000-20,000 (PEG; average molecular weight ranging from about 1000 to about 20,000 Da), preferably about 2000 to about 6000 Da, more preferably about 5000 Da, with concentrations ranging from about 10% to about 50% (w/v). It may also be desirable to include a protein stabilizing agent. If glycerol is chosen as the protein stabilizing agent, it is preferably provided at a concentration ranging from about 0.5% to about 20%. A suitable salt, such as magnesium chloride, potassium chloride, sodium chloride, lithium chloride or sodium citrate may also be desirable in the precipitant solution, preferably in a concentration ranging from about 1 mM to about 2000 mM. The precipitant is preferably buffered to a pH of from about 6.5 to about 9.5, preferably about 7.5-8.5. Specific buffers useful in the precipitant solution may vary and are well-known in the art (Scopes, Protein Purification: Principles and Practice, Third ed., (1994) Springer-Verlag, New York). Examples of useful buffers include, but are not limited to, Hepes, Tris, MES and acetate. Crystals routinely grow at a wide range of temperatures. It is, however, preferred that crystals form at temperatures between about 2° C. and about 26° C.

The crystals of the present invention have a wide range of uses. For example, high quality crystals are suitable for X-ray or neutron diffraction analysis to determine the three dimensional structure of Hdm2 and in particular to assist in the identification of the protein's effector sites. Knowledge of these sites and solvent accessible residues allow structure-based design and construction of agonists and antagonists for Hdm2.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals that are preferred for diffraction analysis.

Once a crystal of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention may be amenable to X-ray crystallography for providing the three-dimensional structure of a Hdm2 polypeptide. The present invention includes crystals which effectively diffract X-rays for the determination of the atomic coordinates of Hdm2 to a resolution of greater than about 5.0 Ångströms (e.g., about 4.5 Å, about 4.0 Å, about 3 Å, about 2.5 Å, about 2 Å, about 1 Å, about 0.5 Å, about 0.1 Å), preferably greater than about 4.0 Ångströms (e.g., about 3 Å, about 2.5 Å, about 2 Å, about 1 Å, about 0.5 Å, about 0.1 Å), more preferably greater than about 2.8 Ångströms (e.g., about 2.5 Å, about 2 Å, about 1 Å, about 0.5 Å, about 0.1 Å) and most preferably greater than about 2.0 Ångströms (e.g., about 1.5 Å, about 1.0 Å, about 0.5 Å, about 0.1 Å).

The present invention includes Hdm2 crystals whose three-dimensional structure is described by the structure coordinates set forth in Table 3 or 4. The scope of the present invention also includes crystals which possess structural coordinates which are similar to those set forth in Table 3 or 4; preferably, the crystals or the soluble polypeptides which are used to form the crystals exhibit Hdm2 catalytic activity and/or p53 binding (see above). In some embodiments, the crystal comprises a polypeptide that comprises the amino acid sequence of SEQ ID NO: 4, wherein one or more of the seven specific amino acid residues denoted as $X_1$-$X_7$ of SEQ ID NO: 4 differs from that of wild-type Hdm2(17-125) (SEQ ID NO: 2). In other embodiments, the crystal comprises a polypeptide that comprises the amino acid sequence selected from the group consisting of SEQ ID NOS: 8 and 12. In another embodiment, the modified Hdm2 polypeptide comprises one or more conservative amino acid substitutions at sites other than that of $X_1$-$X_7$ of SEQ ID NO: 4. Structural similarity between crystals is discussed in detail below.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for a protein or a protein complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The present invention includes crystals exhibiting structure coordinates which are similar to those set forth in Table 3 or 4 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Table 3 or 4, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Table 3 or 4 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, CA, C and O) for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any set of structure coordinates of a molecule that has a RMSD of conserved residue backbone atoms (N, CA, C, O) of less than about 2.0 Å when superimposed—using backbone atoms—on the relevant structure coordinates of Table 3 or 4 are considered identical and are within the scope of the present invention. Preferably the crystal is a modified Hdm2 protein as defined above. Preferably, the root mean square deviation is less than about 1.5 Å, more preferably less than 1.0 Å, even more preferably, the root mean square deviation is less than about 0.5 Å and most preferably, the root mean square deviation is less than about 0.1 Å.

The term "least squares" refers to a method based on the principle that the best estimate of a value is that in which the sum of the squares of the deviations of observed values is a minimum.

In one embodiment, the modified Hdm2 protein comprises the amino acid sequence of SEQ ID NO: 6. In a particular embodiment of this type, the crystal has the space group of $P2_12_12_1$, having unit cell dimensions of: a=41.1, b=66.1, c=96.1 Angstroms. In a particular embodiment of this type, the modified Hdm2 protein comprises the amino acid sequence of SEQ ID NO: 10. In a particular embodiment of this type, the crystal has the space group of $P2_12_12_1$, having unit cell dimensions of: a=38.0, b=45.3, c=64.0 Angstroms. In a related embodiment, the crystal comprises a protein-ligand binding complex with the modified Hdm2 protein.

In accordance with the present invention, the structure coordinates of the Hdm2 polypeptide and portions thereof may be stored in a machine-readable storage medium. Such data may be used for a variety of purposes, such as drug discovery and X-ray crystallographic analysis of a protein crystal (e.g., for producing a three-dimensional representation of Hdm2). Accordingly, one aspect of this invention provides a machine-readable data storage medium comprising a data storage material encoded with the structure coordinates set forth in Table 3 or 4. The machine-readable data storage medium may also include any set of structure coordinates of a molecule that has a root mean square deviation of conserved residue backbone atoms (N, CA, C, O) of less than about 1.5 Å, preferably, less than about 1.0 Å, more preferably less than about 0.5 Å and even more preferably less than about 0.1 Å when superimposed—using backbone atoms—on the relevant structure coordinates of Table 3 or 4.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer D520. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of Hdm2 or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In preferred embodiments, the computer possesses a display which is displaying a three dimensional representation of Hdm2 or a fragment or homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure Based Drug Design

The present invention permits the use of structure-based drug design techniques to design, select, and synthesize chemical entities, including inhibitory compounds that are capable of binding to a Hdm2 polypeptide. Also, de novo and iterative drug design methods can be used to develop drugs from the structure of the Hdm2 crystals of this invention.

One particularly useful drug design technique enabled by this invention is structure-based drug design. Structure-based drug design is a method for optimizing associations between a protein and a compound by determining and evaluating the three-dimensional structures of successive sets of protein/compound complexes.

Those skilled in the art will appreciate that association of natural ligands or substrates with the binding pockets of their corresponding receptors, enzymes or specific binding proteins is the basis of many biological mechanisms of action. The term "binding pocket", as used herein, may refer to any region of a molecule or molecular complex, that, as a result of its shape, favorably associates with another chemical entity or compound. Similarly, drugs may exert their biological effects through association with the binding pockets of receptors and/or specific binding proteins. Such association may occur with all or any part of the binding pockets. An understanding of such associations will help lead to the design of drugs having more favorable associations with the target protein, and thus, improved biological effects. Therefore, this information is valuable in designing potential protein inhibitors, such as inhibitors of Hdm2.

In iterative structure-based drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of a new polypeptide, solving the three-dimensional structure of the polypeptide, and comparing the associations between the new protein and previously solved protein. By observing how changes in the compound affected the protein/compound associations, these associations may be optimized.

In some cases, iterative structure-based drug design is carried out by forming successive protein-compound complexes and then crystallizing each new complex. Alternatively, a pre-formed protein crystal is soaked in the presence of an inhibitor or other binding compound, thereby forming a protein/compound complex and obviating the need to crystallize each individual protein/compound complex. Advantageously, the modified Hdm2 crystals provided by this invention may be soaked in the presence of compounds, such as Hdm2 inhibitors, substrates or other ligands to provide novel Hdm2/compound crystal complexes. In one embodiment, the complexes may be produced and screened using high throughput methods to quickly identify or design potential inhibitors of Hdm2.

The structure coordinates set forth in Table 3 or 4 can also be used to aid in obtaining structural information about another crystallized molecule or molecular complex. This may be achieved by any of a number of well-known techniques, including molecular replacement.

The structure coordinates set forth in Table 3 or 4 can also be used for determining at least a portion of the three-dimensional structure of molecules or molecular complexes which contain at least some structurally similar features to Hdm2. In particular, structural information about another crystallized molecule or molecular complex may be obtained by well-known techniques, including molecular replacement.

Therefore, another aspect of this invention provides a method of utilizing molecular replacement to obtain structural information about a crystallized molecule or molecular complex, whose structure is unknown, comprising the steps of generating an X-ray diffraction pattern from said crystallized molecule or molecular complex and applying crystallographic phases derived from at least a portion of the structure coordinates set forth in Table 3 or 4 to the X-ray diffraction pattern to generate a three-dimensional electron density map of the molecule or molecular complex whose structure is unknown.

Once the structure coordinates of a protein crystal have been determined, they are useful in solving the structures of other crystals. In addition, the structure of Hdm2 homologues may be determined from the structural coordinates of the present invention. For example, polypeptides may be crystallized and their structures elucidated by, for example, difference Fourier techniques and molecular replacement.

By using molecular replacement, all or part of the structure coordinates of the Hdm2 polypeptide provided by this invention (and set forth in Table 3 or 4) can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the modified Hdm2 crystal according to Table 3 or 4 within the unit cell of the crystal of the unknown molecule or molecular complex so as best to account for the observed X-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55-77 (1985); Rossman, ed., "The Molecular Replacement Method", *Int. Sci. Rev. Ser.*, No. 13, Gordon & Breach, New York (1972)).

Phase information from the structure coordinates of the present invention may be used to elucidate the structure of other crystals. For example, the structure of Hdm2 in complex with other atoms or molecules may be elucidated. Such complexes include, for example, those containing atoms soaked into or cocrystallized within the crystal lattice. Other structures which can be elucidated using the phase information of the present invention include for example other proteases or homologues or mutants thereof having sufficient three-dimensional structure similarity to Hdm2 complex as to be solved using molecular replacement. Also, these protein molecules in a complex with a small molecule substrate(s), inhibitor(s), transition state analog(s), product(s) or analog(s) of any of these may also be solved using the phase information of the present invention. Other complexes whose structure can be elucidated from the phase information of the present invention include a modified Hdm2 complexed with an inhibitor other than those presented herein. Complexes containing a combination of the above molecules may also be solved using the phase information of the present invention.

The structure of any portion of any crystallized molecule or molecular complex that is sufficiently homologous to any portion of the modified Hdm2 protein can be solved by this method. The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

In a preferred embodiment, the method of molecular replacement is utilized to obtain structural information about a molecule wherein the molecule comprises a Hdm2 polypeptide complex. The structure coordinates of modified Hdm2 provided by this invention are particularly useful in solving the structure of other crystal forms of Hdm2 polypeptide complexes. This approach enables the determination of the optimal sites for interaction between chemical entities, including interaction of candidate inhibitors with Hdm2.

Modified Hdm2 crystals may be studied using well-known X-ray diffraction techniques and may be refined versus X-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; *Meth, Enzymol.*, vol. 114 & 115, H. W. Wyckoff et al., eds., Academic Press (1985)). This information may be used to optimize known Hdm2 inhibitors and to design new Hdm2 inhibitors.

Once a three-dimensional structure of a crystal comprising a modified Hdm2 protein in a protein-ligand complex is determined, the potential inhibitor of Hdm2 can be examined through the use of computer modeling using a docking program such as GRAM, DOCK, or AUTODOCK [Dunbrack et al., *Folding & Design*, 2:27-42 (1997)]. This procedure can include computer fitting of potential inhibitors to the modified Hdm2 protein to ascertain how well the shape and the chemical structure of the potential modulator will interact with the modified Hdm2 protein [Bugg et al., *Scientific American*, Dec.: 92-98 (1993); West et al., *TIBS*, 16:67-74 (1995)]. Computer programs can also be employed to estimate the attraction, repulsion, and steric hindrance of the modified Hdm2 protein with an inhibitor.

Generally the tighter the fit, the lower the steric hindrances, and the greater the attractive forces, the more potent the inhibitor, since these properties are consistent with a tighter binding constant. Furthermore, the more specificity in the design of a potential drug the more likely that the drug will not interact as well with other proteins. This will minimize potential side-effects due to unwanted interactions with other proteins.

Compounds that may be used initially have been discussed by Chene [*Nature* 3:102-109 (2003)]. In addition, the present invention discloses the acetylated tripeptides, (a) Ac-$^{6Cl}$WAC$_{3c}$E and (b) Ac-$^{6Br}$WAC$_{3c}$E, as shown respectively below, which can individually bind a modified Hmd2 protein in protein-ligand complex and form an X-ray diffractable crystal.

These ligands then can be systematically modified by computer modeling programs until one or more promising potential analogs are identified. Such analysis has been shown to be effective in the development of HIV protease inhibitors [Lam et al., *Science* 263:380-384 (1994); Wlodawer et al., *Ann. Rev. Biochem.* 62:543-585 (1993); Appelt, *Perspectives in Drug Discovery and Design* 1:23-48 (1993); Erickson, *Perspectives in Drug Discovery and Design* 1:109-128 (1993)]. Alternatively, a potential inhibitor initially can be obtained by screening a random peptide library or a chemical library. In the former case, a random peptide library can be produced by recombinant bacteriophage, for example, [Scott and Smith, *Science*, 249:386-390 (1990); Cwirla et al., *Proc. Natl. Acad. Sci.*, 87:6378-6382 (1990); Devlin et al., *Science*, 249:404-406 (1990)]. This approach may be particularly useful in this case since the natural binding partner for Mdm2 is the p53 protein. In any case, a peptide selected in this manner could then be systematically modified by computer modeling programs, as described above.

If a potential inhibitor is a small organic compound, it can be selected from a library of chemicals, as are commercially available. Alternatively, the small organic compound may be synthesized de novo. Once obtained, the potential inhibitor can be further tested in a standard binding and/or functional assay with Hdm2, a modified Hdm2 protein or active fragments thereof.

For example, a binding assay can be performed following the attachment of the Hdm2 protein to a solid support. Methods for placing Hdm2 protein on the solid support are well known in the art and include such things as linking biotin to the Hdm2 protein and linking avidin to the solid support. The solid support can be washed to remove unbound protein. A solution of a labeled potential inhibitor can be contacted with the solid support. The solid support is washed again to remove the potential inhibitor not bound to the support. The amount of labeled potential inhibitor remaining with the solid support, and thereby bound to the Hdm2 protein can be determined. Alternatively, or in addition, the dissociation constant between the labeled potential inhibitor and the Hdm2 protein, for example, can be determined. Suitable labels for either the Hdm2 protein or the potential inhibitor include, radioactive labels (e.g., $^{14}$C, $^{1}$H) and fluorescent labels such as fluorescein isothiocyanate (FITC).

In another embodiment, a Biacore machine can be used to determine the binding constant of the Hdm2 protein with a potential inhibitor [O'Shannessy et al. *Anal. Biochem.* 212: 457-468 (1993); Schuster et al., *Nature* 365:343-347 (1993)].

In addition, an inhibitor can be identified using an ELISA-based competition assay [Bottger et al., *Oncogene* 13:2141-2147 (1996); Bottger et al., *J. Miol. Biol.* 269:744-756 (1997)]. For example, the p53 protein or Hdm2-binding fragment thereof can be biotinylated and immobilized on a streptavidin-coated ELISA plate. Hdm2 is then incubated alone (in a control) or in the presence of a potential inhibitor. The Hdm2 solutions are then individually contacted with the immobilized p53 protein or Hdm2-binding fragment thereof. The binding of the Hdm2 is then determined, e.g., with a detectable anti-Hdm2 antibody. When the amount of Hdm2 detected is lower in the sample incubated with the potential inhibitor relative to the control, the potential inhibitor is identified as an inhibitor.

When a promising inhibitor is identified, a crystal comprising a protein-ligand complex of the inhibitor and a modified Hdm2 protein can be prepared. The three-dimensional structure of the resulting crystalline protein-ligand complex can then be determined by molecular replacement analysis, for example.

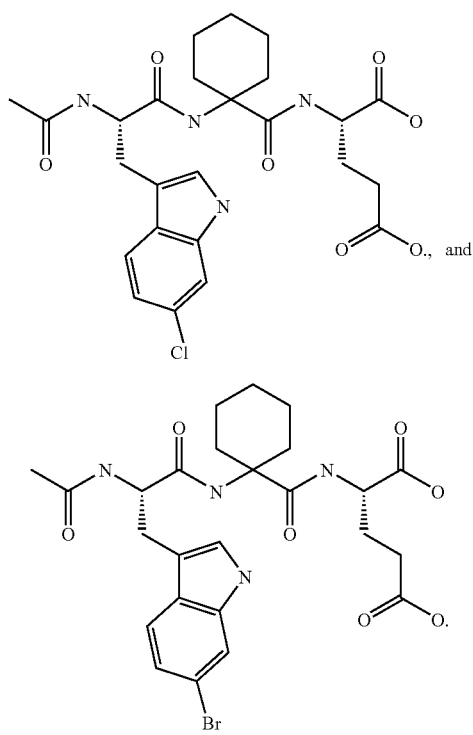

Molecular replacement involves the use of a known three-dimensional structure as a search model to determine the structure of a closely related molecule or protein-ligand complex in a different crystalline form. The measured X-ray diffraction properties of the new crystal are compared with the search model structure to compute the position and orientation of the protein in the new crystal. Computer programs that can be used include: X-PLOR [Brunger et al., *Acta Crystallogr. A* 46:585-593 (1990); Brunger et al., *Acta Crystallogr. D Biol. Crystallogr.*, 54:905-921 (1998)], CNS, (Crystallography and NMR System, a next level of XPLOR), and AMORE [Navaza, *Acta Crystallographics* ASO, 157-163 (1994)]. Once the position and orientation are known, an electron density map can be calculated using the search model to provide X-ray phases. Thereafter, the electron density is inspected for structural differences and the search model is modified to conform to the new structure. Using this approach, it is possible to solve the three-dimensional structures of crystals of any protein-ligand complex of the modified Hdm2 protein.

For all of the drug screening assays described herein, further refinements to the structure of the drug will generally be necessary and can be made by the successive iterations of any and/or all of the steps provided by the particular drug screening assay and/or in combination with other such drug screening assays.

A candidate drug selected by performing structure based drug design can then be assayed in situ and/or in vivo. For example, a candidate drug can be evaluated for cellular activity by incubating the candidate drug in cell cultures, e.g. using HCT-116 cells or OSA-CL cells, and then measuring its effect on cellular proliferation and expression levels of proteins that are transcriptionally regulated by p53 such as p21waf1 and Hdm2 [Chene et al., *J. Mol. Biol.* 299:245-256 (2000)]. A candidate drug is identified as a drug if in the presence of the drug relative to in its absence, the amount of cellular proliferation decreases and/or the amount of a protein that is transcriptionally regulated by p53 increases.

Indeed, methods of testing such potential candidate drugs in animal models are well known in the art. The potential drugs can be administered by a variety of ways including topically, orally, subcutaneously, or intraperitoneally depending on the proposed use. Generally, at least two groups of animals are used in the assay, with at least one group being a control group that is administered the administration vehicle without the potential drug.

TABLE 2

TABLE OF SEQUENCES

| SEQ ID NO: | Type | Description |
|---|---|---|
| 1 | N.A. | WT Hdm2 (17-125) |
| 2 | A.A. | WT Hdm2 (17-125) |
| 3 | N.A. | modified Hdm2 ($X_1$-$X_7$) |
| 4 | A.A. | modified Hdm2 ($X_1$-$X_7$) |
| 5 | N.A. | modified Hdm2 (Y76H) |
| 6 | A.A. | modified Hdm2 (Y76H) |
| 7 | N.A. | modified Hdm2 (F55Y) |
| 8 | A.A. | modified Hdm2 (F55Y) |
| 9 | N.A. | modified Hdm2 (F55Y/Y76H) |
| 10 | A.A. | modified Hdm2 (F55Y/Y76H) |
| 11 | N.A. | modified Hdm2 ($HK_5$) |
| 12 | A.A. | modified Hdm2 ($HK_5$) |
| 13 | N.A. | Hdm2 (F55Y) Primer |
| 14 | N.A. | RChdm2 (F55Y) Primer |
| 15 | N.A. | Hdm2 (Y76H) Primer |
| 16 | N.A. | RChdm2 (Y76H) |
| 17 | N.A. | Y104S-GTAILOR-F Primer |
| 18 | N.A. | Y104-GTAILOR-R Primer |

The present invention may be better understood by reference to the following non-limiting examples, which are provided as exemplary of the invention. The following examples are presented in order to more fully illustrate certain embodiments of the invention. They should in no way be construed as limiting the broad scope of the invention.

EXAMPLES

Example 1

Preparation of Modified Hdm2

Preparation of Hdm2 Constructs

Hdm2 was either modified with a single amino acid change, or with a double amino acid change using the QuickChange kit (Stratagene, La Jolla, Calif., USA) and the pET32-Xa/LIC-hdm2 (17-125) vector as a template. The pET32-Xa/LIC parental vector was obtained from Novagen (San Diego, Calif.). Hdm2(F55Y), Hdm2(Y76H) and Hdm2 (F55Y/Y76H) were constructed in this manner.

A modified Hdm2 having three amino acid substitutions, Hdm2(F55Y/Y76H/Y104S) was generated using GENETAILOR Site-directed Mutagenesis system (Invitrogen, Carlsbad, Calif., USA) with the vector indicated above as the template. The following primers were used to generate the above-identified modified Hdm2 proteins:

(1) Hdm2(F55Y) Primer:
SEQ ID NO: 13
5' CTATGAAAGAGGTTCTTTATTATCTTGGCCAGTATATTATGAC 3'

(2) RChdm2(F55Y) Primer:
SEQ ID NO: 14
5' GTCATAATATACTGGCCAAGATAATAAAGAACCTCTTTCATAG 3'

(3) Hdm2(Y76H) Primer:
SEQ ID NO: 15
5' GAGAAGCAACAACATATTGTACATTGTTCAAATGATCTTCTAGG 3'

(4) RChdm2(Y76H) Primer:
SEQ ID NO: 16
5' CCTAGAAGATCATTTGAACAATGTACAATATGTTGTTGCTTCTC 3'

(5) Y104S-GTAILOR-F Primer:
SEQ ID NO: 17
5' CAGGAACTTGGTAGTAGTCAATCAGCAGG 3'

(6) Y104-GTAILOR-R Primer:
SEQ ID NO: 18
5' GACTACTACCAAGTTCCTGGAGATCATGGT 3'

QuickChange mutagenesis was performed in two steps as previously described [Wang et al., *BioTechniques* 26:680-682 (1999)]. In the first stage two extension reactions were performed in separate tubes; one containing the forward primer and the other containing the reverse primer. After two cycles, the two reactions were mixed and the standard QuickChange mutagenesis procedure was carried out for an additional 18 cycles. Following amplification, the parental strand was digested with 1 U of Dpn1 for 2 hours and an aliquot was transformed into DH5-α cells. The GENETAILOR mutagenesis was performed according to the manufacturer's instructions except that pfu turbo DNA polymerase was used instead of the polymerase recommended by manufacture. All constructs were confirmed by sequencing (GeneWiz, New York, N.Y.).

Expression of Modified Hdm2

A colony from freshly transformed cells was grown at 37° C. to an optical density (OD) of 2.0 in 10 ml TERRIFIC broth (Mediatech, Inc.) containing 100 µg/ml carbenicilin and 1% glucose. This 10 ml culture was then used to inoculate a 1 liter culture having the same medium composition. The 1 liter culture was grown at 37° C. to an OD of 2.0, stored at 4° C. overnight, and then used to inoculate a 10 liter tank containing TERRIFIC broth and 100 μg/ml carbenicilin. The 10 liter culture was grown at 37° C. to an OD of 1.5-2.0 before lowering the temperature to 16° C. The 10 liter culture was then induced with 1 mM IPTG, and the cells were harvested 18 hours post-induction.

Purification of Modified Hdm-2 Proteins

The purification protocol as exemplified herein for Hdm2 (F55Y/Y76H) is applicable for all of the modified Hdm2 proteins of the present invention.

IPTG-induced cells containing Hdm2(F55Y/Y76H) were harvested from the 10 liter fermentation, as described above. The cells were suspended in 500 ml of 50 mM Tris-Cl Buffer, pH $8.0_{rt}$ (room temperature), 0.3 M NaCl, 10% (v/v) glycerol, 5 mM β-mercaptoethanol, 25 mM imidazole, 18,000 Units/liter endonuclease (ultrapure benzonase; SIGMA), and 6 ml/liter of CALBIOCHEM Protease Inhibitor Cocktail III. (All processing was performed at 4° C.) To homogenize the resulting cell suspension, it was passed through a large OMNI Mixer probe for 45 seconds, three times. The cell suspension was kept on ice for 2 minutes between each 45 second passage. The cells were then broken by three passages of the homogenized cell suspension through a Microfluidizer. The extract was recovered by centrifugation at 205,000×g for 80 minutes at 4° C.

The resulting 645 ml extract was mixed end over end for 50 minutes with 28 ml of QIAGEN Ni-NTA SUPERFLOW resin, which had been equilibrated with the equilibration buffer [50 mM Tris-Cl, pH $8.0_{rt}$, 0.3 M NaCl, 5 mM β-mercaptoethanol and 25 mM imidazole]. The supernatant was decanted, and the resin was then washed with 600 ml of the equilibration buffer. The resin was poured into a 2.6×5.3 cm column, washed with an additional 200 ml of equilibration buffer at 3.6 ml/min, and finally eluted with 50 mM Tris-Cl, pH $8.0_{rt}$, 0.1 M NaCl, 250 mM imidazole, 5 mM β-mercaptoethanol and 20% glycerol.

A 0.64 ml volume of 0.5 M $CaCl_2$ was added to the eluted fusion protein pool (195 mg of protein in 63 ml of elution buffer). The pooled protein was then diluted to 1 mg/ml with 50 mM Tris-Cl, pH $8.0_{rt}$, 0.1 M NaCl, 10% glycerol, 5 mM $CaCl_2$ and 5 mM β-mercaptoethanol. A 1.95 ml volume of 2000 Units/ml Factor Xa protease (NOVAGEN) was added, and the pooled protein was dialyzed overnight versus 3.87 liters of the same buffer.

A 4.33 ml volume of 1M imidazole, pH 8.0, was added to the 200 ml of cleaved, pooled fusion protein, to bring the imidazole concentration to 24 mM. The pooled protein was then applied at a rate of 3.6 ml/min to a 50 ml (2.6×9.4 cm) column of QIAGEN Ni-NTA SUPERFLOW resin that had been equilibrated with equilibration buffer. The column was then washed with the equilibration buffer.

The 230 ml flow-through was dialyzed versus three changes (6 liters, 5 liters and 5 liters) of Buffer A [25 mM Hepes-KOH, pH 7.5, 0.15 M KCl, 1 mM $Na_2$-EDTA, 0.03% sodium azide and 5 mM dithiothreitol]. All manipulations of the modified Hdm2 were in Buffer A from this point on. The dialyzed pooled protein was concentrated to 8.5 ml with an AMICON YM10 membrane, centrifuged at 205,000×g for 15 minutes, and then applied to a 2.6×60 cm column of PHARMACIA SUPERDEX-75 at a flow rate of 0.8 ml/min. The resulting eluant was collected in 3.2 ml fractions.

Fractions 66-75 contained the purified, modified Hdm2 monomer. These fractions were pooled and a protein concentration of 3.6 mg/ml was determined using $\epsilon_{276}$=10,150 $M^{-1}$ $cm^{-1}$ in 20 mM sodium phosphate, pH 6.5, with 6 M guanidine hydrochloride (ExPASy-ProtParam Tool). This determination correlated with that determined by the Bradford dye binding assay (BIORAD), using bovine serum albumin as the protein standard.

Example 2

Preparation and Crystallization of Hdm2 F55Y/Y76H-Tripeptide Complex

The modified Hdm2 (F55Y/Y76H) protein was prepared by means of QuickChange mutagenesis as disclosed in Example 1 using the appropriate primers. A small scale expression study was carried out to evaluate the solubility and expression level of this construct. The expression level of the soluble Hdm2(F55Y/Y76H) protein is 2 to 3 fold higher than wild type. 110 mgs of the Hdm2(F55Y/Y76H) was purified from a 10 L culture through the four-step purification protocol described above.

A 13 ml aliquot of the 3.6 mg/ml pool was concentrated to a 1.25 mM concentration (in 3 ml), on an AMICON 5000 mwco Ultrafree membrane. A 3 ml aliquot of 8.5 mM SCH549128 (MW=535) in Buffer A was added to the concentrated aliquot. The complex was incubated at room temperature for 10 minutes, and then concentrated as above, to a final volume of 1.3 ml.

The HDM2 (F55Y/Y76H) protein-tripeptide complex was crystallized using a hanging-drop vapor diffusion method. The protein (0.5 μl; 34 mg/ml) in 25 mM Hepes-potassium hydroxide, pH7.5, 0.15 M potassium chloride, 1 mM EDTA, 0.03% sodium azide and 5 mM DTT buffer was mixed with an equal volume of precipitant solution [1.4 M tri sodium citrate, 0.1 M sodium Hepes, pH 7.5] placed on the underside of a siliconized glass coverslip and sealed in close proximity to 1 ml of the precipitant solution. Crystallization plates were incubated at 22° C.; rectangular rod crystals (0.02×0.2 mm) grew over 2-30 days.

Prior to data collection, crystals were washed with the reservoir solution of the crystallization setup and transferred into the same solution with 20% glycerol added. The crystals were then flash-cooled in a nitrogen stream at 95 K. X-ray diffraction was collected using a Rigaku generator equipped with a Raxis 4++ detector. Data were integrated and scaled using the HKL package.

Data Collection Statistics:

| | |
|---|---|
| Resolution | 50.0-1.70 Å |
| No. of collected reflections | 135908 |
| No. of unique reflections (F >= 0) | 12484 |
| R-sym | 6.7% |
| Percent of theoretical (I/s >= 1) | 98.7% |
| Unit Cell | a = 37.999 Å, b = 45.333 Å, c = 63.999 Å, α = β = γ = 90° |
| Space Group | $P2_12_12_1$ |
| Asymmetric unit | 1 molecule |

The crystal structure was solved using molecular replacement using the search models 1YCQ and 1YCR from the PDB. Refinement was done using the program CNX.

Theoretical Number of Reflections 9121

| | |
|---|---|
| Resolution Limits | 50.0-1.90 Å |
| Number of unobserved reflections | 106 (1.2%) |
| Number of reflections in working set | 8592 (98.8%) |
| Number of reflections in test set | 423 (4.6%) |

-continued

| | |
|---|---|
| Number of protein residues | 87 |
| Number of solvent atoms | 44 |
| R-factor | 0.223 |
| R-free | 0.243 |
| RMSD bond length | 0.0083 Å |
| RMSD bond angles | 1.46° |

The structural coordinates for the above-described Hdm2 crystal are set forth below in Table 3, which is in Protein Data Bank (PDB) file format. The numbered columns refer to the following:

| Col. # | Reference |
|---|---|
| 1 | Atomic coordinate records for standard groups |
| 2 | Atom serial number |
| 3 | Atom name |
| 4 | Residue name |
| 5 | Residue sequence number |
| 6 | Orthogonal coordinates for X in Angstroms |
| 7 | Orthogonal coordinates for Y in Angstroms |
| 8 | Orthogonal coordinates for Z in Angstroms |
| 9 | Occupancy |
| 10 | Temperature factor |
| 11 | Element symbol |

TABLE 3

| 1 | 2 | 3 | 4 | 5 | 6 | 7 | 8 | 9 | 10 | 11 |
|---|---|---|---|---|---|---|---|---|---|---|
| ATOM | 1 | CB | GLU | 25 | 8.599 | 29.031 | 2.725 | 1.00 | 52.10 | C |
| ATOM | 2 | CG | GLU | 25 | 7.336 | 29.192 | 3.556 | 1.00 | 55.02 | C |
| ATOM | 3 | CD | GLU | 25 | 6.648 | 27.844 | 3.697 | 1.00 | 57.01 | C |
| ATOM | 4 | OE1 | GLU | 25 | 5.517 | 27.697 | 3.186 | 1.00 | 58.12 | O |
| ATOM | 5 | OE2 | GLU | 25 | 7.235 | 26.932 | 4.322 | 1.00 | 57.62 | O |
| ATOM | 6 | C | GLU | 25 | 10.683 | 30.035 | 1.753 | 1.00 | 47.48 | C |
| ATOM | 7 | O | GLU | 25 | 10.654 | 29.682 | 0.574 | 1.00 | 48.97 | O |
| ATOM | 8 | N | GLU | 25 | 8.564 | 31.353 | 1.814 | 1.00 | 50.30 | N |
| ATOM | 9 | CA | GLU | 25 | 9.389 | 30.323 | 2.511 | 1.00 | 49.61 | C |
| ATOM | 10 | N | THR | 26 | 11.816 | 30.195 | 2.431 | 1.00 | 43.07 | N |
| ATOM | 11 | CA | THR | 26 | 13.119 | 29.941 | 1.824 | 1.00 | 37.71 | C |
| ATOM | 12 | CB | THR | 26 | 14.267 | 30.244 | 2.807 | 1.00 | 38.14 | C |
| ATOM | 13 | OG1 | THR | 26 | 14.227 | 31.628 | 3.174 | 1.00 | 38.51 | O |
| ATOM | 14 | CG2 | THR | 26 | 15.613 | 29.942 | 2.163 | 1.00 | 37.88 | C |
| ATOM | 15 | C | THR | 26 | 13.216 | 28.482 | 1.385 | 1.00 | 34.76 | C |
| ATOM | 16 | O | THR | 26 | 12.823 | 27.579 | 2.120 | 1.00 | 34.28 | O |
| ATOM | 17 | N | LEU | 27 | 13.730 | 28.261 | 0.179 | 1.00 | 29.30 | N |
| ATOM | 18 | CA | LEU | 27 | 13.872 | 26.915 | −0.365 | 1.00 | 28.75 | C |
| ATOM | 19 | CB | LEU | 27 | 13.479 | 26.866 | −1.842 | 1.00 | 28.72 | C |
| ATOM | 20 | CG | LEU | 27 | 12.043 | 27.255 | −2.190 | 1.00 | 29.98 | C |
| ATOM | 21 | CD1 | LEU | 27 | 11.823 | 27.208 | −3.696 | 1.00 | 30.85 | C |
| ATOM | 22 | CD2 | LEU | 27 | 11.037 | 26.358 | −1.482 | 1.00 | 30.07 | C |
| ATOM | 23 | C | LEU | 27 | 15.240 | 26.271 | −0.161 | 1.00 | 26.20 | C |
| ATOM | 24 | O | LEU | 27 | 16.270 | 26.922 | −0.316 | 1.00 | 26.92 | O |
| ATOM | 25 | N | VAL | 28 | 15.234 | 24.989 | 0.196 | 1.00 | 24.29 | N |
| ATOM | 26 | CA | VAL | 28 | 16.465 | 24.230 | 0.402 | 1.00 | 22.04 | C |
| ATOM | 27 | CB | VAL | 28 | 16.566 | 23.684 | 1.845 | 1.00 | 21.66 | C |
| ATOM | 28 | CG1 | VAL | 28 | 16.716 | 24.839 | 2.822 | 1.00 | 20.57 | C |
| ATOM | 29 | CG2 | VAL | 28 | 15.337 | 22.849 | 2.180 | 1.00 | 18.74 | C |
| ATOM | 30 | C | VAL | 28 | 16.549 | 23.066 | −0.585 | 1.00 | 22.51 | C |
| ATOM | 31 | O | VAL | 28 | 15.526 | 22.500 | −0.979 | 1.00 | 20.60 | O |
| ATOM | 32 | N | ARG | 29 | 17.770 | 22.733 | −0.996 | 1.00 | 21.42 | N |
| ATOM | 33 | CA | ARG | 29 | 18.010 | 21.641 | −1.937 | 1.00 | 23.64 | C |
| ATOM | 34 | CB | ARG | 29 | 18.869 | 22.116 | −3.107 | 1.00 | 27.62 | C |
| ATOM | 35 | CG | ARG | 29 | 19.162 | 21.053 | −4.151 | 1.00 | 33.83 | C |
| ATOM | 36 | CD | ARG | 29 | 20.043 | 21.611 | −5.267 | 1.00 | 38.61 | C |
| ATOM | 37 | NE | ARG | 29 | 19.435 | 22.740 | −5.965 | 1.00 | 42.13 | N |
| ATOM | 38 | CZ | ARG | 29 | 18.360 | 22.653 | −6.742 | 1.00 | 45.54 | C |
| ATOM | 39 | NH1 | ARG | 29 | 17.763 | 21.483 | −6.929 | 1.00 | 47.02 | N |
| ATOM | 40 | NH2 | ARG | 29 | 17.882 | 23.740 | −7.337 | 1.00 | 46.93 | N |
| ATOM | 41 | C | ARG | 29 | 18.696 | 20.470 | −1.227 | 1.00 | 20.05 | C |
| ATOM | 42 | O | ARG | 29 | 19.851 | 20.573 | −0.819 | 1.00 | 18.84 | O |
| ATOM | 43 | N | PRO | 30 | 17.988 | 19.343 | −1.078 | 1.00 | 19.58 | N |
| ATOM | 44 | CD | PRO | 30 | 16.511 | 19.312 | −1.031 | 1.00 | 21.57 | C |
| ATOM | 45 | CA | PRO | 30 | 18.498 | 18.137 | −0.425 | 1.00 | 20.02 | C |
| ATOM | 46 | CB | PRO | 30 | 17.278 | 17.234 | −0.444 | 1.00 | 22.34 | C |
| ATOM | 47 | CG | PRO | 30 | 16.234 | 18.184 | 0.016 | 1.00 | 21.93 | C |
| ATOM | 48 | C | PRO | 30 | 19.678 | 17.493 | −1.160 | 1.00 | 19.19 | C |
| ATOM | 49 | O | PRO | 30 | 19.624 | 17.323 | −2.379 | 1.00 | 18.14 | O |
| ATOM | 50 | N | LYS | 31 | 20.737 | 17.144 | −0.433 | 1.00 | 17.57 | N |
| ATOM | 51 | CA | LYS | 31 | 21.870 | 16.450 | −1.044 | 1.00 | 17.54 | C |
| ATOM | 52 | CB | LYS | 31 | 23.083 | 16.416 | −0.110 | 1.00 | 17.17 | C |
| ATOM | 53 | CG | LYS | 31 | 23.588 | 17.814 | 0.242 | 1.00 | 21.31 | C |
| ATOM | 54 | CD | LYS | 31 | 24.792 | 17.784 | 1.175 | 1.00 | 24.34 | C |
| ATOM | 55 | CE | LYS | 31 | 25.250 | 19.198 | 1.499 | 1.00 | 27.70 | C |
| ATOM | 56 | NZ | LYS | 31 | 26.424 | 19.216 | 2.411 | 1.00 | 30.99 | N |
| ATOM | 57 | C | LYS | 31 | 21.367 | 15.049 | −1.436 | 1.00 | 18.76 | C |
| ATOM | 58 | O | LYS | 31 | 20.316 | 14.612 | −0.961 | 1.00 | 17.24 | O |
| ATOM | 59 | N | PRO | 32 | 22.093 | 14.338 | −2.319 | 1.00 | 18.30 | N |

TABLE 3-continued

| 1 | 2 | 3 | 4 | 5 | 6 | 7 | 8 | 9 | 10 | 11 |
|---|---|---|---|---|---|---|---|---|----|----|
| ATOM | 60 | CD | PRO | 32 | 23.329 | 14.791 | −2.991 | 1.00 | 21.43 | C |
| ATOM | 61 | CA | PRO | 32 | 21.764 | 13.000 | −2.820 | 1.00 | 19.62 | C |
| ATOM | 62 | CB | PRO | 32 | 23.111 | 12.503 | −3.293 | 1.00 | 22.05 | C |
| ATOM | 63 | CG | PRO | 32 | 23.536 | 13.680 | −4.080 | 1.00 | 21.40 | C |
| ATOM | 64 | C | PRO | 32 | 21.004 | 11.990 | −1.947 | 1.00 | 19.34 | C |
| ATOM | 65 | O | PRO | 32 | 19.883 | 11.591 | −2.299 | 1.00 | 17.19 | O |
| ATOM | 66 | N | LEU | 33 | 21.594 | 11.559 | −0.833 | 1.00 | 18.45 | N |
| ATOM | 67 | CA | LEU | 33 | 20.911 | 10.581 | 0.017 | 1.00 | 18.88 | C |
| ATOM | 68 | CB | LEU | 33 | 21.788 | 10.020 | 1.142 | 1.00 | 21.73 | C |
| ATOM | 69 | CG | LEU | 33 | 23.050 | 9.209 | 0.871 | 1.00 | 28.04 | C |
| ATOM | 70 | CD1 | LEU | 33 | 24.067 | 9.989 | 0.052 | 1.00 | 29.17 | C |
| ATOM | 71 | CD2 | LEU | 33 | 23.663 | 8.738 | 2.191 | 1.00 | 29.05 | C |
| ATOM | 72 | C | LEU | 33 | 19.597 | 11.062 | 0.602 | 1.00 | 17.92 | C |
| ATOM | 73 | O | LEU | 33 | 18.603 | 10.340 | 0.565 | 1.00 | 16.48 | O |
| ATOM | 74 | N | LEU | 34 | 19.588 | 12.277 | 1.140 | 1.00 | 17.19 | N |
| ATOM | 75 | CA | LEU | 34 | 18.365 | 12.817 | 1.719 | 1.00 | 15.57 | C |
| ATOM | 76 | CB | LEU | 34 | 18.632 | 14.142 | 2.431 | 1.00 | 17.51 | C |
| ATOM | 77 | CG | LEU | 34 | 17.436 | 14.863 | 3.052 | 1.00 | 18.19 | C |
| ATOM | 78 | CD1 | LEU | 34 | 16.656 | 13.966 | 4.007 | 1.00 | 16.62 | C |
| ATOM | 79 | CD2 | LEU | 34 | 17.885 | 16.147 | 3.738 | 1.00 | 16.73 | C |
| ATOM | 80 | C | LEU | 34 | 17.316 | 12.995 | 0.638 | 1.00 | 17.16 | C |
| ATOM | 81 | O | LEU | 34 | 16.128 | 12.769 | 0.870 | 1.00 | 16.85 | O |
| ATOM | 82 | N | LEU | 35 | 17.755 | 13.385 | −0.553 | 1.00 | 15.69 | N |
| ATOM | 83 | CA | LEU | 35 | 16.814 | 13.578 | −1.644 | 1.00 | 18.62 | C |
| ATOM | 84 | CB | LEU | 35 | 17.508 | 14.148 | −2.885 | 1.00 | 20.48 | C |
| ATOM | 85 | CG | LEU | 35 | 16.605 | 14.406 | −4.097 | 1.00 | 23.23 | C |
| ATOM | 86 | CD1 | LEU | 35 | 15.470 | 15.356 | −3.733 | 1.00 | 23.45 | C |
| ATOM | 87 | CD2 | LEU | 35 | 17.389 | 14.944 | −5.293 | 1.00 | 23.24 | C |
| ATOM | 88 | C | LEU | 35 | 16.160 | 12.238 | −1.966 | 1.00 | 19.55 | C |
| ATOM | 89 | O | LEU | 35 | 14.951 | 12.155 | −2.195 | 1.00 | 17.74 | O |
| ATOM | 90 | N | LYS | 36 | 16.964 | 11.181 | −1.955 | 1.00 | 18.27 | N |
| ATOM | 91 | CA | LYS | 36 | 16.453 | 9.859 | −2.271 | 1.00 | 22.37 | C |
| ATOM | 92 | CB | LYS | 36 | 17.610 | 8.864 | −2.413 | 1.00 | 24.10 | C |
| ATOM | 93 | CG | LYS | 36 | 17.212 | 7.444 | −2.785 | 1.00 | 30.65 | C |
| ATOM | 94 | CD | LYS | 36 | 18.461 | 6.576 | −2.920 | 1.00 | 32.62 | C |
| ATOM | 95 | CE | LYS | 36 | 18.128 | 5.145 | −3.307 | 1.00 | 36.89 | C |
| ATOM | 96 | NZ | LYS | 36 | 19.362 | 4.312 | −3.442 | 1.00 | 37.42 | N |
| ATOM | 97 | C | LYS | 36 | 15.413 | 9.413 | −1.246 | 1.00 | 22.40 | C |
| ATOM | 98 | O | LYS | 36 | 14.435 | 8.751 | −1.597 | 1.00 | 22.93 | O |
| ATOM | 99 | N | LEU | 37 | 15.605 | 9.802 | 0.013 | 1.00 | 22.25 | N |
| ATOM | 100 | CA | LEU | 37 | 14.659 | 9.432 | 1.065 | 1.00 | 21.53 | C |
| ATOM | 101 | CB | LEU | 37 | 15.231 | 9.702 | 2.453 | 1.00 | 24.79 | C |
| ATOM | 102 | CG | LEU | 37 | 16.511 | 8.980 | 2.865 | 1.00 | 27.14 | C |
| ATOM | 103 | CD1 | LEU | 37 | 16.996 | 9.454 | 4.226 | 1.00 | 29.28 | C |
| ATOM | 104 | CD2 | LEU | 37 | 16.317 | 7.474 | 2.855 | 1.00 | 29.24 | C |
| ATOM | 105 | C | LEU | 37 | 13.355 | 10.197 | 0.894 | 1.00 | 22.46 | C |
| ATOM | 106 | O | LEU | 37 | 12.269 | 9.636 | 1.053 | 1.00 | 19.80 | O |
| ATOM | 107 | N | LEU | 38 | 13.470 | 11.479 | 0.557 | 1.00 | 21.33 | N |
| ATOM | 108 | CA | LEU | 38 | 12.296 | 12.322 | 0.369 | 1.00 | 21.81 | C |
| ATOM | 109 | CB | LEU | 38 | 12.693 | 13.794 | 0.252 | 1.00 | 22.60 | C |
| ATOM | 110 | CG | LEU | 38 | 13.394 | 14.398 | 1.467 | 1.00 | 23.43 | C |
| ATOM | 111 | CD1 | LEU | 38 | 13.905 | 15.806 | 1.185 | 1.00 | 24.29 | C |
| ATOM | 112 | CD2 | LEU | 38 | 12.491 | 14.362 | 2.685 | 1.00 | 24.94 | C |
| ATOM | 113 | C | LEU | 38 | 11.483 | 11.884 | −0.836 | 1.00 | 24.00 | C |
| ATOM | 114 | O | LEU | 38 | 10.254 | 11.986 | −0.830 | 1.00 | 25.09 | O |
| ATOM | 115 | N | LYS | 39 | 12.160 | 11.381 | −1.865 | 1.00 | 24.12 | N |
| ATOM | 116 | CA | LYS | 39 | 11.442 | 10.928 | −3.045 | 1.00 | 28.66 | C |
| ATOM | 117 | CB | LYS | 39 | 12.339 | 10.855 | −4.282 | 1.00 | 29.59 | C |
| ATOM | 118 | CG | LYS | 39 | 12.939 | 12.179 | −4.728 | 1.00 | 30.58 | C |
| ATOM | 119 | CD | LYS | 39 | 13.798 | 11.969 | −5.968 | 1.00 | 34.21 | C |
| ATOM | 120 | CE | LYS | 39 | 14.414 | 13.266 | −6.459 | 1.00 | 35.99 | C |
| ATOM | 121 | NZ | LYS | 39 | 13.376 | 14.268 | −6.818 | 1.00 | 37.93 | N |
| ATOM | 122 | C | LYS | 39 | 10.766 | 9.588 | −2.803 | 1.00 | 29.02 | C |
| ATOM | 123 | O | LYS | 39 | 9.784 | 9.256 | −3.468 | 1.00 | 30.57 | O |
| ATOM | 124 | N | SER | 40 | 11.270 | 8.823 | −1.839 | 1.00 | 27.39 | N |
| ATOM | 125 | CA | SER | 40 | 10.671 | 7.526 | −1.557 | 1.00 | 27.21 | C |
| ATOM | 126 | CB | SER | 40 | 11.619 | 6.625 | −0.768 | 1.00 | 29.11 | C |
| ATOM | 127 | OG | SER | 40 | 11.934 | 7.200 | 0.484 | 1.00 | 31.61 | O |
| ATOM | 128 | C | SER | 40 | 9.371 | 7.739 | −0.791 | 1.00 | 26.87 | C |
| ATOM | 129 | O | SER | 40 | 8.522 | 6.850 | −0.731 | 1.00 | 24.88 | O |
| ATOM | 130 | N | VAL | 41 | 9.217 | 8.931 | −0.222 | 1.00 | 23.16 | N |
| ATOM | 131 | CA | VAL | 41 | 8.020 | 9.265 | 0.534 | 1.00 | 24.52 | C |
| ATOM | 132 | CB | VAL | 41 | 8.321 | 10.392 | 1.553 | 1.00 | 25.80 | C |
| ATOM | 133 | CG1 | VAL | 41 | 7.053 | 10.879 | 2.197 | 1.00 | 27.99 | C |
| ATOM | 134 | CG2 | VAL | 41 | 9.271 | 9.873 | 2.620 | 1.00 | 25.81 | C |
| ATOM | 135 | C | VAL | 41 | 6.933 | 9.718 | −0.436 | 1.00 | 24.07 | C |
| ATOM | 136 | O | VAL | 41 | 5.750 | 9.780 | −0.083 | 1.00 | 22.91 | O |
| ATOM | 137 | N | GLY | 42 | 7.343 | 10.018 | −1.665 | 1.00 | 23.67 | N |

TABLE 3-continued

| 1 | 2 | 3 | 4 | 5 | 6 | 7 | 8 | 9 | 10 | 11 |
|---|---|---|---|---|---|---|---|---|---|---|
| ATOM | 138 | CA | GLY | 42 | 6.394 | 10.446 | −2.678 | 1.00 | 23.84 | C |
| ATOM | 139 | C | GLY | 42 | 6.685 | 11.764 | −3.373 | 1.00 | 22.51 | C |
| ATOM | 140 | O | GLY | 42 | 6.165 | 12.010 | −4.461 | 1.00 | 21.84 | O |
| ATOM | 141 | N | ALA | 43 | 7.508 | 12.616 | −2.767 | 1.00 | 22.69 | N |
| ATOM | 142 | CA | ALA | 43 | 7.817 | 13.916 | −3.361 | 1.00 | 23.42 | C |
| ATOM | 143 | CB | ALA | 43 | 8.331 | 14.868 | −2.287 | 1.00 | 26.17 | C |
| ATOM | 144 | C | ALA | 43 | 8.830 | 13.811 | −4.497 | 1.00 | 23.99 | C |
| ATOM | 145 | O | ALA | 43 | 9.996 | 13.496 | −4.270 | 1.00 | 23.65 | O |
| ATOM | 146 | N | GLN | 44 | 8.369 | 14.091 | −5.715 | 1.00 | 23.66 | N |
| ATOM | 147 | CA | GLN | 44 | 9.194 | 14.028 | −6.925 | 1.00 | 26.00 | C |
| ATOM | 148 | CB | GLN | 44 | 8.416 | 13.405 | −8.091 | 1.00 | 27.49 | C |
| ATOM | 149 | CG | GLN | 44 | 7.957 | 11.970 | −7.853 | 1.00 | 29.74 | C |
| ATOM | 150 | CD | GLN | 44 | 9.160 | 11.066 | −7.633 | 1.00 | 33.73 | C |
| ATOM | 151 | OE1 | GLN | 44 | 10.295 | 11.436 | −7.932 | 1.00 | 36.21 | O |
| ATOM | 152 | NE2 | GLN | 44 | 8.915 | 9.878 | −7.092 | 1.00 | 35.39 | N |
| ATOM | 153 | C | GLN | 44 | 9.814 | 15.363 | −7.344 | 1.00 | 28.84 | C |
| ATOM | 154 | O | GLN | 44 | 9.895 | 15.669 | −8.532 | 1.00 | 33.20 | O |
| ATOM | 155 | N | LYS | 45 | 10.239 | 16.162 | −6.373 | 1.00 | 26.37 | N |
| ATOM | 156 | CA | LYS | 45 | 10.849 | 17.453 | −6.676 | 1.00 | 26.53 | C |
| ATOM | 157 | CB | LYS | 45 | 9.937 | 18.606 | −6.267 | 1.00 | 26.39 | C |
| ATOM | 158 | CG | LYS | 45 | 9.609 | 18.638 | −4.794 | 1.00 | 26.84 | C |
| ATOM | 159 | CD | LYS | 45 | 8.700 | 19.806 | −4.469 | 1.00 | 28.76 | C |
| ATOM | 160 | CE | LYS | 45 | 8.370 | 19.843 | −2.986 | 1.00 | 27.65 | C |
| ATOM | 161 | NZ | LYS | 45 | 7.477 | 20.988 | −2.669 | 1.00 | 30.55 | N |
| ATOM | 162 | C | LYS | 45 | 12.229 | 17.574 | −6.037 | 1.00 | 25.49 | C |
| ATOM | 163 | O | LYS | 45 | 12.575 | 16.786 | −5.161 | 1.00 | 24.24 | O |
| ATOM | 164 | N | ASP | 46 | 13.020 | 18.548 | −6.480 | 1.00 | 26.71 | N |
| ATOM | 165 | CA | ASP | 46 | 14.360 | 18.726 | −5.925 | 1.00 | 28.66 | C |
| ATOM | 166 | CB | ASP | 46 | 15.403 | 18.827 | −7.040 | 1.00 | 35.21 | C |
| ATOM | 167 | CG | ASP | 46 | 15.144 | 19.991 | −7.980 | 1.00 | 40.54 | C |
| ATOM | 168 | OD1 | ASP | 46 | 14.152 | 20.724 | −7.771 | 1.00 | 42.44 | O |
| ATOM | 169 | OD2 | ASP | 46 | 15.936 | 20.172 | −8.932 | 1.00 | 45.73 | O |
| ATOM | 170 | C | ASP | 46 | 14.534 | 19.865 | −4.913 | 1.00 | 25.87 | C |
| ATOM | 171 | O | ASP | 46 | 15.587 | 19.975 | −4.286 | 1.00 | 24.85 | O |
| ATOM | 172 | N | THR | 47 | 13.513 | 20.703 | −4.747 | 1.00 | 23.77 | N |
| ATOM | 173 | CA | THR | 47 | 13.586 | 21.811 | −3.788 | 1.00 | 23.33 | C |
| ATOM | 174 | CB | THR | 47 | 13.618 | 23.193 | −4.476 | 1.00 | 25.02 | C |
| ATOM | 175 | OG1 | THR | 47 | 12.413 | 23.394 | −5.219 | 1.00 | 27.77 | O |
| ATOM | 176 | CG2 | THR | 47 | 14.814 | 23.291 | −5.398 | 1.00 | 26.67 | C |
| ATOM | 177 | C | THR | 47 | 12.398 | 21.764 | −2.843 | 1.00 | 21.70 | C |
| ATOM | 178 | O | THR | 47 | 11.266 | 21.522 | −3.263 | 1.00 | 21.88 | O |
| ATOM | 179 | N | TYR | 48 | 12.670 | 21.995 | −1.563 | 1.00 | 19.26 | N |
| ATOM | 180 | CA | TYR | 48 | 11.649 | 21.927 | −0.524 | 1.00 | 19.39 | C |
| ATOM | 181 | CB | TYR | 48 | 11.819 | 20.647 | 0.286 | 1.00 | 20.20 | C |
| ATOM | 182 | CG | TYR | 48 | 11.751 | 19.375 | −0.517 | 1.00 | 20.69 | C |
| ATOM | 183 | CD1 | TYR | 48 | 10.643 | 18.539 | −0.433 | 1.00 | 20.32 | C |
| ATOM | 184 | CE1 | TYR | 48 | 10.577 | 17.366 | −1.170 | 1.00 | 23.35 | C |
| ATOM | 185 | CD2 | TYR | 48 | 12.799 | 19.007 | −1.362 | 1.00 | 20.03 | C |
| ATOM | 186 | CE2 | TYR | 48 | 12.744 | 17.836 | −2.107 | 1.00 | 22.54 | C |
| ATOM | 187 | CZ | TYR | 48 | 11.631 | 17.021 | −2.007 | 1.00 | 21.66 | C |
| ATOM | 188 | OH | TYR | 48 | 11.564 | 15.867 | −2.747 | 1.00 | 24.12 | O |
| ATOM | 189 | C | TYR | 48 | 11.761 | 23.093 | 0.444 | 1.00 | 18.48 | C |
| ATOM | 190 | O | TYR | 48 | 12.732 | 23.838 | 0.420 | 1.00 | 18.96 | O |
| ATOM | 191 | N | THR | 49 | 10.747 | 23.246 | 1.286 | 1.00 | 18.95 | N |
| ATOM | 192 | CA | THR | 49 | 10.792 | 24.247 | 2.344 | 1.00 | 19.64 | C |
| ATOM | 193 | CB | THR | 49 | 9.398 | 24.779 | 2.729 | 1.00 | 20.36 | C |
| ATOM | 194 | OG1 | THR | 49 | 8.595 | 23.704 | 3.229 | 1.00 | 18.68 | O |
| ATOM | 195 | CG2 | THR | 49 | 8.720 | 25.421 | 1.531 | 1.00 | 21.70 | C |
| ATOM | 196 | C | THR | 49 | 11.332 | 23.403 | 3.503 | 1.00 | 19.26 | C |
| ATOM | 197 | O | THR | 49 | 11.187 | 22.177 | 3.491 | 1.00 | 16.72 | O |
| ATOM | 198 | N | MET | 50 | 11.971 | 24.033 | 4.482 | 1.00 | 19.49 | N |
| ATOM | 199 | CA | MET | 50 | 12.496 | 23.287 | 5.621 | 1.00 | 19.92 | C |
| ATOM | 200 | CB | MET | 50 | 13.164 | 24.227 | 6.623 | 1.00 | 19.27 | C |
| ATOM | 201 | CG | MET | 50 | 13.752 | 23.549 | 7.857 | 1.00 | 21.93 | C |
| ATOM | 202 | SD | MET | 50 | 15.038 | 22.346 | 7.482 | 1.00 | 22.54 | S |
| ATOM | 203 | CE | MET | 50 | 16.405 | 23.430 | 7.220 | 1.00 | 21.56 | C |
| ATOM | 204 | C | MET | 50 | 11.366 | 22.505 | 6.292 | 1.00 | 20.51 | C |
| ATOM | 205 | O | MET | 50 | 11.556 | 21.358 | 6.717 | 1.00 | 19.62 | O |
| ATOM | 206 | N | LYS | 51 | 10.184 | 23.113 | 6.370 | 1.00 | 20.47 | N |
| ATOM | 207 | CA | LYS | 51 | 9.055 | 22.446 | 7.008 | 1.00 | 21.99 | C |
| ATOM | 208 | CB | LYS | 51 | 7.860 | 23.388 | 7.165 | 1.00 | 26.64 | C |
| ATOM | 209 | CG | LYS | 51 | 6.659 | 22.735 | 7.834 | 1.00 | 33.29 | C |
| ATOM | 210 | CD | LYS | 51 | 5.483 | 23.695 | 7.983 | 1.00 | 38.26 | C |
| ATOM | 211 | CE | LYS | 51 | 4.301 | 23.005 | 8.660 | 1.00 | 40.81 | C |
| ATOM | 212 | NZ | LYS | 51 | 3.128 | 23.912 | 8.828 | 1.00 | 42.40 | N |
| ATOM | 213 | C | LYS | 51 | 8.650 | 21.172 | 6.273 | 1.00 | 19.90 | C |
| ATOM | 214 | O | LYS | 51 | 8.205 | 20.210 | 6.898 | 1.00 | 19.38 | O |
| ATOM | 215 | N | GLU | 52 | 8.817 | 21.149 | 4.953 | 1.00 | 18.87 | N |

TABLE 3-continued

| 1 | 2 | 3 | 4 | 5 | 6 | 7 | 8 | 9 | 10 | 11 |
|---|---|---|---|---|---|---|---|---|---|---|
| ATOM | 216 | CA | GLU | 52 | 8.464 | 19.944 | 4.205 | 1.00 | 17.93 | C |
| ATOM | 217 | CB | GLU | 52 | 8.382 | 20.189 | 2.699 | 1.00 | 18.18 | C |
| ATOM | 218 | CG | GLU | 52 | 7.344 | 21.203 | 2.247 | 1.00 | 23.24 | C |
| ATOM | 219 | CD | GLU | 52 | 7.396 | 21.313 | 0.732 | 1.00 | 25.60 | C |
| ATOM | 220 | OE1 | GLU | 52 | 8.396 | 21.846 | 0.213 | 1.00 | 23.72 | O |
| ATOM | 221 | OE2 | GLU | 52 | 6.438 | 20.874 | 0.057 | 1.00 | 26.89 | O |
| ATOM | 222 | C | GLU | 52 | 9.486 | 18.855 | 4.482 | 1.00 | 15.85 | C |
| ATOM | 223 | O | GLU | 52 | 9.135 | 17.685 | 4.619 | 1.00 | 16.69 | O |
| ATOM | 224 | N | VAL | 53 | 10.753 | 19.250 | 4.568 | 1.00 | 16.93 | N |
| ATOM | 225 | CA | VAL | 53 | 11.825 | 18.293 | 4.825 | 1.00 | 17.04 | C |
| ATOM | 226 | CB | VAL | 53 | 13.203 | 18.995 | 4.855 | 1.00 | 16.03 | C |
| ATOM | 227 | CG1 | VAL | 53 | 14.280 | 18.019 | 5.304 | 1.00 | 16.51 | C |
| ATOM | 228 | CG2 | VAL | 53 | 13.534 | 19.547 | 3.467 | 1.00 | 17.18 | C |
| ATOM | 229 | C | VAL | 53 | 11.596 | 17.602 | 6.166 | 1.00 | 15.46 | C |
| ATOM | 230 | O | VAL | 53 | 11.612 | 16.371 | 6.254 | 1.00 | 15.66 | O |
| ATOM | 231 | N | LEU | 54 | 11.368 | 18.401 | 7.203 | 1.00 | 15.11 | N |
| ATOM | 232 | CA | LEU | 54 | 11.136 | 17.868 | 8.539 | 1.00 | 18.02 | C |
| ATOM | 233 | CB | LEU | 54 | 11.038 | 19.004 | 9.564 | 1.00 | 18.06 | C |
| ATOM | 234 | CG | LEU | 54 | 12.275 | 19.897 | 9.715 | 1.00 | 19.94 | C |
| ATOM | 235 | CD1 | LEU | 54 | 12.017 | 21.075 | 10.651 | 1.00 | 21.06 | C |
| ATOM | 236 | CD2 | LEU | 54 | 13.484 | 19.088 | 10.172 | 1.00 | 19.37 | C |
| ATOM | 237 | C | LEU | 54 | 9.887 | 16.989 | 8.551 | 1.00 | 17.44 | C |
| ATOM | 238 | O | LEU | 54 | 9.890 | 15.901 | 9.132 | 1.00 | 17.96 | O |
| ATOM | 239 | N | TYR | 55 | 8.824 | 17.456 | 7.900 | 1.00 | 19.29 | N |
| ATOM | 240 | CA | TYR | 55 | 7.582 | 16.686 | 7.826 | 1.00 | 19.06 | C |
| ATOM | 241 | CB | TYR | 55 | 6.476 | 17.462 | 7.107 | 1.00 | 21.67 | C |
| ATOM | 242 | CG | TYR | 55 | 5.208 | 16.659 | 6.914 | 1.00 | 24.34 | C |
| ATOM | 243 | CD1 | TYR | 55 | 4.331 | 16.414 | 7.970 | 1.00 | 27.75 | C |
| ATOM | 244 | CE1 | TYR | 55 | 3.185 | 15.626 | 7.788 | 1.00 | 28.11 | C |
| ATOM | 245 | CD2 | TYR | 55 | 4.910 | 16.100 | 5.671 | 1.00 | 26.71 | C |
| ATOM | 246 | CE2 | TYR | 55 | 3.778 | 15.316 | 5.479 | 1.00 | 27.50 | C |
| ATOM | 247 | CZ | TYR | 55 | 2.920 | 15.082 | 6.537 | 1.00 | 29.01 | C |
| ATOM | 248 | OH | TYR | 55 | 1.802 | 14.302 | 6.332 | 1.00 | 31.62 | O |
| ATOM | 249 | C | TYR | 55 | 7.778 | 15.329 | 7.162 | 1.00 | 17.61 | C |
| ATOM | 250 | O | TYR | 55 | 7.450 | 14.295 | 7.742 | 1.00 | 18.75 | O |
| ATOM | 251 | N | TYR | 56 | 8.314 | 15.332 | 5.943 | 1.00 | 17.90 | N |
| ATOM | 252 | CA | TYR | 56 | 8.537 | 14.079 | 5.228 | 1.00 | 15.80 | C |
| ATOM | 253 | CB | TYR | 56 | 8.959 | 14.322 | 3.781 | 1.00 | 16.36 | C |
| ATOM | 254 | CG | TYR | 56 | 7.897 | 14.995 | 2.944 | 1.00 | 19.38 | C |
| ATOM | 255 | CD1 | TYR | 56 | 6.589 | 14.508 | 2.934 | 1.00 | 18.67 | C |
| ATOM | 256 | CE1 | TYR | 56 | 5.610 | 15.083 | 2.132 | 1.00 | 21.66 | C |
| ATOM | 257 | CD2 | TYR | 56 | 8.201 | 16.083 | 2.125 | 1.00 | 19.49 | C |
| ATOM | 258 | CE2 | TYR | 56 | 7.225 | 16.667 | 1.315 | 1.00 | 20.60 | C |
| ATOM | 259 | CZ | TYR | 56 | 5.935 | 16.160 | 1.325 | 1.00 | 22.09 | C |
| ATOM | 260 | OH | TYR | 56 | 4.967 | 16.724 | 0.524 | 1.00 | 24.00 | O |
| ATOM | 261 | C | TYR | 56 | 9.463 | 13.067 | 5.893 | 1.00 | 16.42 | C |
| ATOM | 262 | O | TYR | 56 | 9.247 | 11.863 | 5.759 | 1.00 | 16.20 | O |
| ATOM | 263 | N | LEU | 57 | 10.484 | 13.531 | 6.609 | 1.00 | 17.70 | N |
| ATOM | 264 | CA | LEU | 57 | 11.362 | 12.579 | 7.283 | 1.00 | 18.25 | C |
| ATOM | 265 | CB | LEU | 57 | 12.629 | 13.232 | 7.836 | 1.00 | 22.32 | C |
| ATOM | 266 | CG | LEU | 57 | 13.582 | 13.831 | 6.810 | 1.00 | 26.55 | C |
| ATOM | 267 | CD1 | LEU | 57 | 14.757 | 14.543 | 7.473 | 1.00 | 27.16 | C |
| ATOM | 268 | CD2 | LEU | 57 | 14.073 | 12.746 | 5.861 | 1.00 | 29.77 | C |
| ATOM | 269 | C | LEU | 57 | 10.588 | 11.891 | 8.385 | 1.00 | 18.46 | C |
| ATOM | 270 | O | LEU | 57 | 10.782 | 10.704 | 8.641 | 1.00 | 19.38 | O |
| ATOM | 271 | N | GLY | 58 | 9.693 | 12.639 | 9.023 | 1.00 | 16.71 | N |
| ATOM | 272 | CA | GLY | 58 | 8.883 | 12.060 | 10.077 | 1.00 | 18.09 | C |
| ATOM | 273 | C | GLY | 58 | 7.958 | 11.030 | 9.458 | 1.00 | 18.69 | C |
| ATOM | 274 | O | GLY | 58 | 7.750 | 9.948 | 10.012 | 1.00 | 17.12 | O |
| ATOM | 275 | N | GLN | 59 | 7.402 | 11.370 | 8.297 | 1.00 | 18.56 | N |
| ATOM | 276 | CA | GLN | 59 | 6.494 | 10.470 | 7.585 | 1.00 | 19.64 | C |
| ATOM | 277 | CB | GLN | 59 | 5.787 | 11.209 | 6.448 | 1.00 | 21.81 | C |
| ATOM | 278 | CG | GLN | 59 | 4.918 | 12.363 | 6.913 | 1.00 | 25.45 | C |
| ATOM | 279 | CD | GLN | 59 | 3.842 | 11.829 | 7.830 | 1.00 | 29.94 | C |
| ATOM | 280 | OE1 | GLN | 59 | 3.753 | 12.211 | 9.000 | 1.00 | 32.36 | O |
| ATOM | 281 | NE2 | GLN | 59 | 3.015 | 10.934 | 7.304 | 1.00 | 31.47 | N |
| ATOM | 282 | C | GLN | 59 | 7.212 | 9.228 | 7.062 | 1.00 | 18.28 | C |
| ATOM | 283 | O | GLN | 59 | 6.624 | 8.150 | 6.977 | 1.00 | 18.50 | O |
| ATOM | 284 | N | TYR | 60 | 8.488 | 9.391 | 6.725 | 1.00 | 17.72 | N |
| ATOM | 285 | CA | TYR | 60 | 9.322 | 8.294 | 6.237 | 1.00 | 19.36 | C |
| ATOM | 286 | CB | TYR | 60 | 10.699 | 8.816 | 5.829 | 1.00 | 19.10 | C |
| ATOM | 287 | CG | TYR | 60 | 11.675 | 7.746 | 5.386 | 1.00 | 21.10 | C |
| ATOM | 288 | CD1 | TYR | 60 | 11.634 | 7.221 | 4.095 | 1.00 | 22.00 | C |
| ATOM | 289 | CE1 | TYR | 60 | 12.526 | 6.224 | 3.691 | 1.00 | 20.83 | C |
| ATOM | 290 | CD2 | TYR | 60 | 12.635 | 7.247 | 6.269 | 1.00 | 21.10 | C |
| ATOM | 291 | CE2 | TYR | 60 | 13.532 | 6.245 | 5.876 | 1.00 | 20.35 | C |
| ATOM | 292 | CZ | TYR | 60 | 13.469 | 5.740 | 4.585 | 1.00 | 20.69 | C |
| ATOM | 293 | OH | TYR | 60 | 14.329 | 4.746 | 4.187 | 1.00 | 20.09 | O |

TABLE 3-continued

| 1 | 2 | 3 | 4 | 5 | 6 | 7 | 8 | 9 | 10 | 11 |
|---|---|---|---|---|---|---|---|---|---|---|
| ATOM | 294 | C | TYR | 60 | 9.474 | 7.246 | 7.335 | 1.00 | 19.51 | C |
| ATOM | 295 | O | TYR | 60 | 9.283 | 6.046 | 7.113 | 1.00 | 18.29 | O |
| ATOM | 296 | N | ILE | 61 | 9.812 | 7.722 | 8.527 | 1.00 | 17.99 | N |
| ATOM | 297 | CA | ILE | 61 | 10.012 | 6.851 | 9.675 | 1.00 | 19.08 | C |
| ATOM | 298 | CB | ILE | 61 | 10.521 | 7.687 | 10.878 | 1.00 | 20.08 | C |
| ATOM | 299 | CG2 | ILE | 61 | 10.452 | 6.869 | 12.164 | 1.00 | 20.84 | C |
| ATOM | 300 | CG1 | ILE | 61 | 11.945 | 8.179 | 10.586 | 1.00 | 18.04 | C |
| ATOM | 301 | CD1 | ILE | 61 | 12.547 | 9.033 | 11.670 | 1.00 | 20.08 | C |
| ATOM | 302 | C | ILE | 61 | 8.709 | 6.155 | 10.049 | 1.00 | 20.09 | C |
| ATOM | 303 | O | ILE | 61 | 8.692 | 4.975 | 10.406 | 1.00 | 19.98 | O |
| ATOM | 304 | N | MET | 62 | 7.606 | 6.879 | 9.933 | 1.00 | 20.53 | N |
| ATOM | 305 | CA | MET | 62 | 6.330 | 6.303 | 10.301 | 1.00 | 25.34 | C |
| ATOM | 306 | CB | MET | 62 | 5.305 | 7.398 | 10.599 | 1.00 | 28.26 | C |
| ATOM | 307 | CG | MET | 62 | 3.943 | 6.874 | 11.011 | 1.00 | 34.36 | C |
| ATOM | 308 | SD | MET | 62 | 2.800 | 8.211 | 11.360 | 1.00 | 41.93 | S |
| ATOM | 309 | CE | MET | 62 | 2.064 | 8.447 | 9.727 | 1.00 | 41.20 | C |
| ATOM | 310 | C | MET | 62 | 5.800 | 5.313 | 9.277 | 1.00 | 25.27 | C |
| ATOM | 311 | O | MET | 62 | 5.281 | 4.257 | 9.648 | 1.00 | 24.70 | O |
| ATOM | 312 | N | THR | 63 | 5.951 | 5.635 | 7.997 | 1.00 | 25.57 | N |
| ATOM | 313 | CA | THR | 63 | 5.441 | 4.755 | 6.954 | 1.00 | 28.86 | C |
| ATOM | 314 | CB | THR | 63 | 5.393 | 5.479 | 5.599 | 1.00 | 29.41 | C |
| ATOM | 315 | OG1 | THR | 63 | 4.566 | 6.641 | 5.722 | 1.00 | 33.31 | O |
| ATOM | 316 | CG2 | THR | 63 | 4.809 | 4.574 | 4.526 | 1.00 | 28.44 | C |
| ATOM | 317 | C | THR | 63 | 6.247 | 3.473 | 6.810 | 1.00 | 27.27 | C |
| ATOM | 318 | O | THR | 63 | 5.711 | 2.449 | 6.383 | 1.00 | 27.48 | O |
| ATOM | 319 | N | LYS | 64 | 7.526 | 3.510 | 7.168 | 1.00 | 26.66 | N |
| ATOM | 320 | CA | LYS | 64 | 8.324 | 2.295 | 7.087 | 1.00 | 26.49 | C |
| ATOM | 321 | CB | LYS | 64 | 9.730 | 2.517 | 6.523 | 1.00 | 26.55 | C |
| ATOM | 322 | CG | LYS | 64 | 9.740 | 3.088 | 5.117 | 1.00 | 29.11 | C |
| ATOM | 323 | CD | LYS | 64 | 11.150 | 3.247 | 4.571 | 1.00 | 28.43 | C |
| ATOM | 324 | CE | LYS | 64 | 11.850 | 1.886 | 4.510 | 1.00 | 29.76 | C |
| ATOM | 325 | NZ | LYS | 64 | 13.237 | 1.959 | 3.969 | 1.00 | 29.61 | N |
| ATOM | 326 | C | LYS | 64 | 8.375 | 1.642 | 8.453 | 1.00 | 25.50 | C |
| ATOM | 327 | O | LYS | 64 | 9.026 | 0.617 | 8.639 | 1.00 | 26.13 | O |
| ATOM | 328 | N | ARG | 65 | 7.678 | 2.255 | 9.403 | 1.00 | 24.76 | N |
| ATOM | 329 | CA | ARG | 65 | 7.607 | 1.754 | 10.765 | 1.00 | 25.45 | C |
| ATOM | 330 | CB | ARG | 65 | 6.672 | 0.542 | 10.843 | 1.00 | 31.11 | C |
| ATOM | 331 | CG | ARG | 65 | 5.246 | 0.879 | 10.397 | 1.00 | 35.38 | C |
| ATOM | 332 | CD | ARG | 65 | 4.303 | −0.309 | 10.470 | 1.00 | 41.28 | C |
| ATOM | 333 | NE | ARG | 65 | 2.954 | 0.053 | 10.034 | 1.00 | 46.30 | N |
| ATOM | 334 | CZ | ARG | 65 | 1.897 | −0.754 | 10.104 | 1.00 | 48.44 | C |
| ATOM | 335 | NH1 | ARG | 65 | 2.023 | −1.978 | 10.598 | 1.00 | 49.25 | N |
| ATOM | 336 | NH2 | ARG | 65 | 0.712 | −0.338 | 9.674 | 1.00 | 48.82 | N |
| ATOM | 337 | C | ARG | 65 | 8.979 | 1.472 | 11.378 | 1.00 | 25.07 | C |
| ATOM | 338 | O | ARG | 65 | 9.193 | 0.425 | 11.990 | 1.00 | 23.46 | O |
| ATOM | 339 | N | LEU | 66 | 9.910 | 2.409 | 11.202 | 1.00 | 22.51 | N |
| ATOM | 340 | CA | LEU | 66 | 11.259 | 2.246 | 11.745 | 1.00 | 21.93 | C |
| ATOM | 341 | CB | LEU | 66 | 12.251 | 3.184 | 11.063 | 1.00 | 21.83 | C |
| ATOM | 342 | CG | LEU | 66 | 12.406 | 3.035 | 9.552 | 1.00 | 21.63 | C |
| ATOM | 343 | CD1 | LEU | 66 | 13.391 | 4.062 | 9.015 | 1.00 | 20.95 | C |
| ATOM | 344 | CD2 | LEU | 66 | 12.838 | 1.634 | 9.170 | 1.00 | 20.51 | C |
| ATOM | 345 | C | LEU | 66 | 11.322 | 2.436 | 13.259 | 1.00 | 22.70 | C |
| ATOM | 346 | O | LEU | 66 | 12.325 | 2.115 | 13.893 | 1.00 | 22.69 | O |
| ATOM | 347 | N | TYR | 67 | 10.246 | 2.962 | 13.833 | 1.00 | 23.65 | N |
| ATOM | 348 | CA | TYR | 67 | 10.174 | 3.180 | 15.273 | 1.00 | 23.29 | C |
| ATOM | 349 | CB | TYR | 67 | 9.091 | 4.197 | 15.622 | 1.00 | 24.97 | C |
| ATOM | 350 | CG | TYR | 67 | 7.703 | 3.781 | 15.182 | 1.00 | 25.97 | C |
| ATOM | 351 | CD1 | TYR | 67 | 6.928 | 2.923 | 15.966 | 1.00 | 27.64 | C |
| ATOM | 352 | CE1 | TYR | 67 | 5.656 | 2.522 | 15.554 | 1.00 | 27.94 | C |
| ATOM | 353 | CD2 | TYR | 67 | 7.172 | 4.227 | 13.972 | 1.00 | 27.22 | C |
| ATOM | 354 | CE2 | TYR | 67 | 5.905 | 3.830 | 13.549 | 1.00 | 28.73 | C |
| ATOM | 355 | CZ | TYR | 67 | 5.153 | 2.980 | 14.345 | 1.00 | 29.04 | C |
| ATOM | 356 | OH | TYR | 67 | 3.899 | 2.594 | 13.930 | 1.00 | 29.83 | O |
| ATOM | 357 | C | TYR | 67 | 9.917 | 1.838 | 15.951 | 1.00 | 24.96 | C |
| ATOM | 358 | O | TYR | 67 | 9.215 | 0.992 | 15.404 | 1.00 | 26.17 | O |
| ATOM | 359 | N | ASP | 68 | 10.500 | 1.629 | 17.124 | 1.00 | 25.95 | N |
| ATOM | 360 | CA | ASP | 68 | 10.282 | 0.376 | 17.835 | 1.00 | 28.28 | C |
| ATOM | 361 | CB | ASP | 68 | 11.205 | 0.225 | 19.038 | 1.00 | 31.87 | C |
| ATOM | 362 | CG | ASP | 68 | 10.969 | −1.082 | 19.781 | 1.00 | 35.20 | C |
| ATOM | 363 | OD1 | ASP | 68 | 10.683 | −1.042 | 20.994 | 1.00 | 36.44 | O |
| ATOM | 364 | OD2 | ASP | 68 | 11.061 | −2.149 | 19.141 | 1.00 | 36.99 | O |
| ATOM | 365 | C | ASP | 68 | 8.827 | 0.260 | 18.262 | 1.00 | 28.80 | C |
| ATOM | 366 | O | ASP | 68 | 8.286 | 1.157 | 18.907 | 1.00 | 23.20 | O |
| ATOM | 367 | N | GLU | 69 | 8.200 | −0.851 | 17.898 | 1.00 | 32.27 | N |
| ATOM | 368 | CA | GLU | 69 | 6.799 | −1.073 | 18.224 | 1.00 | 36.70 | C |
| ATOM | 369 | CB | GLU | 69 | 6.336 | −2.428 | 17.684 | 1.00 | 40.26 | C |
| ATOM | 370 | CG | GLU | 69 | 4.873 | −2.762 | 17.936 | 1.00 | 44.82 | C |
| ATOM | 371 | CD | GLU | 69 | 3.981 | −1.727 | 17.266 | 1.00 | 48.03 | C |

TABLE 3-continued

| 1 | 2 | 3 | 4 | 5 | 6 | 7 | 8 | 9 | 10 | 11 |
|---|---|---|---|---|---|---|---|---|---|---|
| ATOM | 372 | OE1 | GLU | 69 | 3.189 | −2.115 | 16.380 | 1.00 | 50.17 | O |
| ATOM | 373 | OE2 | GLU | 69 | 4.064 | −0.532 | 17.621 | 1.00 | 50.09 | O |
| ATOM | 374 | C | GLU | 69 | 6.490 | −0.956 | 19.719 | 1.00 | 36.29 | C |
| ATOM | 375 | O | GLU | 69 | 5.376 | −0.587 | 20.089 | 1.00 | 35.50 | O |
| ATOM | 376 | N | LYS | 70 | 7.471 | −1.245 | 20.574 | 1.00 | 36.45 | N |
| ATOM | 377 | CA | LYS | 70 | 7.246 | −1.173 | 22.018 | 1.00 | 37.74 | C |
| ATOM | 378 | CB | LYS | 70 | 7.591 | −2.501 | 22.694 | 1.00 | 40.70 | C |
| ATOM | 379 | CG | LYS | 70 | 6.766 | −3.677 | 22.186 | 1.00 | 43.93 | C |
| ATOM | 380 | CD | LYS | 70 | 7.137 | −4.979 | 22.889 | 1.00 | 46.97 | C |
| ATOM | 381 | CE | LYS | 70 | 6.298 | −6.143 | 22.369 | 1.00 | 47.54 | C |
| ATOM | 382 | NZ | LYS | 70 | 6.634 | −7.434 | 23.042 | 1.00 | 48.98 | N |
| ATOM | 383 | C | LYS | 70 | 7.928 | −0.005 | 22.730 | 1.00 | 37.66 | C |
| ATOM | 384 | O | LYS | 70 | 7.557 | 0.348 | 23.852 | 1.00 | 39.60 | O |
| ATOM | 385 | N | GLN | 71 | 8.918 | 0.595 | 22.080 | 1.00 | 33.78 | N |
| ATOM | 386 | CA | GLN | 71 | 9.615 | 1.749 | 22.643 | 1.00 | 31.65 | C |
| ATOM | 387 | CB | GLN | 71 | 11.073 | 1.425 | 22.967 | 1.00 | 33.12 | C |
| ATOM | 388 | CG | GLN | 71 | 11.259 | 0.266 | 23.920 | 1.00 | 35.60 | C |
| ATOM | 389 | CD | GLN | 71 | 12.739 | 0.054 | 24.162 | 1.00 | 36.23 | C |
| ATOM | 390 | OE1 | GLN | 71 | 13.361 | −0.811 | 23.548 | 1.00 | 35.70 | O |
| ATOM | 391 | NE2 | GLN | 71 | 13.305 | 0.826 | 25.081 | 1.00 | 35.71 | N |
| ATOM | 392 | C | GLN | 71 | 9.530 | 2.706 | 21.466 | 1.00 | 29.31 | C |
| ATOM | 393 | O | GLN | 71 | 10.488 | 2.864 | 20.713 | 1.00 | 23.70 | O |
| ATOM | 394 | N | GLN | 72 | 8.378 | 3.349 | 21.322 | 1.00 | 27.87 | N |
| ATOM | 395 | CA | GLN | 72 | 8.142 | 4.223 | 20.185 | 1.00 | 29.09 | C |
| ATOM | 396 | CB | GLN | 72 | 6.650 | 4.530 | 20.041 | 1.00 | 32.14 | C |
| ATOM | 397 | CG | GLN | 72 | 5.800 | 3.283 | 19.830 | 1.00 | 35.48 | C |
| ATOM | 398 | CD | GLN | 72 | 4.345 | 3.680 | 19.685 | 1.00 | 37.97 | C |
| ATOM | 399 | OE1 | GLN | 72 | 3.689 | 3.324 | 18.707 | 1.00 | 40.02 | O |
| ATOM | 400 | NE2 | GLN | 72 | 3.836 | 4.431 | 20.654 | 1.00 | 39.88 | N |
| ATOM | 401 | C | GLN | 72 | 8.975 | 5.480 | 20.002 | 1.00 | 27.04 | C |
| ATOM | 402 | O | GLN | 72 | 8.862 | 6.134 | 18.968 | 1.00 | 28.04 | O |
| ATOM | 403 | N | HIS | 73 | 9.814 | 5.823 | 20.973 | 1.00 | 25.52 | N |
| ATOM | 404 | CA | HIS | 73 | 10.638 | 7.017 | 20.817 | 1.00 | 26.50 | C |
| ATOM | 405 | CB | HIS | 73 | 10.876 | 7.728 | 22.155 | 1.00 | 29.45 | C |
| ATOM | 406 | CG | HIS | 73 | 11.649 | 6.914 | 23.147 | 1.00 | 33.08 | C |
| ATOM | 407 | CD2 | HIS | 73 | 11.240 | 6.122 | 24.167 | 1.00 | 34.44 | C |
| ATOM | 408 | ND1 | HIS | 73 | 13.025 | 6.847 | 23.136 | 1.00 | 34.94 | N |
| ATOM | 409 | CE1 | HIS | 73 | 13.432 | 6.048 | 24.109 | 1.00 | 35.16 | C |
| ATOM | 410 | NE2 | HIS | 73 | 12.369 | 5.596 | 24.748 | 1.00 | 34.82 | N |
| ATOM | 411 | C | HIS | 73 | 11.968 | 6.628 | 20.170 | 1.00 | 25.41 | C |
| ATOM | 412 | O | HIS | 73 | 12.763 | 7.494 | 19.797 | 1.00 | 24.29 | O |
| ATOM | 413 | N | ILE | 74 | 12.200 | 5.322 | 20.031 | 1.00 | 22.09 | N |
| ATOM | 414 | CA | ILE | 74 | 13.439 | 4.827 | 19.433 | 1.00 | 19.61 | C |
| ATOM | 415 | CB | ILE | 74 | 13.967 | 3.575 | 20.159 | 1.00 | 19.95 | C |
| ATOM | 416 | CG2 | ILE | 74 | 15.274 | 3.118 | 19.517 | 1.00 | 20.34 | C |
| ATOM | 417 | CG1 | ILE | 74 | 14.185 | 3.888 | 21.640 | 1.00 | 15.63 | C |
| ATOM | 418 | CD1 | ILE | 74 | 14.696 | 2.712 | 22.442 | 1.00 | 20.76 | C |
| ATOM | 419 | C | ILE | 74 | 13.275 | 4.472 | 17.966 | 1.00 | 20.12 | C |
| ATOM | 420 | O | ILE | 74 | 12.440 | 3.642 | 17.593 | 1.00 | 19.78 | O |
| ATOM | 421 | N | VAL | 75 | 14.083 | 5.107 | 17.131 | 1.00 | 18.20 | N |
| ATOM | 422 | CA | VAL | 75 | 14.034 | 4.856 | 15.703 | 1.00 | 17.89 | C |
| ATOM | 423 | CB | VAL | 75 | 14.193 | 6.171 | 14.901 | 1.00 | 17.74 | C |
| ATOM | 424 | CG1 | VAL | 75 | 14.278 | 5.862 | 13.413 | 1.00 | 20.35 | C |
| ATOM | 425 | CG2 | VAL | 75 | 13.025 | 7.106 | 15.185 | 1.00 | 19.50 | C |
| ATOM | 426 | C | VAL | 75 | 15.152 | 3.909 | 15.297 | 1.00 | 18.16 | C |
| ATOM | 427 | O | VAL | 75 | 16.326 | 4.218 | 15.493 | 1.00 | 18.79 | O |
| ATOM | 428 | N | HIS | 76 | 14.788 | 2.754 | 14.745 | 1.00 | 18.90 | N |
| ATOM | 429 | CA | HIS | 76 | 15.775 | 1.785 | 14.271 | 1.00 | 20.21 | C |
| ATOM | 430 | CB | HIS | 76 | 15.334 | 0.332 | 14.487 | 1.00 | 19.35 | C |
| ATOM | 431 | CG | HIS | 76 | 15.229 | −0.064 | 15.924 | 1.00 | 18.87 | C |
| ATOM | 432 | CD2 | HIS | 76 | 14.203 | 0.011 | 16.804 | 1.00 | 20.15 | C |
| ATOM | 433 | ND1 | HIS | 76 | 16.292 | −0.602 | 16.618 | 1.00 | 17.09 | N |
| ATOM | 434 | CE1 | HIS | 76 | 15.924 | −0.841 | 17.864 | 1.00 | 18.81 | C |
| ATOM | 435 | NE2 | HIS | 76 | 14.661 | −0.478 | 18.003 | 1.00 | 18.94 | N |
| ATOM | 436 | C | HIS | 76 | 16.102 | 2.027 | 12.810 | 1.00 | 21.94 | C |
| ATOM | 437 | O | HIS | 76 | 15.285 | 1.781 | 11.923 | 1.00 | 21.85 | O |
| ATOM | 438 | N | CYS | 77 | 17.314 | 2.496 | 12.567 | 1.00 | 19.97 | N |
| ATOM | 439 | CA | CYS | 77 | 17.743 | 2.787 | 11.217 | 1.00 | 22.10 | C |
| ATOM | 440 | CB | CYS | 77 | 17.956 | 4.292 | 11.050 | 1.00 | 21.37 | C |
| ATOM | 441 | SG | CYS | 77 | 19.086 | 4.999 | 12.249 | 1.00 | 23.82 | S |
| ATOM | 442 | C | CYS | 77 | 18.889 | 1.937 | 10.685 | 1.00 | 22.14 | C |
| ATOM | 443 | O | CYS | 77 | 19.434 | 2.212 | 9.619 | 1.00 | 21.97 | O |
| ATOM | 444 | N | SER | 78 | 19.251 | 0.899 | 11.434 | 1.00 | 22.19 | N |
| ATOM | 445 | CA | SER | 78 | 20.304 | −0.010 | 11.000 | 1.00 | 24.97 | C |
| ATOM | 446 | CB | SER | 78 | 20.689 | −1.008 | 12.098 | 1.00 | 24.27 | C |
| ATOM | 447 | OG | SER | 78 | 19.588 | −1.819 | 12.475 | 1.00 | 23.96 | O |
| ATOM | 448 | C | SER | 78 | 19.746 | −0.727 | 9.772 | 1.00 | 27.08 | C |
| ATOM | 449 | O | SER | 78 | 18.578 | −1.098 | 9.752 | 1.00 | 29.90 | O |

TABLE 3-continued

| 1 | 2 | 3 | 4 | 5 | 6 | 7 | 8 | 9 | 10 | 11 |
|---|---|---|---|---|---|---|---|---|---|---|
| ATOM | 450 | N | ASN | 79 | 20.562 | −0.896 | 8.739 | 1.00 | 31.08 | N |
| ATOM | 451 | CA | ASN | 79 | 20.102 | −1.579 | 7.530 | 1.00 | 33.84 | C |
| ATOM | 452 | CB | ASN | 79 | 19.475 | −2.939 | 7.856 | 1.00 | 37.91 | C |
| ATOM | 453 | CG | ASN | 79 | 20.430 | −3.867 | 8.583 | 1.00 | 40.98 | C |
| ATOM | 454 | OD1 | ASN | 79 | 20.087 | −4.436 | 9.623 | 1.00 | 44.02 | O |
| ATOM | 455 | ND2 | ASN | 79 | 21.639 | −4.014 | 8.050 | 1.00 | 41.58 | N |
| ATOM | 456 | C | ASN | 79 | 19.130 | −0.741 | 6.688 | 1.00 | 33.03 | C |
| ATOM | 457 | O | ASN | 79 | 18.500 | −1.260 | 5.765 | 1.00 | 31.20 | O |
| ATOM | 458 | N | ASP | 80 | 18.995 | 0.543 | 7.013 | 1.00 | 28.81 | N |
| ATOM | 459 | CA | ASP | 80 | 18.098 | 1.425 | 6.263 | 1.00 | 24.65 | C |
| ATOM | 460 | CB | ASP | 80 | 16.875 | 1.821 | 7.091 | 1.00 | 23.49 | C |
| ATOM | 461 | CG | ASP | 80 | 15.880 | 2.662 | 6.307 | 1.00 | 24.25 | C |
| ATOM | 462 | OD1 | ASP | 80 | 14.807 | 2.115 | 5.975 | 1.00 | 23.20 | O |
| ATOM | 463 | OD2 | ASP | 80 | 16.143 | 3.855 | 6.033 | 1.00 | 22.88 | O |
| ATOM | 464 | C | ASP | 80 | 18.890 | 2.645 | 5.811 | 1.00 | 24.06 | C |
| ATOM | 465 | O | ASP | 80 | 19.814 | 3.078 | 6.505 | 1.00 | 21.20 | O |
| ATOM | 466 | N | LEU | 81 | 18.546 | 3.188 | 4.647 | 1.00 | 21.17 | N |
| ATOM | 467 | CA | LEU | 81 | 19.257 | 4.354 | 4.131 | 1.00 | 23.85 | C |
| ATOM | 468 | CB | LEU | 81 | 18.638 | 4.843 | 2.819 | 1.00 | 27.45 | C |
| ATOM | 469 | CG | LEU | 81 | 19.280 | 6.057 | 2.138 | 1.00 | 29.98 | C |
| ATOM | 470 | CD1 | LEU | 81 | 20.759 | 5.822 | 1.861 | 1.00 | 32.81 | C |
| ATOM | 471 | CD2 | LEU | 81 | 18.548 | 6.421 | 0.845 | 1.00 | 32.11 | C |
| ATOM | 472 | C | LEU | 81 | 19.313 | 5.486 | 5.155 | 1.00 | 21.14 | C |
| ATOM | 473 | O | LEU | 81 | 20.249 | 6.285 | 5.156 | 1.00 | 18.90 | O |
| ATOM | 474 | N | LEU | 82 | 18.325 | 5.546 | 6.042 | 1.00 | 18.54 | N |
| ATOM | 475 | CA | LEU | 82 | 18.318 | 6.598 | 7.052 | 1.00 | 15.44 | C |
| ATOM | 476 | CB | LEU | 82 | 17.019 | 6.590 | 7.857 | 1.00 | 16.76 | C |
| ATOM | 477 | CG | LEU | 82 | 16.897 | 7.650 | 8.953 | 1.00 | 16.50 | C |
| ATOM | 478 | CD1 | LEU | 82 | 17.090 | 9.052 | 8.382 | 1.00 | 17.63 | C |
| ATOM | 479 | CD2 | LEU | 82 | 15.559 | 7.538 | 9.694 | 1.00 | 17.39 | C |
| ATOM | 480 | C | LEU | 82 | 19.516 | 6.405 | 7.969 | 1.00 | 15.53 | C |
| ATOM | 481 | O | LEU | 82 | 20.070 | 7.373 | 8.495 | 1.00 | 15.91 | O |
| ATOM | 482 | N | GLY | 83 | 19.916 | 5.145 | 8.139 | 1.00 | 14.77 | N |
| ATOM | 483 | CA | GLY | 83 | 21.058 | 4.824 | 8.978 | 1.00 | 16.75 | C |
| ATOM | 484 | C | GLY | 83 | 22.341 | 5.353 | 8.365 | 1.00 | 19.93 | C |
| ATOM | 485 | O | GLY | 83 | 23.236 | 5.824 | 9.075 | 1.00 | 19.30 | O |
| ATOM | 486 | N | ASP | 84 | 22.445 | 5.278 | 7.042 | 1.00 | 20.23 | N |
| ATOM | 487 | CA | ASP | 84 | 23.640 | 5.790 | 6.376 | 1.00 | 19.77 | C |
| ATOM | 488 | CB | ASP | 84 | 23.694 | 5.372 | 4.903 | 1.00 | 22.40 | C |
| ATOM | 489 | CG | ASP | 84 | 23.784 | 3.865 | 4.712 | 1.00 | 24.25 | C |
| ATOM | 490 | OD1 | ASP | 84 | 24.006 | 3.137 | 5.700 | 1.00 | 24.82 | O |
| ATOM | 491 | OD2 | ASP | 84 | 23.627 | 3.407 | 3.562 | 1.00 | 25.98 | O |
| ATOM | 492 | C | ASP | 84 | 23.670 | 7.314 | 6.487 | 1.00 | 20.03 | C |
| ATOM | 493 | O | ASP | 84 | 24.739 | 7.919 | 6.577 | 1.00 | 19.62 | O |
| ATOM | 494 | N | LEU | 85 | 22.488 | 7.925 | 6.511 | 1.00 | 16.11 | N |
| ATOM | 495 | CA | LEU | 85 | 22.385 | 9.377 | 6.578 | 1.00 | 17.87 | C |
| ATOM | 496 | CB | LEU | 85 | 20.972 | 9.827 | 6.194 | 1.00 | 19.94 | C |
| ATOM | 497 | CG | LEU | 85 | 20.673 | 11.320 | 6.099 | 1.00 | 24.54 | C |
| ATOM | 498 | CD1 | LEU | 85 | 21.547 | 11.960 | 5.019 | 1.00 | 24.28 | C |
| ATOM | 499 | CD2 | LEU | 85 | 19.205 | 11.575 | 5.770 | 1.00 | 24.55 | C |
| ATOM | 500 | C | LEU | 85 | 22.779 | 9.897 | 7.965 | 1.00 | 18.33 | C |
| ATOM | 501 | O | LEU | 85 | 23.522 | 10.875 | 8.078 | 1.00 | 18.30 | O |
| ATOM | 502 | N | PHE | 86 | 22.297 | 9.247 | 9.022 | 1.00 | 18.48 | N |
| ATOM | 503 | CA | PHE | 86 | 22.646 | 9.686 | 10.372 | 1.00 | 19.70 | C |
| ATOM | 504 | CB | PHE | 86 | 21.491 | 9.506 | 11.370 | 1.00 | 22.89 | C |
| ATOM | 505 | CG | PHE | 86 | 20.283 | 10.375 | 11.092 | 1.00 | 25.20 | C |
| ATOM | 506 | CD1 | PHE | 86 | 19.282 | 10.504 | 12.051 | 1.00 | 29.11 | C |
| ATOM | 507 | CD2 | PHE | 86 | 20.175 | 11.114 | 9.915 | 1.00 | 26.71 | C |
| ATOM | 508 | CE1 | PHE | 86 | 18.195 | 11.359 | 11.850 | 1.00 | 26.77 | C |
| ATOM | 509 | CE2 | PHE | 86 | 19.091 | 11.972 | 9.702 | 1.00 | 28.12 | C |
| ATOM | 510 | CZ | PHE | 86 | 18.100 | 12.095 | 10.673 | 1.00 | 28.90 | C |
| ATOM | 511 | C | PHE | 86 | 23.943 | 9.104 | 10.927 | 1.00 | 19.63 | C |
| ATOM | 512 | O | PHE | 86 | 24.464 | 9.594 | 11.927 | 1.00 | 21.85 | O |
| ATOM | 513 | N | GLY | 87 | 24.468 | 8.074 | 10.272 | 1.00 | 18.21 | N |
| ATOM | 514 | CA | GLY | 87 | 25.713 | 7.467 | 10.715 | 1.00 | 20.13 | C |
| ATOM | 515 | C | GLY | 87 | 25.620 | 6.699 | 12.021 | 1.00 | 22.27 | C |
| ATOM | 516 | O | GLY | 87 | 26.612 | 6.552 | 12.737 | 1.00 | 21.79 | O |
| ATOM | 517 | N | VAL | 88 | 24.425 | 6.210 | 12.332 | 1.00 | 21.59 | N |
| ATOM | 518 | CA | VAL | 88 | 24.186 | 5.448 | 13.555 | 1.00 | 22.13 | C |
| ATOM | 519 | CB | VAL | 88 | 23.716 | 6.351 | 14.724 | 1.00 | 22.68 | C |
| ATOM | 520 | CG1 | VAL | 88 | 24.830 | 7.306 | 15.130 | 1.00 | 24.59 | C |
| ATOM | 521 | CG2 | VAL | 88 | 22.463 | 7.117 | 14.324 | 1.00 | 23.26 | C |
| ATOM | 522 | C | VAL | 88 | 23.105 | 4.408 | 13.305 | 1.00 | 21.88 | C |
| ATOM | 523 | O | VAL | 88 | 22.271 | 4.576 | 12.417 | 1.00 | 21.47 | O |
| ATOM | 524 | N | PRO | 89 | 23.116 | 3.307 | 14.074 | 1.00 | 22.24 | N |
| ATOM | 525 | CD | PRO | 89 | 23.982 | 2.960 | 15.221 | 1.00 | 23.24 | C |
| ATOM | 526 | CA | PRO | 89 | 22.110 | 2.267 | 13.901 | 1.00 | 20.32 | C |
| ATOM | 527 | CB | PRO | 89 | 22.807 | 1.064 | 14.503 | 1.00 | 23.05 | C |

TABLE 3-continued

| 1 | 2 | 3 | 4 | 5 | 6 | 7 | 8 | 9 | 10 | 11 |
|---|---|---|---|---|---|---|---|---|---|---|
| ATOM | 528 | CG | PRO | 89 | 23.286 | 1.669 | 15.787 | 1.00 | 22.08 | C |
| ATOM | 529 | C | PRO | 89 | 20.770 | 2.609 | 14.559 | 1.00 | 20.59 | C |
| ATOM | 530 | O | PRO | 89 | 19.775 | 1.912 | 14.343 | 1.00 | 21.33 | O |
| ATOM | 531 | N | SER | 90 | 20.743 | 3.688 | 15.341 | 1.00 | 18.62 | N |
| ATOM | 532 | CA | SER | 90 | 19.520 | 4.097 | 16.035 | 1.00 | 17.25 | C |
| ATOM | 533 | CB | SER | 90 | 19.109 | 3.069 | 17.085 | 1.00 | 18.96 | C |
| ATOM | 534 | OG | SER | 90 | 20.118 | 2.972 | 18.080 | 1.00 | 16.15 | O |
| ATOM | 535 | C | SER | 90 | 19.640 | 5.447 | 16.724 | 1.00 | 17.40 | C |
| ATOM | 536 | O | SER | 90 | 20.742 | 5.937 | 16.990 | 1.00 | 17.90 | O |
| ATOM | 537 | N | PHE | 91 | 18.486 | 6.040 | 17.013 | 1.00 | 15.60 | N |
| ATOM | 538 | CA | PHE | 91 | 18.422 | 7.308 | 17.718 | 1.00 | 16.44 | C |
| ATOM | 539 | CB | PHE | 91 | 18.750 | 8.512 | 16.828 | 1.00 | 19.56 | C |
| ATOM | 540 | CG | PHE | 91 | 17.793 | 8.708 | 15.682 | 1.00 | 19.09 | C |
| ATOM | 541 | CD1 | PHE | 91 | 17.923 | 7.972 | 14.512 | 1.00 | 19.65 | C |
| ATOM | 542 | CD2 | PHE | 91 | 16.756 | 9.634 | 15.783 | 1.00 | 21.34 | C |
| ATOM | 543 | CE1 | PHE | 91 | 17.033 | 8.153 | 13.450 | 1.00 | 20.79 | C |
| ATOM | 544 | CE2 | PHE | 91 | 15.858 | 9.824 | 14.728 | 1.00 | 20.20 | C |
| ATOM | 545 | CZ | PHE | 91 | 15.999 | 9.083 | 13.561 | 1.00 | 20.92 | C |
| ATOM | 546 | C | PHE | 91 | 17.043 | 7.491 | 18.334 | 1.00 | 18.30 | C |
| ATOM | 547 | O | PHE | 91 | 16.058 | 6.939 | 17.846 | 1.00 | 17.76 | O |
| ATOM | 548 | N | SER | 92 | 16.992 | 8.248 | 19.422 | 1.00 | 18.06 | N |
| ATOM | 549 | CA | SER | 92 | 15.737 | 8.575 | 20.083 | 1.00 | 20.21 | C |
| ATOM | 550 | CB | SER | 92 | 15.913 | 8.741 | 21.587 | 1.00 | 20.33 | C |
| ATOM | 551 | OG | SER | 92 | 14.676 | 9.099 | 22.181 | 1.00 | 22.41 | O |
| ATOM | 552 | C | SER | 92 | 15.224 | 9.875 | 19.468 | 1.00 | 20.17 | C |
| ATOM | 553 | O | SER | 92 | 16.010 | 10.786 | 19.203 | 1.00 | 19.59 | O |
| ATOM | 554 | N | VAL | 93 | 13.920 | 9.970 | 19.226 | 1.00 | 20.06 | N |
| ATOM | 555 | CA | VAL | 93 | 13.381 | 11.198 | 18.647 | 1.00 | 22.08 | C |
| ATOM | 556 | CB | VAL | 93 | 11.867 | 11.074 | 18.371 | 1.00 | 21.37 | C |
| ATOM | 557 | CG1 | VAL | 93 | 11.608 | 9.904 | 17.429 | 1.00 | 22.86 | C |
| ATOM | 558 | CG2 | VAL | 93 | 11.114 | 10.891 | 19.681 | 1.00 | 22.21 | C |
| ATOM | 559 | C | VAL | 93 | 13.614 | 12.384 | 19.583 | 1.00 | 22.18 | C |
| ATOM | 560 | O | VAL | 93 | 13.425 | 13.538 | 19.197 | 1.00 | 20.43 | O |
| ATOM | 561 | N | LYS | 94 | 14.038 | 12.098 | 20.811 | 1.00 | 24.14 | N |
| ATOM | 562 | CA | LYS | 94 | 14.298 | 13.153 | 21.784 | 1.00 | 25.77 | C |
| ATOM | 563 | CB | LYS | 94 | 14.142 | 12.620 | 23.213 | 1.00 | 30.87 | C |
| ATOM | 564 | CG | LYS | 94 | 15.094 | 11.484 | 23.557 | 1.00 | 36.14 | C |
| ATOM | 565 | CD | LYS | 94 | 14.888 | 10.965 | 24.976 | 1.00 | 40.51 | C |
| ATOM | 566 | CE | LYS | 94 | 13.467 | 10.431 | 25.164 | 1.00 | 42.75 | C |
| ATOM | 567 | NZ | LYS | 94 | 13.224 | 9.907 | 26.539 | 1.00 | 45.31 | N |
| ATOM | 568 | C | LYS | 94 | 15.677 | 13.781 | 21.558 | 1.00 | 24.88 | C |
| ATOM | 569 | O | LYS | 94 | 15.992 | 14.825 | 22.129 | 1.00 | 24.06 | O |
| ATOM | 570 | N | GLU | 95 | 16.488 | 13.144 | 20.715 | 1.00 | 23.25 | N |
| ATOM | 571 | CA | GLU | 95 | 17.823 | 13.653 | 20.393 | 1.00 | 22.14 | C |
| ATOM | 572 | CB | GLU | 95 | 18.761 | 12.526 | 19.940 | 1.00 | 24.17 | C |
| ATOM | 573 | CG | GLU | 95 | 19.031 | 11.470 | 21.011 | 1.00 | 28.59 | C |
| ATOM | 574 | CD | GLU | 95 | 19.963 | 10.399 | 20.463 | 1.00 | 31.12 | C |
| ATOM | 575 | OE1 | GLU | 95 | 21.188 | 10.511 | 20.674 | 1.00 | 33.36 | O |
| ATOM | 576 | OE2 | GLU | 95 | 19.473 | 9.430 | 19.847 | 1.00 | 32.84 | O |
| ATOM | 577 | C | GLU | 95 | 17.733 | 14.757 | 19.346 | 1.00 | 20.96 | C |
| ATOM | 578 | O | GLU | 95 | 18.275 | 14.639 | 18.245 | 1.00 | 18.40 | O |
| ATOM | 579 | N | HIS | 96 | 17.049 | 15.839 | 19.702 | 1.00 | 20.19 | N |
| ATOM | 580 | CA | HIS | 96 | 16.860 | 16.952 | 18.782 | 1.00 | 20.60 | C |
| ATOM | 581 | CB | HIS | 96 | 16.067 | 18.089 | 19.431 | 1.00 | 19.83 | C |
| ATOM | 582 | CG | HIS | 96 | 14.680 | 17.702 | 19.844 | 1.00 | 21.58 | C |
| ATOM | 583 | CD2 | HIS | 96 | 13.987 | 16.552 | 19.675 | 1.00 | 22.20 | C |
| ATOM | 584 | ND1 | HIS | 96 | 13.827 | 18.572 | 20.490 | 1.00 | 24.09 | N |
| ATOM | 585 | CE1 | HIS | 96 | 12.667 | 17.975 | 20.700 | 1.00 | 23.77 | C |
| ATOM | 586 | NE2 | HIS | 96 | 12.737 | 16.748 | 20.215 | 1.00 | 24.59 | N |
| ATOM | 587 | C | HIS | 96 | 18.105 | 17.502 | 18.110 | 1.00 | 19.96 | C |
| ATOM | 588 | O | HIS | 96 | 18.112 | 17.693 | 16.897 | 1.00 | 18.54 | O |
| ATOM | 589 | N | ARG | 97 | 19.163 | 17.750 | 18.873 | 1.00 | 19.16 | N |
| ATOM | 590 | CA | ARG | 97 | 20.343 | 18.309 | 18.241 | 1.00 | 21.59 | C |
| ATOM | 591 | CB | ARG | 97 | 21.402 | 18.733 | 19.254 | 1.00 | 23.22 | C |
| ATOM | 592 | CG | ARG | 97 | 22.605 | 19.332 | 18.560 | 1.00 | 26.59 | C |
| ATOM | 593 | CD | ARG | 97 | 23.697 | 19.791 | 19.503 | 1.00 | 29.57 | C |
| ATOM | 594 | NE | ARG | 97 | 24.804 | 20.353 | 18.733 | 1.00 | 30.13 | N |
| ATOM | 595 | CZ | ARG | 97 | 25.877 | 20.930 | 19.263 | 1.00 | 31.77 | C |
| ATOM | 596 | NH1 | ARG | 97 | 25.998 | 21.028 | 20.581 | 1.00 | 30.89 | N |
| ATOM | 597 | NH2 | ARG | 97 | 26.825 | 21.417 | 18.470 | 1.00 | 30.56 | N |
| ATOM | 598 | C | ARG | 97 | 20.927 | 17.382 | 17.187 | 1.00 | 20.19 | C |
| ATOM | 599 | O | ARG | 97 | 21.341 | 17.836 | 16.124 | 1.00 | 18.40 | O |
| ATOM | 600 | N | LYS | 98 | 20.945 | 16.083 | 17.472 | 1.00 | 20.40 | N |
| ATOM | 601 | CA | LYS | 98 | 21.462 | 15.113 | 16.512 | 1.00 | 22.67 | C |
| ATOM | 602 | CB | LYS | 98 | 21.499 | 13.710 | 17.125 | 1.00 | 25.02 | C |
| ATOM | 603 | CG | LYS | 98 | 21.910 | 12.590 | 16.172 | 1.00 | 28.25 | C |
| ATOM | 604 | CD | LYS | 98 | 23.290 | 12.753 | 15.572 | 1.00 | 32.85 | C |
| ATOM | 605 | CE | LYS | 98 | 23.591 | 11.577 | 14.640 | 1.00 | 35.25 | C |

TABLE 3-continued

| 1 | 2 | 3 | 4 | 5 | 6 | 7 | 8 | 9 | 10 | 11 |
|---|---|---|---|---|---|---|---|---|---|---|
| ATOM | 606 | NZ | LYS | 98 | 24.936 | 11.653 | 13.997 | 1.00 | 38.28 | N |
| ATOM | 607 | C | LYS | 98 | 20.636 | 15.113 | 15.232 | 1.00 | 21.36 | C |
| ATOM | 608 | O | LYS | 98 | 21.177 | 15.067 | 14.124 | 1.00 | 20.55 | O |
| ATOM | 609 | N | ILE | 99 | 19.322 | 15.183 | 15.395 | 1.00 | 17.78 | N |
| ATOM | 610 | CA | ILE | 99 | 18.409 | 15.168 | 14.261 | 1.00 | 16.72 | C |
| ATOM | 611 | CB | ILE | 99 | 16.962 | 15.036 | 14.757 | 1.00 | 18.32 | C |
| ATOM | 612 | CG2 | ILE | 99 | 15.999 | 15.108 | 13.577 | 1.00 | 18.94 | C |
| ATOM | 613 | CG1 | ILE | 99 | 16.813 | 13.713 | 15.522 | 1.00 | 18.48 | C |
| ATOM | 614 | CD1 | ILE | 99 | 15.432 | 13.460 | 16.100 | 1.00 | 20.38 | C |
| ATOM | 615 | C | ILE | 99 | 18.556 | 16.406 | 13.379 | 1.00 | 15.71 | C |
| ATOM | 616 | O | ILE | 99 | 18.745 | 16.289 | 12.166 | 1.00 | 16.59 | O |
| ATOM | 617 | N | TYR | 100 | 18.473 | 17.594 | 13.970 | 1.00 | 16.29 | N |
| ATOM | 618 | CA | TYR | 100 | 18.649 | 18.801 | 13.168 | 1.00 | 15.73 | C |
| ATOM | 619 | CB | TYR | 100 | 18.384 | 20.081 | 13.959 | 1.00 | 17.85 | C |
| ATOM | 620 | CG | TYR | 100 | 16.958 | 20.305 | 14.383 | 1.00 | 18.03 | C |
| ATOM | 621 | CD1 | TYR | 100 | 15.989 | 20.628 | 13.433 | 1.00 | 18.59 | C |
| ATOM | 622 | CE1 | TYR | 100 | 14.686 | 20.920 | 13.805 | 1.00 | 19.33 | C |
| ATOM | 623 | CD2 | TYR | 100 | 16.585 | 20.272 | 15.724 | 1.00 | 19.08 | C |
| ATOM | 624 | CE2 | TYR | 100 | 15.277 | 20.564 | 16.108 | 1.00 | 20.31 | C |
| ATOM | 625 | CZ | TYR | 100 | 14.337 | 20.889 | 15.142 | 1.00 | 20.85 | C |
| ATOM | 626 | OH | TYR | 100 | 13.047 | 21.200 | 15.505 | 1.00 | 20.48 | O |
| ATOM | 627 | C | TYR | 100 | 20.028 | 18.898 | 12.547 | 1.00 | 17.08 | C |
| ATOM | 628 | O | TYR | 100 | 20.177 | 19.362 | 11.417 | 1.00 | 17.10 | O |
| ATOM | 629 | N | THR | 101 | 21.038 | 18.455 | 13.282 | 1.00 | 17.01 | N |
| ATOM | 630 | CA | THR | 101 | 22.395 | 18.547 | 12.771 | 1.00 | 18.10 | C |
| ATOM | 631 | CB | THR | 101 | 23.421 | 18.061 | 13.818 | 1.00 | 19.38 | C |
| ATOM | 632 | OG1 | THR | 101 | 23.409 | 18.950 | 14.944 | 1.00 | 19.40 | O |
| ATOM | 633 | CG2 | THR | 101 | 24.827 | 18.023 | 13.219 | 1.00 | 21.23 | C |
| ATOM | 634 | C | THR | 101 | 22.563 | 17.729 | 11.509 | 1.00 | 17.82 | C |
| ATOM | 635 | O | THR | 101 | 23.123 | 18.207 | 10.523 | 1.00 | 18.96 | O |
| ATOM | 636 | N | MET | 102 | 22.055 | 16.503 | 11.515 | 1.00 | 14.87 | N |
| ATOM | 637 | CA | MET | 102 | 22.241 | 15.673 | 10.345 | 1.00 | 18.86 | C |
| ATOM | 638 | CB | MET | 102 | 22.051 | 14.200 | 10.687 | 1.00 | 22.58 | C |
| ATOM | 639 | CG | MET | 102 | 22.968 | 13.769 | 11.831 | 1.00 | 25.73 | C |
| ATOM | 640 | SD | MET | 102 | 24.729 | 14.046 | 11.491 | 1.00 | 29.72 | S |
| ATOM | 641 | CE | MET | 102 | 25.017 | 12.908 | 10.134 | 1.00 | 26.51 | C |
| ATOM | 642 | C | MET | 102 | 21.366 | 16.115 | 9.181 | 1.00 | 17.36 | C |
| ATOM | 643 | O | MET | 102 | 21.716 | 15.918 | 8.019 | 1.00 | 17.66 | O |
| ATOM | 644 | N | ILE | 103 | 20.242 | 16.746 | 9.488 | 1.00 | 17.10 | N |
| ATOM | 645 | CA | ILE | 103 | 19.360 | 17.217 | 8.432 | 1.00 | 18.31 | C |
| ATOM | 646 | CB | ILE | 103 | 17.971 | 17.598 | 9.004 | 1.00 | 18.43 | C |
| ATOM | 647 | CG2 | ILE | 103 | 17.137 | 18.308 | 7.942 | 1.00 | 19.89 | C |
| ATOM | 648 | CG1 | ILE | 103 | 17.261 | 16.336 | 9.503 | 1.00 | 21.17 | C |
| ATOM | 649 | CD1 | ILE | 103 | 15.895 | 16.591 | 10.129 | 1.00 | 21.70 | C |
| ATOM | 650 | C | ILE | 103 | 19.997 | 18.442 | 7.778 | 1.00 | 18.58 | C |
| ATOM | 651 | O | ILE | 103 | 20.091 | 18.521 | 6.552 | 1.00 | 18.12 | O |
| ATOM | 652 | N | TYR | 104 | 20.461 | 19.384 | 8.598 | 1.00 | 17.58 | N |
| ATOM | 653 | CA | TYR | 104 | 21.063 | 20.600 | 8.065 | 1.00 | 19.92 | C |
| ATOM | 654 | CB | TYR | 104 | 21.408 | 21.597 | 9.171 | 1.00 | 17.24 | C |
| ATOM | 655 | CG | TYR | 104 | 20.245 | 22.073 | 10.015 | 1.00 | 19.35 | C |
| ATOM | 656 | CD1 | TYR | 104 | 18.920 | 21.924 | 9.590 | 1.00 | 17.10 | C |
| ATOM | 657 | CE1 | TYR | 104 | 17.861 | 22.409 | 10.365 | 1.00 | 19.27 | C |
| ATOM | 658 | CD2 | TYR | 104 | 20.479 | 22.714 | 11.227 | 1.00 | 17.95 | C |
| ATOM | 659 | CE2 | TYR | 104 | 19.439 | 23.196 | 12.001 | 1.00 | 19.03 | C |
| ATOM | 660 | CZ | TYR | 104 | 18.137 | 23.044 | 11.571 | 1.00 | 18.59 | C |
| ATOM | 661 | OH | TYR | 104 | 17.125 | 23.531 | 12.363 | 1.00 | 18.75 | O |
| ATOM | 662 | C | TYR | 104 | 22.308 | 20.332 | 7.224 | 1.00 | 18.77 | C |
| ATOM | 663 | O | TYR | 104 | 22.544 | 21.020 | 6.234 | 1.00 | 17.01 | O |
| ATOM | 664 | N | ARG | 105 | 23.095 | 19.332 | 7.608 | 1.00 | 19.90 | N |
| ATOM | 665 | CA | ARG | 105 | 24.303 | 19.019 | 6.850 | 1.00 | 22.21 | C |
| ATOM | 666 | CB | ARG | 105 | 25.252 | 18.112 | 7.634 | 1.00 | 23.00 | C |
| ATOM | 667 | CG | ARG | 105 | 25.786 | 18.721 | 8.916 | 1.00 | 25.04 | C |
| ATOM | 668 | CD | ARG | 105 | 26.724 | 17.753 | 9.616 | 1.00 | 27.11 | C |
| ATOM | 669 | NE | ARG | 105 | 27.269 | 18.306 | 10.853 | 1.00 | 27.31 | N |
| ATOM | 670 | CZ | ARG | 105 | 27.986 | 17.604 | 11.724 | 1.00 | 28.44 | C |
| ATOM | 671 | NH1 | ARG | 105 | 28.241 | 16.324 | 11.488 | 1.00 | 27.73 | N |
| ATOM | 672 | NH2 | ARG | 105 | 28.442 | 18.175 | 12.831 | 1.00 | 28.80 | N |
| ATOM | 673 | C | ARG | 105 | 24.007 | 18.433 | 5.479 | 1.00 | 22.30 | C |
| ATOM | 674 | O | ARG | 105 | 24.893 | 18.333 | 4.632 | 1.00 | 24.22 | O |
| ATOM | 675 | N | ASN | 106 | 22.752 | 18.054 | 5.267 | 1.00 | 20.53 | N |
| ATOM | 676 | CA | ASN | 106 | 22.317 | 17.497 | 3.993 | 1.00 | 21.19 | C |
| ATOM | 677 | CB | ASN | 106 | 21.721 | 16.097 | 4.143 | 1.00 | 19.77 | C |
| ATOM | 678 | CG | ASN | 106 | 22.744 | 15.084 | 4.612 | 1.00 | 22.79 | C |
| ATOM | 679 | OD1 | ASN | 106 | 23.423 | 14.470 | 3.788 | 1.00 | 23.07 | O |
| ATOM | 680 | ND2 | ASN | 106 | 22.843 | 14.879 | 5.924 | 1.00 | 19.66 | N |
| ATOM | 681 | C | ASN | 106 | 21.414 | 18.414 | 3.191 | 1.00 | 20.46 | C |
| ATOM | 682 | O | ASN | 106 | 20.657 | 17.967 | 2.324 | 1.00 | 19.35 | O |
| ATOM | 683 | N | LEU | 107 | 21.510 | 19.703 | 3.497 | 1.00 | 20.37 | N |

TABLE 3-continued

| 1 | 2 | 3 | 4 | 5 | 6 | 7 | 8 | 9 | 10 | 11 |
|---|---|---|---|---|---|---|---|---|---|---|
| ATOM | 684 | CA | LEU | 107 | 20.722 | 20.740 | 2.845 | 1.00 | 22.38 | C |
| ATOM | 685 | CB | LEU | 107 | 19.663 | 21.303 | 3.791 | 1.00 | 21.77 | C |
| ATOM | 686 | CG | LEU | 107 | 18.618 | 20.323 | 4.316 | 1.00 | 23.03 | C |
| ATOM | 687 | CD1 | LEU | 107 | 17.706 | 20.996 | 5.334 | 1.00 | 21.74 | C |
| ATOM | 688 | CD2 | LEU | 107 | 17.816 | 19.716 | 3.169 | 1.00 | 22.14 | C |
| ATOM | 689 | C | LEU | 107 | 21.586 | 21.872 | 2.306 | 1.00 | 23.14 | C |
| ATOM | 690 | O | LEU | 107 | 22.618 | 22.205 | 2.884 | 1.00 | 22.39 | O |
| ATOM | 691 | N | VAL | 108 | 21.158 | 22.445 | 1.189 | 1.00 | 23.48 | N |
| ATOM | 692 | CA | VAL | 108 | 21.846 | 23.569 | 0.566 | 1.00 | 26.51 | C |
| ATOM | 693 | CB | VAL | 108 | 22.484 | 23.158 | −0.776 | 1.00 | 28.25 | C |
| ATOM | 694 | CG1 | VAL | 108 | 23.128 | 24.364 | −1.432 | 1.00 | 31.06 | C |
| ATOM | 695 | CG2 | VAL | 108 | 23.511 | 22.064 | −0.543 | 1.00 | 30.49 | C |
| ATOM | 696 | C | VAL | 108 | 20.795 | 24.647 | 0.304 | 1.00 | 25.74 | C |
| ATOM | 697 | O | VAL | 108 | 19.766 | 24.363 | −0.301 | 1.00 | 24.47 | O |
| ATOM | 698 | N | VAL | 109 | 21.042 | 25.871 | 0.767 | 1.00 | 25.08 | N |
| ATOM | 699 | CA | VAL | 109 | 20.096 | 26.958 | 0.548 | 1.00 | 28.59 | C |
| ATOM | 700 | CB | VAL | 109 | 20.491 | 28.224 | 1.325 | 1.00 | 30.38 | C |
| ATOM | 701 | CG1 | VAL | 109 | 19.457 | 29.320 | 1.088 | 1.00 | 30.40 | C |
| ATOM | 702 | CG2 | VAL | 109 | 20.600 | 27.907 | 2.809 | 1.00 | 30.06 | C |
| ATOM | 703 | C | VAL | 109 | 20.007 | 27.285 | −0.942 | 1.00 | 31.09 | C |
| ATOM | 704 | O | VAL | 109 | 21.017 | 27.538 | −1.600 | 1.00 | 30.68 | O |
| ATOM | 705 | N | VAL | 110 | 18.784 | 27.273 | −1.457 | 1.00 | 34.26 | N |
| ATOM | 706 | CA | VAL | 110 | 18.497 | 27.512 | −2.869 | 1.00 | 40.68 | C |
| ATOM | 707 | CB | VAL | 110 | 17.092 | 26.951 | −3.231 | 1.00 | 41.37 | C |
| ATOM | 708 | CG1 | VAL | 110 | 16.776 | 27.222 | −4.691 | 1.00 | 42.09 | C |
| ATOM | 709 | CG2 | VAL | 110 | 17.046 | 25.456 | −2.948 | 1.00 | 41.30 | C |
| ATOM | 710 | C | VAL | 110 | 18.586 | 28.950 | −3.376 | 1.00 | 45.42 | C |
| ATOM | 711 | O | VAL | 110 | 18.320 | 29.904 | −2.643 | 1.00 | 45.46 | O |
| ATOM | 712 | N | ASN | 111 | 18.980 | 29.063 | −4.644 | 1.00 | 50.62 | N |
| ATOM | 713 | CA | ASN | 111 | 19.090 | 30.319 | −5.380 | 1.00 | 54.41 | C |
| ATOM | 714 | CB | ASN | 111 | 18.454 | 30.130 | −6.764 | 1.00 | 57.01 | C |
| ATOM | 715 | CG | ASN | 111 | 18.469 | 31.386 | −7.600 | 1.00 | 59.53 | C |
| ATOM | 716 | OD1 | ASN | 111 | 17.413 | 31.886 | −7.991 | 1.00 | 60.59 | O |
| ATOM | 717 | ND2 | ASN | 111 | 19.660 | 31.900 | −7.891 | 1.00 | 60.11 | N |
| ATOM | 718 | C | ASN | 111 | 18.521 | 31.547 | −4.662 | 1.00 | 54.78 | C |
| ATOM | 719 | O | ASN | 111 | 17.400 | 31.982 | −4.938 | 1.00 | 56.01 | O |
| ATOM | 720 | C1 | SCH | 996 | −1.000 | 8.674 | 15.423 | 1.00 | 58.94 | |
| ATOM | 721 | C2 | SCH | 996 | 0.074 | 7.820 | 16.068 | 1.00 | 58.85 | |
| ATOM | 722 | O1 | SCH | 996 | −0.100 | 7.261 | 17.153 | 1.00 | 59.47 | |
| ATOM | 723 | N1 | SCH | 996 | 1.202 | 7.745 | 15.337 | 1.00 | 57.09 | |
| ATOM | 724 | C3 | SCH | 996 | 2.471 | 7.578 | 16.042 | 1.00 | 55.53 | |
| ATOM | 725 | C4 | SCH | 996 | 3.102 | 8.922 | 16.429 | 1.00 | 58.30 | |
| ATOM | 726 | O2 | SCH | 996 | 3.020 | 9.892 | 15.673 | 1.00 | 59.95 | |
| ATOM | 727 | N2 | SCH | 996 | 3.724 | 8.908 | 17.631 | 1.00 | 61.62 | |
| ATOM | 728 | C5 | SCH | 996 | 4.020 | 10.154 | 18.329 | 1.00 | 63.29 | |
| ATOM | 729 | C6 | SCH | 996 | 2.706 | 10.796 | 18.790 | 1.00 | 65.39 | |
| ATOM | 730 | O3 | SCH | 996 | 2.516 | 12.011 | 18.716 | 1.00 | 65.59 | |
| ATOM | 731 | N3 | SCH | 996 | 1.822 | 9.901 | 19.269 | 1.00 | 67.92 | |
| ATOM | 732 | C7 | SCH | 996 | 0.554 | 10.407 | 19.793 | 1.00 | 70.11 | |
| ATOM | 733 | C8 | SCH | 996 | 0.346 | 9.699 | 20.930 | 1.00 | 70.97 | |
| ATOM | 734 | O4 | SCH | 996 | 0.223 | 10.153 | 22.077 | 1.00 | 71.51 | |
| ATOM | 735 | O5 | SCH | 996 | 0.325 | 8.321 | 20.830 | 1.00 | 71.56 | |
| ATOM | 736 | C9 | SCH | 996 | 3.406 | 6.688 | 15.192 | 1.00 | 49.97 | |
| ATOM | 737 | C10 | SCH | 996 | −0.504 | 10.428 | 18.687 | 1.00 | 70.56 | |
| ATOM | 738 | C11 | SCH | 996 | −0.315 | 11.537 | 17.664 | 1.00 | 71.51 | |
| ATOM | 739 | C12 | SCH | 996 | −1.305 | 12.653 | 17.941 | 1.00 | 72.44 | |
| ATOM | 740 | O6 | SCH | 996 | −0.991 | 13.651 | 18.515 | 1.00 | 72.59 | |
| ATOM | 741 | O7 | SCH | 996 | −2.556 | 12.416 | 17.482 | 1.00 | 72.61 | |
| ATOM | 742 | C13 | SCH | 996 | 4.852 | 6.796 | 15.638 | 1.00 | 44.76 | |
| ATOM | 743 | C14 | SCH | 996 | 5.890 | 7.608 | 15.051 | 1.00 | 41.72 | |
| ATOM | 744 | C15 | SCH | 996 | 7.096 | 7.390 | 15.825 | 1.00 | 40.91 | |
| ATOM | 745 | N4 | SCH | 996 | 6.776 | 6.472 | 16.833 | 1.00 | 40.79 | |
| ATOM | 746 | C16 | SCH | 996 | 5.458 | 6.131 | 16.715 | 1.00 | 43.06 | |
| ATOM | 747 | C17 | SCH | 996 | 5.912 | 8.510 | 13.946 | 1.00 | 40.02 | |
| ATOM | 748 | C18 | SCH | 996 | 7.115 | 9.193 | 13.606 | 1.00 | 37.25 | |
| ATOM | 749 | C19 | SCH | 996 | 8.298 | 8.983 | 14.370 | 1.00 | 36.32 | |
| ATOM | 750 | C20 | SCH | 996 | 8.295 | 8.082 | 15.474 | 1.00 | 37.47 | |
| ATOM | 751 | CL1 | SCH | 996 | 9.737 | 9.840 | 13.965 | 1.00 | 29.32 | |
| ATOM | 752 | C21 | SCH | 996 | 4.747 | 11.137 | 17.396 | 1.00 | 62.87 | |
| ATOM | 753 | C22 | SCH | 996 | 4.877 | 9.854 | 19.566 | 1.00 | 62.94 | |
| ATOM | 754 | C23 | SCH | 996 | 6.279 | 9.364 | 19.188 | 1.00 | 62.44 | |
| ATOM | 755 | C24 | SCH | 996 | 6.166 | 10.673 | 17.043 | 1.00 | 62.33 | |
| ATOM | 756 | C25 | SCH | 996 | 7.006 | 10.356 | 18.280 | 1.00 | 62.08 | |
| ATOM | 757 | C1 | SCH | 998 | 7.020 | 14.306 | 19.529 | 1.00 | 32.04 | |
| ATOM | 758 | C2 | SCH | 998 | 8.132 | 14.220 | 18.499 | 1.00 | 30.99 | |
| ATOM | 759 | O1 | SCH | 998 | 9.294 | 13.953 | 18.813 | 1.00 | 31.33 | |
| ATOM | 760 | N1 | SCH | 998 | 7.711 | 14.463 | 17.243 | 1.00 | 28.90 | |
| ATOM | 761 | C3 | SCH | 998 | 8.715 | 14.626 | 16.190 | 1.00 | 28.20 | |

TABLE 3-continued

| 1 | 2 | 3 | 4 | 5 | 6 | 7 | 8 | 9 | 10 | 11 |
|---|---|---|---|---|---|---|---|---|---|---|
| ATOM | 762 | C4 | SCH | 998 | 9.050 | 16.095 | 15.923 | 1.00 | 28.60 | |
| ATOM | 763 | O2 | SCH | 998 | 8.184 | 16.880 | 15.527 | 1.00 | 28.06 | |
| ATOM | 764 | N2 | SCH | 998 | 10.342 | 16.402 | 16.159 | 1.00 | 26.21 | |
| ATOM | 765 | C5 | SCH | 998 | 10.807 | 17.775 | 16.036 | 1.00 | 28.33 | |
| ATOM | 766 | C6 | SCH | 998 | 9.978 | 18.673 | 16.963 | 1.00 | 33.18 | |
| ATOM | 767 | O3 | SCH | 998 | 9.634 | 19.808 | 16.630 | 1.00 | 35.64 | |
| ATOM | 768 | N3 | SCH | 998 | 9.686 | 18.088 | 18.140 | 1.00 | 37.61 | |
| ATOM | 769 | C7 | SCH | 998 | 8.697 | 18.731 | 19.006 | 1.00 | 42.54 | |
| ATOM | 770 | C8 | SCH | 998 | 9.245 | 18.545 | 20.404 | 1.00 | 42.96 | |
| ATOM | 771 | O4 | SCH | 998 | 9.535 | 19.446 | 21.049 | 1.00 | 44.48 | |
| ATOM | 772 | O5 | SCH | 998 | 9.382 | 17.262 | 20.693 | 1.00 | 43.12 | |
| ATOM | 773 | C9 | SCH | 998 | 8.244 | 13.892 | 14.923 | 1.00 | 27.77 | |
| ATOM | 774 | C10 | SCH | 998 | 7.290 | 18.240 | 18.661 | 1.00 | 44.92 | |
| ATOM | 775 | C11 | SCH | 998 | 6.730 | 18.812 | 17.368 | 1.00 | 48.30 | |
| ATOM | 776 | C12 | SCH | 998 | 5.583 | 19.752 | 17.684 | 1.00 | 49.87 | |
| ATOM | 777 | O6 | SCH | 998 | 5.601 | 20.902 | 17.365 | 1.00 | 51.11 | |
| ATOM | 778 | O7 | SCH | 998 | 4.554 | 19.175 | 18.348 | 1.00 | 50.51 | |
| ATOM | 779 | C13 | SCH | 998 | 9.158 | 14.149 | 13.740 | 1.00 | 25.37 | |
| ATOM | 780 | C14 | SCH | 998 | 10.480 | 13.618 | 13.499 | 1.00 | 25.02 | |
| ATOM | 781 | C15 | SCH | 998 | 10.902 | 14.099 | 12.199 | 1.00 | 25.73 | |
| ATOM | 782 | N4 | SCH | 998 | 9.868 | 14.895 | 11.699 | 1.00 | 25.53 | |
| ATOM | 783 | C16 | SCH | 998 | 8.852 | 14.918 | 12.609 | 1.00 | 25.55 | |
| ATOM | 784 | C17 | SCH | 998 | 11.350 | 12.777 | 14.254 | 1.00 | 25.02 | |
| ATOM | 785 | C18 | SCH | 998 | 12.617 | 12.399 | 13.724 | 1.00 | 25.30 | |
| ATOM | 786 | C19 | SCH | 998 | 13.020 | 12.858 | 12.437 | 1.00 | 26.55 | |
| ATOM | 787 | C20 | SCH | 998 | 12.171 | 13.711 | 11.677 | 1.00 | 24.81 | |
| ATOM | 788 | CL1 | SCH | 998 | 14.529 | 12.355 | 11.778 | 1.00 | 26.71 | |
| ATOM | 789 | C21 | SCH | 998 | 10.639 | 18.264 | 14.593 | 1.00 | 26.42 | |
| ATOM | 790 | C22 | SCH | 998 | 12.279 | 17.852 | 16.457 | 1.00 | 26.82 | |
| ATOM | 791 | C23 | SCH | 998 | 13.181 | 17.061 | 15.496 | 1.00 | 25.79 | |
| ATOM | 792 | C24 | SCH | 998 | 11.554 | 17.510 | 13.617 | 1.00 | 24.84 | |
| ATOM | 793 | C25 | SCH | 998 | 13.025 | 17.532 | 14.048 | 1.00 | 24.21 | |
| ATOM | 794 | C1 | SCH | 999 | 14.304 | 27.533 | 13.501 | 1.00 | 20.77 | |
| ATOM | 795 | C2 | SCH | 999 | 14.911 | 27.965 | 12.179 | 1.00 | 20.52 | |
| ATOM | 796 | O1 | SCH | 999 | 14.277 | 28.618 | 11.350 | 1.00 | 21.90 | |
| ATOM | 797 | N1 | SCH | 999 | 16.183 | 27.557 | 12.024 | 1.00 | 19.32 | |
| ATOM | 798 | C3 | SCH | 999 | 16.883 | 27.892 | 10.787 | 1.00 | 20.88 | |
| ATOM | 799 | C4 | SCH | 999 | 16.080 | 27.517 | 9.526 | 1.00 | 22.08 | |
| ATOM | 800 | O2 | SCH | 999 | 15.657 | 26.372 | 9.370 | 1.00 | 21.93 | |
| ATOM | 801 | N2 | SCH | 999 | 15.894 | 28.551 | 8.669 | 1.00 | 22.51 | |
| ATOM | 802 | C5 | SCH | 999 | 15.213 | 28.377 | 7.382 | 1.00 | 24.88 | |
| ATOM | 803 | C6 | SCH | 999 | 13.709 | 28.188 | 7.602 | 1.00 | 26.16 | |
| ATOM | 804 | O3 | SCH | 999 | 12.953 | 27.935 | 6.665 | 1.00 | 27.24 | |
| ATOM | 805 | N3 | SCH | 999 | 13.318 | 28.331 | 8.879 | 1.00 | 27.90 | |
| ATOM | 806 | C7 | SCH | 999 | 11.886 | 28.201 | 9.143 | 1.00 | 31.35 | |
| ATOM | 807 | C8 | SCH | 999 | 11.241 | 29.583 | 9.052 | 1.00 | 34.43 | |
| ATOM | 808 | O4 | SCH | 999 | 10.006 | 29.558 | 9.037 | 1.00 | 35.86 | |
| ATOM | 809 | O5 | SCH | 999 | 11.994 | 30.531 | 8.919 | 1.00 | 36.30 | |
| ATOM | 810 | C9 | SCH | 999 | 18.277 | 27.245 | 10.824 | 1.00 | 20.43 | |
| ATOM | 811 | C10 | SCH | 999 | 11.653 | 27.295 | 10.349 | 1.00 | 31.35 | |
| ATOM | 812 | C11 | SCH | 999 | 12.066 | 25.844 | 10.129 | 1.00 | 29.83 | |
| ATOM | 813 | C12 | SCH | 999 | 11.716 | 25.026 | 11.360 | 1.00 | 32.05 | |
| ATOM | 814 | O6 | SCH | 999 | 12.531 | 24.381 | 11.942 | 1.00 | 31.48 | |
| ATOM | 815 | O7 | SCH | 999 | 10.416 | 25.092 | 11.730 | 1.00 | 32.95 | |
| ATOM | 816 | C13 | SCH | 999 | 19.093 | 27.591 | 9.595 | 1.00 | 21.99 | |
| ATOM | 817 | C14 | SCH | 999 | 19.603 | 26.675 | 8.606 | 1.00 | 21.11 | |
| ATOM | 818 | C15 | SCH | 999 | 20.326 | 27.456 | 7.626 | 1.00 | 22.79 | |
| ATOM | 819 | N4 | SCH | 999 | 20.243 | 28.793 | 8.029 | 1.00 | 23.21 | |
| ATOM | 820 | C16 | SCH | 999 | 19.518 | 28.863 | 9.184 | 1.00 | 22.90 | |
| ATOM | 821 | C17 | SCH | 999 | 19.512 | 25.260 | 8.455 | 1.00 | 21.66 | |
| ATOM | 822 | C18 | SCH | 999 | 20.126 | 24.621 | 7.341 | 1.00 | 23.05 | |
| ATOM | 823 | C19 | SCH | 999 | 20.833 | 25.388 | 6.371 | 1.00 | 22.06 | |
| ATOM | 824 | C20 | SCH | 999 | 20.937 | 26.803 | 6.511 | 1.00 | 22.85 | |
| ATOM | 825 | CL1 | SCH | 999 | 21.550 | 24.594 | 5.014 | 1.00 | 26.59 | |
| ATOM | 826 | C21 | SCH | 999 | 15.747 | 27.140 | 6.639 | 1.00 | 23.66 | |
| ATOM | 827 | C22 | SCH | 999 | 15.409 | 29.639 | 6.533 | 1.00 | 24.90 | |
| ATOM | 828 | C23 | SCH | 999 | 16.867 | 29.820 | 6.129 | 1.00 | 24.75 | |
| ATOM | 829 | C24 | SCH | 999 | 17.176 | 27.321 | 6.103 | 1.00 | 23.22 | |
| ATOM | 830 | C25 | SCH | 999 | 17.379 | 28.625 | 5.329 | 1.00 | 23.88 | |
| ATOM | 831 | OH2 | WAT | 1001 | 3.395 | 9.112 | −1.435 | 1.00 | 16.59 | O |
| ATOM | 839 | OH2 | WAT | 1002 | 24.775 | 12.618 | 6.376 | 1.00 | 17.52 | O |
| ATOM | 832 | OH2 | WAT | 1003 | 18.514 | −0.561 | 14.622 | 1.00 | 18.25 | O |
| ATOM | 835 | OH2 | WAT | 1004 | 15.044 | 24.301 | 11.181 | 1.00 | 18.80 | O |
| ATOM | 856 | OH2 | WAT | 1005 | 20.867 | 15.283 | 20.436 | 1.00 | 24.20 | O |
| ATOM | 842 | OH2 | WAT | 1006 | 9.724 | 26.049 | 6.031 | 1.00 | 24.72 | O |
| ATOM | 860 | OH2 | WAT | 1007 | 6.074 | 13.931 | 10.197 | 1.00 | 24.81 | O |
| ATOM | 857 | OH2 | WAT | 1008 | 21.757 | 8.195 | 18.608 | 1.00 | 25.80 | O |
| ATOM | 833 | OH2 | WAT | 1009 | 12.107 | 26.746 | 4.500 | 1.00 | 25.85 | O |

TABLE 3-continued

| 1 | 2 | 3 | 4 | 5 | 6 | 7 | 8 | 9 | 10 | 11 |
|---|---|---|---|---|---|---|---|---|---|---|
| ATOM | 843 | OH2 | WAT | 1010 | 16.620 | 1.807 | 2.942 | 1.00 | 26.33 | O |
| ATOM | 870 | OH2 | WAT | 1011 | 7.466 | 20.307 | 9.569 | 1.00 | 26.55 | O |
| ATOM | 848 | OH2 | WAT | 1012 | 11.574 | 22.642 | 13.779 | 1.00 | 26.80 | O |
| ATOM | 834 | OH2 | WAT | 1013 | 13.759 | −1.012 | 20.605 | 1.00 | 28.49 | O |
| ATOM | 840 | OH2 | WAT | 1014 | 25.743 | 20.101 | 15.817 | 1.00 | 28.57 | O |
| ATOM | 855 | OH2 | WAT | 1015 | 0.544 | 11.546 | 5.002 | 1.00 | 29.35 | O |
| ATOM | 844 | OH2 | WAT | 1016 | 21.356 | 8.460 | 22.469 | 1.00 | 30.69 | O |
| ATOM | 836 | OH2 | WAT | 1017 | 14.502 | −0.707 | 6.212 | 1.00 | 31.40 | O |
| ATOM | 841 | OH2 | WAT | 1018 | 11.775 | 14.532 | 17.517 | 1.00 | 31.42 | O |
| ATOM | 851 | OH2 | WAT | 1019 | 22.475 | 1.722 | 7.609 | 1.00 | 31.99 | O |
| ATOM | 859 | OH2 | WAT | 1020 | 5.732 | 18.551 | −1.162 | 1.00 | 32.12 | O |
| ATOM | 872 | OH2 | WAT | 1021 | 23.725 | 20.929 | 22.606 | 1.00 | 34.79 | O |
| ATOM | 862 | OH2 | WAT | 1022 | 23.860 | 26.433 | 1.644 | 1.00 | 34.96 | O |
| ATOM | 863 | OH2 | WAT | 1023 | 5.394 | 16.356 | 11.571 | 1.00 | 35.71 | O |
| ATOM | 861 | OH2 | WAT | 1024 | 21.332 | 30.796 | 5.811 | 1.00 | 36.70 | O |
| ATOM | 847 | OH2 | WAT | 1025 | 9.148 | −2.863 | 15.900 | 1.00 | 37.64 | O |
| ATOM | 858 | OH2 | WAT | 1026 | 14.166 | 16.525 | 23.729 | 1.00 | 37.84 | O |
| ATOM | 866 | OH2 | WAT | 1027 | 11.334 | 30.280 | 5.618 | 1.00 | 38.35 | O |
| ATOM | 864 | OH2 | WAT | 1028 | 18.007 | 18.195 | −4.362 | 1.00 | 40.37 | O |
| ATOM | 871 | OH2 | WAT | 1029 | 11.860 | 21.767 | 17.854 | 1.00 | 40.71 | O |
| ATOM | 874 | OH2 | WAT | 1030 | 8.276 | 27.446 | 8.045 | 1.00 | 41.07 | O |
| ATOM | 846 | OH2 | WAT | 1031 | 7.632 | 18.152 | 11.360 | 1.00 | 42.63 | O |
| ATOM | 865 | OH2 | WAT | 1032 | 25.898 | 10.512 | 16.626 | 1.00 | 43.37 | O |
| ATOM | 854 | OH2 | WAT | 1033 | 8.159 | −1.042 | 14.070 | 1.00 | 44.00 | O |
| ATOM | 852 | OH2 | WAT | 1034 | 28.464 | 14.740 | 9.077 | 1.00 | 46.88 | O |
| ATOM | 845 | OH2 | WAT | 1035 | 2.078 | 6.181 | 4.658 | 1.00 | 47.60 | O |
| ATOM | 838 | OH2 | WAT | 1036 | 26.484 | 15.271 | 4.182 | 1.00 | 47.99 | O |
| ATOM | 867 | OH2 | WAT | 1037 | 23.657 | 28.439 | −1.144 | 1.00 | 50.33 | O |
| ATOM | 837 | OH2 | WAT | 1038 | 13.538 | 21.361 | 20.180 | 1.00 | 54.13 | O |
| ATOM | 869 | OH2 | WAT | 1039 | 25.590 | 16.309 | 16.444 | 1.00 | 54.19 | O |
| ATOM | 850 | OH2 | WAT | 1040 | 26.845 | 13.685 | 16.859 | 1.00 | 55.86 | O |
| ATOM | 873 | OH2 | WAT | 1041 | 27.978 | 4.166 | 14.080 | 1.00 | 55.87 | O |
| ATOM | 868 | OH2 | WAT | 1042 | 20.489 | 1.898 | −2.662 | 1.00 | 56.16 | O |
| ATOM | 853 | OH2 | WAT | 1043 | 17.178 | 10.875 | −6.741 | 1.00 | 59.20 | O |
| ATOM | 849 | OH2 | WAT | 1044 | 25.481 | 2.906 | 8.796 | 1.00 | 63.46 | O |
| END | | | | | | | | | | |

Example 3

Preparation and Crystallization of Hdm2 Y76H-Tripeptide Complex

Production and Crystallization of Modified Hdm2(Y76H):

The modified Hdm2(Y76H) protein was produced using the QuickChange site-directed mutagenesis method as discussed in Example 1 except that only the primers for Y76H were used in mutagenesis. The p53 peptide analog, Ac-$^{6Cl}$WAC$_{3c}$E, disclosed and defined above, was dissolved in the same buffer and added to the Hdm2(Y76H) protein solution.

The single mutant HDM2 (17-125) Y76H-tripeptide complex was crystallized using a hanging-drop vapor diffusion method. The protein-peptide solution (1 µl; 6-10 mg/ml) in buffer A was mixed with an equal volume of precipitant [0.1 M Tris, pH 8-9, 35% PEG 4000, and 0.0 to 0.2 M magnesium chloride], placed on the underside of a siliconized glass coverslip and sealed in close proximity to 1 ml of the precipitant solution. Vapor diffusion crystallization experiments were conducted using the hanging drop method. Specifically, crystals were grown from a droplet containing a mixture of 0.5-2.0 µl of protein and 0.5-1.0 µl of the precipitant solution. Crystallization plates were incubated at 4° C.; rectangular rod crystals (0.1×0.1×0.3 mm) grew over 2-30 days.

Prior to data collection, crystals were washed with the reservoir solution of the crystallization setup and transferred into the same solution with 10% glycerol added. The crystals were then flash-cooled in a nitrogen stream at 95 K. X-ray diffraction was collected using a Riga generator equipped with a Praxis 4++ detector. Data were integrated and scaled using the HKL package.

Data Collection Statistics:

| | |
|---|---|
| Resolution | 50.0-.20 Å |
| No. of collected reflections | 13234 |
| No. of unique reflections (F >= 0) | 4341 |
| R-sym | 6.2% |
| Percent of theoretical (I/s >= 1) | 84.8% |
| Unit Cell | a = 41.1 Å, b = 42.7 Å, c = 53.777 Å, α = β = γ = 90° |
| Space Group | P2$_1$2$_1$2$_1$ |
| Asymmetric unit | 1 molecule |

The crystal structure was solved using molecular replacement using the search models 1YCQ and 1YCR from the PDB. Refinement was done using the program CNX.

| | |
|---|---|
| Theoretical number of reflections | 5854 |
| Resolution Limits | 50.0-2.1 Å |
| Number of unobserved reflections | 1529 (26.1%) |
| Number of reflections in working set | 4325 (73.9%) |
| Number of reflections in test set | 197 (3.4%) |
| Number of protein residues | 87 |
| Number of solvent atoms | 0 |
| R-factor | 0.45 |
| R-free | 0.51 |
| RMSD bond length | 0.014 Å |
| RMSD bond angles | 1.97° |

The structural coordinates for the above-described Hdm2 crystal are set forth below in Table 4.

TABLE 4

| 1 | 2 | 3 | 4 | 5 | 6 | 7 | 8 | 9 | 10 | 11 |
|---|---|---|---|---|---|---|---|---|---|---|
| ATOM | 1 | CB | GLU | 25 | 7.387 | −0.822 | 5.902 | 1.00 | 31.40 | C |
| ATOM | 2 | CG | GLU | 25 | 7.019 | −0.298 | 4.509 | 1.00 | 35.01 | C |
| ATOM | 3 | CD | GLU | 25 | 7.873 | −0.972 | 3.442 | 1.00 | 37.01 | C |
| ATOM | 4 | OE1 | GLU | 25 | 7.321 | −1.714 | 2.600 | 1.00 | 35.86 | O |
| ATOM | 5 | OE2 | GLU | 25 | 9.101 | −0.744 | 3.437 | 1.00 | 38.68 | O |
| ATOM | 6 | C | GLU | 25 | 5.081 | −0.176 | 6.662 | 1.00 | 30.27 | C |
| ATOM | 7 | O | GLU | 25 | 4.374 | −1.161 | 6.879 | 1.00 | 31.21 | O |
| ATOM | 8 | N | GLU | 25 | 6.922 | −0.708 | 8.375 | 1.00 | 29.47 | N |
| ATOM | 9 | CA | GLU | 25 | 6.567 | −0.166 | 7.021 | 1.00 | 31.52 | C |
| ATOM | 10 | N | THR | 26 | 4.610 | 0.938 | 6.116 | 1.00 | 28.18 | N |
| ATOM | 11 | CA | THR | 26 | 3.217 | 1.047 | 5.711 | 1.00 | 24.93 | C |
| ATOM | 12 | CB | THR | 26 | 2.441 | 2.031 | 6.611 | 1.00 | 24.28 | C |
| ATOM | 13 | OG1 | THR | 26 | 2.654 | 1.706 | 7.990 | 1.00 | 23.56 | O |
| ATOM | 14 | CG2 | THR | 26 | 0.955 | 1.959 | 6.304 | 1.00 | 22.48 | C |
| ATOM | 15 | C | THR | 26 | 3.096 | 1.533 | 4.264 | 1.00 | 24.10 | C |
| ATOM | 16 | O | THR | 26 | 3.633 | 2.581 | 3.908 | 1.00 | 22.83 | O |
| ATOM | 17 | N | LEU | 27 | 2.405 | 0.760 | 3.431 | 1.00 | 19.92 | N |
| ATOM | 18 | CA | LEU | 27 | 2.177 | 1.160 | 2.047 | 1.00 | 20.55 | C |
| ATOM | 19 | CB | LEU | 27 | 2.052 | −0.044 | 1.107 | 1.00 | 22.12 | C |
| ATOM | 20 | CG | LEU | 27 | 3.257 | −0.991 | 1.005 | 1.00 | 24.55 | C |
| ATOM | 21 | CD1 | LEU | 27 | 2.945 | −2.199 | 0.113 | 1.00 | 22.27 | C |
| ATOM | 22 | CD2 | LEU | 27 | 4.506 | −0.259 | 0.513 | 1.00 | 22.59 | C |
| ATOM | 23 | C | LEU | 27 | 0.899 | 1.995 | 2.057 | 1.00 | 19.40 | C |
| ATOM | 24 | O | LEU | 27 | −0.124 | 1.568 | 2.599 | 1.00 | 18.49 | O |
| ATOM | 25 | N | VAL | 28 | 0.956 | 3.190 | 1.476 | 1.00 | 20.26 | N |
| ATOM | 26 | CA | VAL | 28 | −0.206 | 4.075 | 1.457 | 1.00 | 21.18 | C |
| ATOM | 27 | CB | VAL | 28 | −0.090 | 5.200 | 2.523 | 1.00 | 19.01 | C |
| ATOM | 28 | CG1 | VAL | 28 | 0.094 | 4.599 | 3.897 | 1.00 | 19.71 | C |
| ATOM | 29 | CG2 | VAL | 28 | 1.057 | 6.125 | 2.183 | 1.00 | 20.08 | C |
| ATOM | 30 | C | VAL | 28 | −0.481 | 4.741 | 0.118 | 1.00 | 21.98 | C |
| ATOM | 31 | O | VAL | 28 | 0.431 | 4.966 | −0.679 | 1.00 | 23.19 | O |
| ATOM | 32 | N | ARG | 29 | −1.755 | 5.042 | −0.120 | 1.00 | 23.38 | N |
| ATOM | 33 | CA | ARG | 29 | −2.188 | 5.722 | −1.338 | 1.00 | 25.82 | C |
| ATOM | 34 | CB | ARG | 29 | −3.239 | 4.904 | −2.089 | 1.00 | 27.99 | C |
| ATOM | 35 | CG | ARG | 29 | −2.761 | 3.515 | −2.489 | 1.00 | 30.54 | C |
| ATOM | 36 | CD | ARG | 29 | −3.838 | 2.738 | −3.220 | 1.00 | 33.91 | C |
| ATOM | 37 | NE | ARG | 29 | −3.398 | 1.395 | −3.590 | 1.00 | 37.13 | N |
| ATOM | 38 | CZ | ARG | 29 | −2.478 | 1.134 | −4.511 | 1.00 | 39.21 | C |
| ATOM | 39 | NH1 | ARG | 29 | −1.896 | 2.131 | −5.168 | 1.00 | 41.39 | N |
| ATOM | 40 | NH2 | ARG | 29 | −2.135 | −0.122 | −4.771 | 1.00 | 39.25 | N |
| ATOM | 41 | C | ARG | 29 | −2.743 | 7.082 | −0.905 | 1.00 | 26.04 | C |
| ATOM | 42 | O | ARG | 29 | −3.723 | 7.163 | −0.162 | 1.00 | 25.87 | O |
| ATOM | 43 | N | PRO | 30 | −2.100 | 8.167 | −1.358 | 1.00 | 25.80 | N |
| ATOM | 44 | CD | PRO | 30 | −0.679 | 8.055 | −1.738 | 1.00 | 24.67 | C |
| ATOM | 45 | CA | PRO | 30 | −2.394 | 9.579 | −1.111 | 1.00 | 22.90 | C |
| ATOM | 46 | CB | PRO | 30 | −1.203 | 10.259 | −1.751 | 1.00 | 22.35 | C |
| ATOM | 47 | CG | PRO | 30 | −0.114 | 9.428 | −1.255 | 1.00 | 26.65 | C |
| ATOM | 48 | C | PRO | 30 | −3.699 | 10.094 | −1.723 | 1.00 | 22.50 | C |
| ATOM | 49 | O | PRO | 30 | −4.062 | 9.701 | −2.835 | 1.00 | 21.62 | O |
| ATOM | 50 | N | LYS | 31 | −4.411 | 10.954 | −1.001 | 1.00 | 22.08 | N |
| ATOM | 51 | CA | LYS | 31 | −5.593 | 11.574 | −1.590 | 1.00 | 23.03 | C |
| ATOM | 52 | CB | LYS | 31 | −6.451 | 12.381 | −0.620 | 1.00 | 25.31 | C |
| ATOM | 53 | CG | LYS | 31 | −7.122 | 11.655 | 0.501 | 1.00 | 27.67 | C |
| ATOM | 54 | CD | LYS | 31 | −7.906 | 12.701 | 1.266 | 1.00 | 29.82 | C |
| ATOM | 55 | CE | LYS | 31 | −8.654 | 12.122 | 2.423 | 1.00 | 30.22 | C |
| ATOM | 56 | NZ | LYS | 31 | −9.401 | 13.196 | 3.133 | 1.00 | 31.71 | N |
| ATOM | 57 | C | LYS | 31 | −5.065 | 12.527 | −2.648 | 1.00 | 21.77 | C |
| ATOM | 58 | O | LYS | 31 | −3.906 | 12.951 | −2.590 | 1.00 | 21.83 | O |
| ATOM | 59 | N | PRO | 32 | −5.909 | 12.873 | −3.629 | 1.00 | 20.24 | N |
| ATOM | 60 | CD | PRO | 32 | −7.253 | 12.301 | −3.838 | 1.00 | 20.22 | C |
| ATOM | 61 | CA | PRO | 32 | −5.608 | 13.770 | −4.736 | 1.00 | 19.66 | C |
| ATOM | 62 | CB | PRO | 32 | −6.996 | 14.120 | −5.227 | 1.00 | 21.15 | C |
| ATOM | 63 | CG | PRO | 32 | −7.598 | 12.787 | −5.277 | 1.00 | 21.31 | C |
| ATOM | 64 | C | PRO | 32 | −4.799 | 15.018 | −4.348 | 1.00 | 18.96 | C |
| ATOM | 65 | O | PRO | 32 | −3.832 | 15.368 | −5.022 | 1.00 | 17.76 | O |
| ATOM | 66 | N | LEU | 33 | −5.190 | 15.682 | −3.263 | 1.00 | 20.65 | N |
| ATOM | 67 | CA | LEU | 33 | −4.497 | 16.901 | −2.853 | 1.00 | 22.91 | C |
| ATOM | 68 | CB | LEU | 33 | −5.412 | 17.805 | −2.025 | 1.00 | 27.03 | C |
| ATOM | 69 | CG | LEU | 33 | −6.690 | 18.264 | −2.733 | 1.00 | 30.44 | C |
| ATOM | 70 | CD1 | LEU | 33 | −7.567 | 19.092 | −1.796 | 1.00 | 32.45 | C |
| ATOM | 71 | CD2 | LEU | 33 | −6.385 | 19.036 | −4.014 | 1.00 | 31.10 | C |
| ATOM | 72 | C | LEU | 33 | −3.172 | 16.659 | −2.141 | 1.00 | 22.13 | C |
| ATOM | 73 | O | LEU | 33 | −2.277 | 17.507 | −2.169 | 1.00 | 20.13 | O |
| ATOM | 74 | N | LEU | 34 | −3.041 | 15.500 | −1.507 | 1.00 | 22.44 | N |
| ATOM | 75 | CA | LEU | 34 | −1.788 | 15.170 | −0.845 | 1.00 | 22.32 | C |
| ATOM | 76 | CB | LEU | 34 | −1.967 | 14.032 | 0.158 | 1.00 | 22.46 | C |
| ATOM | 77 | CG | LEU | 34 | −0.686 | 13.562 | 0.851 | 1.00 | 25.03 | C |
| ATOM | 78 | CD1 | LEU | 34 | 0.092 | 14.709 | 1.488 | 1.00 | 22.68 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 79 | CD2 | LEU | 34 | −0.984 | 12.449 | 1.846 | 1.00 | 25.15 | C |
| ATOM | 80 | C | LEU | 34 | −0.833 | 14.775 | −1.959 | 1.00 | 20.98 | C |
| ATOM | 81 | O | LEU | 34 | 0.370 | 15.027 | −1.892 | 1.00 | 18.72 | O |
| ATOM | 82 | N | LEU | 35 | −1.403 | 14.172 | −2.996 | 1.00 | 22.16 | N |
| ATOM | 83 | CA | LEU | 35 | −0.644 | 13.746 | −4.158 | 1.00 | 22.50 | C |
| ATOM | 84 | CB | LEU | 35 | −1.499 | 12.888 | −5.086 | 1.00 | 21.79 | C |
| ATOM | 85 | CG | LEU | 35 | −0.799 | 12.451 | −6.371 | 1.00 | 21.31 | C |
| ATOM | 86 | CD1 | LEU | 35 | 0.509 | 11.738 | −6.069 | 1.00 | 22.29 | C |
| ATOM | 87 | CD2 | LEU | 35 | −1.709 | 11.605 | −7.249 | 1.00 | 21.81 | C |
| ATOM | 88 | C | LEU | 35 | −0.120 | 14.950 | −4.913 | 1.00 | 23.62 | C |
| ATOM | 89 | O | LEU | 35 | 0.965 | 14.909 | −5.489 | 1.00 | 24.50 | O |
| ATOM | 90 | N | LYS | 36 | −0.892 | 16.029 | −4.887 | 1.00 | 26.45 | N |
| ATOM | 91 | CA | LYS | 36 | −0.517 | 17.247 | −5.581 | 1.00 | 30.02 | C |
| ATOM | 92 | CB | LYS | 36 | −1.739 | 18.156 | −5.759 | 1.00 | 31.51 | C |
| ATOM | 93 | CG | LYS | 36 | −1.468 | 19.454 | −6.494 | 1.00 | 34.42 | C |
| ATOM | 94 | CD | LYS | 36 | −2.742 | 20.280 | −6.633 | 1.00 | 37.59 | C |
| ATOM | 95 | CE | LYS | 36 | −2.483 | 21.584 | −7.381 | 1.00 | 40.02 | C |
| ATOM | 96 | NZ | LYS | 36 | −3.723 | 22.409 | −7.540 | 1.00 | 42.11 | N |
| ATOM | 97 | C | LYS | 36 | 0.624 | 17.964 | −4.864 | 1.00 | 30.99 | C |
| ATOM | 98 | O | LYS | 36 | 1.321 | 18.782 | −5.460 | 1.00 | 32.96 | O |
| ATOM | 99 | N | LEU | 37 | 0.828 | 17.645 | −3.590 | 1.00 | 31.87 | N |
| ATOM | 100 | CA | LEU | 37 | 1.909 | 18.274 | −2.841 | 1.00 | 33.15 | C |
| ATOM | 101 | CB | LEU | 37 | 1.504 | 18.569 | −1.395 | 1.00 | 34.78 | C |
| ATOM | 102 | CG | LEU | 37 | 0.316 | 19.498 | −1.144 | 1.00 | 37.22 | C |
| ATOM | 103 | CD1 | LEU | 37 | 0.039 | 19.625 | 0.347 | 1.00 | 36.79 | C |
| ATOM | 104 | CD2 | LEU | 37 | 0.540 | 20.873 | −1.760 | 1.00 | 38.28 | C |
| ATOM | 105 | C | LEU | 37 | 3.153 | 17.395 | −2.866 | 1.00 | 32.75 | C |
| ATOM | 106 | O | LEU | 37 | 4.277 | 17.889 | −2.747 | 1.00 | 31.66 | O |
| ATOM | 107 | N | LEU | 38 | 2.945 | 16.093 | −3.040 | 1.00 | 30.45 | N |
| ATOM | 108 | CA | LEU | 38 | 4.054 | 15.155 | −3.080 | 1.00 | 28.31 | C |
| ATOM | 109 | CB | LEU | 38 | 3.578 | 13.726 | −2.805 | 1.00 | 27.70 | C |
| ATOM | 110 | CG | LEU | 38 | 2.878 | 13.360 | −1.492 | 1.00 | 27.23 | C |
| ATOM | 111 | CD1 | LEU | 38 | 2.383 | 11.925 | −1.547 | 1.00 | 27.09 | C |
| ATOM | 112 | CD2 | LEU | 38 | 3.750 | 13.597 | −0.262 | 1.00 | 24.95 | C |
| ATOM | 113 | C | LEU | 38 | 4.713 | 15.230 | −4.451 | 1.00 | 28.49 | C |
| ATOM | 114 | O | LEU | 38 | 5.888 | 14.897 | −4.598 | 1.00 | 29.16 | O |
| ATOM | 115 | N | LYS | 39 | 3.956 | 15.684 | −5.449 | 1.00 | 27.07 | N |
| ATOM | 116 | CA | LYS | 39 | 4.480 | 15.783 | −6.806 | 1.00 | 28.73 | C |
| ATOM | 117 | CB | LYS | 39 | 3.373 | 15.754 | −7.861 | 1.00 | 33.27 | C |
| ATOM | 118 | CG | LYS | 39 | 2.504 | 14.521 | −7.920 | 1.00 | 37.75 | C |
| ATOM | 119 | CD | LYS | 39 | 1.487 | 14.719 | −9.035 | 1.00 | 41.51 | C |
| ATOM | 120 | CE | LYS | 39 | 0.550 | 13.539 | −9.187 | 1.00 | 45.31 | C |
| ATOM | 121 | NZ | LYS | 39 | −0.430 | 13.767 | −10.292 | 1.00 | 47.13 | N |
| ATOM | 122 | C | LYS | 39 | 5.304 | 17.036 | −7.034 | 1.00 | 25.77 | C |
| ATOM | 123 | O | LYS | 39 | 6.154 | 17.062 | −7.916 | 1.00 | 27.98 | O |
| ATOM | 124 | N | SER | 40 | 5.064 | 18.071 | −6.240 | 1.00 | 24.34 | N |
| ATOM | 125 | CA | SER | 40 | 5.795 | 19.311 | −6.427 | 1.00 | 23.75 | C |
| ATOM | 126 | CB | SER | 40 | 5.033 | 20.501 | −5.845 | 1.00 | 24.25 | C |
| ATOM | 127 | OG | SER | 40 | 4.844 | 20.354 | −4.451 | 1.00 | 24.47 | O |
| ATOM | 128 | C | SER | 40 | 7.180 | 19.229 | −5.825 | 1.00 | 23.75 | C |
| ATOM | 129 | O | SER | 40 | 8.029 | 20.066 | −6.099 | 1.00 | 26.76 | O |
| ATOM | 130 | N | VAL | 41 | 7.414 | 18.203 | −5.018 | 1.00 | 26.35 | N |
| ATOM | 131 | CA | VAL | 41 | 8.701 | 18.055 | −4.367 | 1.00 | 25.90 | C |
| ATOM | 132 | CB | VAL | 41 | 8.550 | 18.299 | −2.846 | 1.00 | 26.80 | C |
| ATOM | 133 | CG1 | VAL | 41 | 7.800 | 17.139 | −2.204 | 1.00 | 25.77 | C |
| ATOM | 134 | CG2 | VAL | 41 | 9.905 | 18.491 | −2.202 | 1.00 | 28.50 | C |
| ATOM | 135 | C | VAL | 41 | 9.308 | 16.674 | −4.597 | 1.00 | 26.12 | C |
| ATOM | 136 | O | VAL | 41 | 10.480 | 16.450 | −4.300 | 1.00 | 28.42 | O |
| ATOM | 137 | N | GLY | 42 | 8.523 | 15.751 | −5.144 | 1.00 | 24.94 | N |
| ATOM | 138 | CA | GLY | 42 | 9.049 | 14.416 | −5.363 | 1.00 | 22.59 | C |
| ATOM | 139 | C | GLY | 42 | 8.438 | 13.615 | −6.495 | 1.00 | 22.27 | C |
| ATOM | 140 | O | GLY | 42 | 7.720 | 14.143 | −7.347 | 1.00 | 19.19 | O |
| ATOM | 141 | N | ALA | 43 | 8.740 | 12.321 | −6.490 | 1.00 | 21.23 | N |
| ATOM | 142 | CA | ALA | 43 | 8.252 | 11.387 | −7.491 | 1.00 | 23.12 | C |
| ATOM | 143 | CB | ALA | 43 | 8.939 | 10.043 | −7.326 | 1.00 | 22.78 | C |
| ATOM | 144 | C | ALA | 43 | 6.740 | 11.202 | −7.448 | 1.00 | 26.26 | C |
| ATOM | 145 | O | ALA | 43 | 6.137 | 11.093 | −6.382 | 1.00 | 26.47 | O |
| ATOM | 146 | N | GLN | 44 | 6.144 | 11.182 | −8.632 | 1.00 | 29.51 | N |
| ATOM | 147 | CA | GLN | 44 | 4.711 | 10.994 | −8.814 | 1.00 | 34.61 | C |
| ATOM | 148 | CB | GLN | 44 | 4.254 | 11.798 | −10.044 | 1.00 | 38.60 | C |
| ATOM | 149 | CG | GLN | 44 | 2.772 | 11.752 | −10.418 | 1.00 | 44.52 | C |
| ATOM | 150 | CD | GLN | 44 | 2.343 | 10.341 | −10.743 | 1.00 | 47.57 | C |
| ATOM | 151 | OE1 | GLN | 44 | 1.459 | 9.781 | −10.093 | 1.00 | 50.77 | O |
| ATOM | 152 | NE2 | GLN | 44 | 2.959 | 9.760 | −11.768 | 1.00 | 49.38 | N |
| ATOM | 153 | C | GLN | 44 | 4.452 | 9.486 | −8.949 | 1.00 | 33.65 | C |
| ATOM | 154 | O | GLN | 44 | 4.970 | 8.844 | −9.857 | 1.00 | 34.09 | O |
| ATOM | 155 | N | LYS | 45 | 3.660 | 8.925 | −8.040 | 1.00 | 33.88 | N |
| ATOM | 156 | CA | LYS | 45 | 3.353 | 7.493 | −8.071 | 1.00 | 34.47 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 157 | CB | LYS | 45 | 4.586 | 6.652 | −7.744 | 1.00 | 31.48 | C |
| ATOM | 158 | CG | LYS | 45 | 5.205 | 6.911 | −6.388 | 1.00 | 28.37 | C |
| ATOM | 159 | CD | LYS | 45 | 6.411 | 6.017 | −6.214 | 1.00 | 24.70 | C |
| ATOM | 160 | CE | LYS | 45 | 7.084 | 6.228 | −4.883 | 1.00 | 24.73 | C |
| ATOM | 161 | NZ | LYS | 45 | 8.267 | 5.329 | −4.749 | 1.00 | 24.48 | N |
| ATOM | 162 | C | LYS | 45 | 2.151 | 7.096 | −7.218 | 1.00 | 36.41 | C |
| ATOM | 163 | O | LYS | 45 | 1.924 | 7.670 | −6.157 | 1.00 | 36.79 | O |
| ATOM | 164 | N | ASP | 46 | 1.375 | 6.120 | −7.693 | 1.00 | 39.70 | N |
| ATOM | 165 | CA | ASP | 46 | 0.178 | 5.678 | −6.974 | 1.00 | 41.06 | C |
| ATOM | 166 | CB | ASP | 46 | −0.641 | 4.672 | −7.792 | 1.00 | 42.39 | C |
| ATOM | 167 | CG | ASP | 46 | −1.137 | 5.241 | −9.105 | 1.00 | 43.83 | C |
| ATOM | 168 | OD1 | ASP | 46 | −0.864 | 4.624 | −10.156 | 1.00 | 45.18 | O |
| ATOM | 169 | OD2 | ASP | 46 | −1.799 | 6.301 | −9.086 | 1.00 | 43.47 | O |
| ATOM | 170 | C | ASP | 46 | 0.391 | 5.118 | −5.573 | 1.00 | 40.30 | C |
| ATOM | 171 | O | ASP | 46 | −0.539 | 5.103 | −4.769 | 1.00 | 40.91 | O |
| ATOM | 172 | N | THR | 47 | 1.605 | 4.671 | −5.268 | 1.00 | 38.48 | N |
| ATOM | 173 | CA | THR | 47 | 1.868 | 4.100 | −3.953 | 1.00 | 35.27 | C |
| ATOM | 174 | CB | THR | 47 | 1.860 | 2.564 | −4.000 | 1.00 | 34.96 | C |
| ATOM | 175 | OG1 | THR | 47 | 0.592 | 2.115 | −4.482 | 1.00 | 35.07 | O |
| ATOM | 176 | CG2 | THR | 47 | 2.083 | 1.986 | −2.614 | 1.00 | 34.48 | C |
| ATOM | 177 | C | THR | 47 | 3.165 | 4.561 | −3.312 | 1.00 | 33.33 | C |
| ATOM | 178 | O | THR | 47 | 4.224 | 4.569 | −3.942 | 1.00 | 34.15 | O |
| ATOM | 179 | N | TYR | 48 | 3.055 | 4.951 | −2.048 | 1.00 | 30.30 | N |
| ATOM | 180 | CA | TYR | 48 | 4.180 | 5.435 | −1.256 | 1.00 | 27.10 | C |
| ATOM | 181 | CB | TYR | 48 | 4.048 | 6.925 | −0.949 | 1.00 | 24.18 | C |
| ATOM | 182 | CG | TYR | 48 | 3.995 | 7.837 | −2.150 | 1.00 | 21.88 | C |
| ATOM | 183 | CD1 | TYR | 48 | 5.152 | 8.418 | −2.659 | 1.00 | 19.95 | C |
| ATOM | 184 | CE1 | TYR | 48 | 5.096 | 9.298 | −3.727 | 1.00 | 20.60 | C |
| ATOM | 185 | CD2 | TYR | 48 | 2.782 | 8.153 | −2.747 | 1.00 | 19.91 | C |
| ATOM | 186 | CE2 | TYR | 48 | 2.716 | 9.027 | −3.812 | 1.00 | 20.90 | C |
| ATOM | 187 | CZ | TYR | 48 | 3.872 | 9.598 | −4.298 | 1.00 | 20.62 | C |
| ATOM | 188 | OH | TYR | 48 | 3.795 | 10.481 | −5.347 | 1.00 | 22.83 | O |
| ATOM | 189 | C | TYR | 48 | 4.269 | 4.685 | 0.061 | 1.00 | 26.72 | C |
| ATOM | 190 | O | TYR | 48 | 3.275 | 4.158 | 0.558 | 1.00 | 27.60 | O |
| ATOM | 191 | N | THR | 49 | 5.470 | 4.620 | 0.616 | 1.00 | 27.57 | N |
| ATOM | 192 | CA | THR | 49 | 5.647 | 4.001 | 1.916 | 1.00 | 27.42 | C |
| ATOM | 193 | CB | THR | 49 | 7.100 | 3.558 | 2.171 | 1.00 | 26.03 | C |
| ATOM | 194 | OG1 | THR | 49 | 7.953 | 4.708 | 2.191 | 1.00 | 24.83 | O |
| ATOM | 195 | CG2 | THR | 49 | 7.562 | 2.595 | 1.092 | 1.00 | 26.14 | C |
| ATOM | 196 | C | THR | 49 | 5.317 | 5.167 | 2.836 | 1.00 | 26.91 | C |
| ATOM | 197 | O | THR | 49 | 5.606 | 6.313 | 2.506 | 1.00 | 27.92 | O |
| ATOM | 198 | N | MET | 50 | 4.692 | 4.891 | 3.969 | 1.00 | 28.56 | N |
| ATOM | 199 | CA | MET | 50 | 4.345 | 5.953 | 4.905 | 1.00 | 30.04 | C |
| ATOM | 200 | CB | MET | 50 | 3.773 | 5.358 | 6.190 | 1.00 | 28.54 | C |
| ATOM | 201 | CG | MET | 50 | 3.355 | 6.367 | 7.246 | 1.00 | 30.69 | C |
| ATOM | 202 | SD | MET | 50 | 2.058 | 7.489 | 6.688 | 1.00 | 30.76 | S |
| ATOM | 203 | CE | MET | 50 | 2.888 | 9.022 | 6.804 | 1.00 | 31.08 | C |
| ATOM | 204 | C | MET | 50 | 5.605 | 6.746 | 5.233 | 1.00 | 30.79 | C |
| ATOM | 205 | O | MET | 50 | 5.546 | 7.896 | 5.664 | 1.00 | 31.44 | O |
| ATOM | 206 | N | LYS | 51 | 6.753 | 6.132 | 4.992 | 1.00 | 31.31 | N |
| ATOM | 207 | CA | LYS | 51 | 8.008 | 6.764 | 5.343 | 1.00 | 31.72 | C |
| ATOM | 208 | CB | LYS | 51 | 8.996 | 5.654 | 5.711 | 1.00 | 34.50 | C |
| ATOM | 209 | CG | LYS | 51 | 10.325 | 6.042 | 6.283 | 1.00 | 39.52 | C |
| ATOM | 210 | CD | LYS | 51 | 11.086 | 4.747 | 6.577 | 1.00 | 43.25 | C |
| ATOM | 211 | CE | LYS | 51 | 12.449 | 4.991 | 7.201 | 1.00 | 46.68 | C |
| ATOM | 212 | NZ | LYS | 51 | 12.318 | 5.719 | 8.503 | 1.00 | 47.10 | N |
| ATOM | 213 | C | LYS | 51 | 8.503 | 7.745 | 4.265 | 1.00 | 28.34 | C |
| ATOM | 214 | O | LYS | 51 | 9.297 | 8.637 | 4.559 | 1.00 | 25.46 | O |
| ATOM | 215 | N | GLU | 52 | 8.011 | 7.600 | 3.032 | 1.00 | 24.36 | N |
| ATOM | 216 | CA | GLU | 52 | 8.388 | 8.523 | 1.956 | 1.00 | 23.10 | C |
| ATOM | 217 | CB | GLU | 52 | 8.166 | 7.936 | 0.560 | 1.00 | 23.72 | C |
| ATOM | 218 | CG | GLU | 52 | 8.895 | 6.653 | 0.213 | 1.00 | 26.58 | C |
| ATOM | 219 | CD | GLU | 52 | 8.521 | 6.256 | −1.209 | 1.00 | 25.01 | C |
| ATOM | 220 | OE1 | GLU | 52 | 7.629 | 5.400 | −1.371 | 1.00 | 24.55 | O |
| ATOM | 221 | OE2 | GLU | 52 | 9.123 | 6.785 | −2.164 | 1.00 | 25.12 | O |
| ATOM | 222 | C | GLU | 52 | 7.468 | 9.738 | 2.088 | 1.00 | 21.67 | C |
| ATOM | 223 | O | GLU | 52 | 7.843 | 10.860 | 1.740 | 1.00 | 18.74 | O |
| ATOM | 224 | N | VAL | 53 | 6.263 | 9.495 | 2.599 | 1.00 | 18.59 | N |
| ATOM | 225 | CA | VAL | 53 | 5.268 | 10.545 | 2.763 | 1.00 | 19.55 | C |
| ATOM | 226 | CB | VAL | 53 | 3.896 | 9.949 | 3.143 | 1.00 | 19.33 | C |
| ATOM | 227 | CG1 | VAL | 53 | 2.896 | 11.062 | 3.434 | 1.00 | 19.57 | C |
| ATOM | 228 | CG2 | VAL | 53 | 3.394 | 9.067 | 2.016 | 1.00 | 20.00 | C |
| ATOM | 229 | C | VAL | 53 | 5.703 | 11.518 | 3.841 | 1.00 | 19.68 | C |
| ATOM | 230 | O | VAL | 53 | 5.559 | 12.727 | 3.684 | 1.00 | 19.09 | O |
| ATOM | 231 | N | LEU | 54 | 6.253 | 10.983 | 4.926 | 1.00 | 21.56 | N |
| ATOM | 232 | CA | LEU | 54 | 6.732 | 11.811 | 6.022 | 1.00 | 24.05 | C |
| ATOM | 233 | CB | LEU | 54 | 7.118 | 10.949 | 7.227 | 1.00 | 25.58 | C |
| ATOM | 234 | CG | LEU | 54 | 5.962 | 10.130 | 7.805 | 1.00 | 27.53 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 235 | CD1 | LEU | 54 | 6.406 | 9.184 | 8.917 | 1.00 | 27.26 | C |
| ATOM | 236 | CD2 | LEU | 54 | 4.854 | 11.055 | 8.278 | 1.00 | 27.23 | C |
| ATOM | 237 | C | LEU | 54 | 7.917 | 12.628 | 5.530 | 1.00 | 23.85 | C |
| ATOM | 238 | O | LEU | 54 | 8.066 | 13.800 | 5.876 | 1.00 | 24.62 | O |
| ATOM | 239 | N | PHE | 55 | 8.747 | 12.002 | 4.702 | 1.00 | 22.58 | N |
| ATOM | 240 | CA | PHE | 55 | 9.908 | 12.674 | 4.145 | 1.00 | 21.31 | C |
| ATOM | 241 | CB | PHE | 55 | 10.796 | 11.716 | 3.357 | 1.00 | 20.68 | C |
| ATOM | 242 | CG | PHE | 55 | 11.981 | 12.387 | 2.725 | 1.00 | 20.30 | C |
| ATOM | 243 | CD1 | PHE | 55 | 13.012 | 12.888 | 3.507 | 1.00 | 18.41 | C |
| ATOM | 244 | CD2 | PHE | 55 | 12.048 | 12.549 | 1.346 | 1.00 | 19.84 | C |
| ATOM | 245 | CE1 | PHE | 55 | 14.085 | 13.538 | 2.928 | 1.00 | 18.68 | C |
| ATOM | 246 | CE2 | PHE | 55 | 13.120 | 13.201 | 0.759 | 1.00 | 18.51 | C |
| ATOM | 247 | CZ | PHE | 55 | 14.140 | 13.696 | 1.552 | 1.00 | 19.56 | C |
| ATOM | 248 | C | PHE | 55 | 9.512 | 13.850 | 3.269 | 1.00 | 20.62 | C |
| ATOM | 249 | O | PHE | 55 | 9.963 | 14.971 | 3.493 | 1.00 | 23.48 | O |
| ATOM | 250 | N | TYR | 56 | 8.670 | 13.599 | 2.270 | 1.00 | 19.21 | N |
| ATOM | 251 | CA | TYR | 56 | 8.243 | 14.671 | 1.382 | 1.00 | 17.94 | C |
| ATOM | 252 | CB | TYR | 56 | 7.459 | 14.142 | 0.182 | 1.00 | 17.19 | C |
| ATOM | 253 | CG | TYR | 56 | 8.259 | 13.265 | −0.752 | 1.00 | 17.01 | C |
| ATOM | 254 | CD1 | TYR | 56 | 9.447 | 13.726 | −1.310 | 1.00 | 16.35 | C |
| ATOM | 255 | CE1 | TYR | 56 | 10.130 | 12.987 | −2.251 | 1.00 | 15.96 | C |
| ATOM | 256 | CD2 | TYR | 56 | 7.781 | 12.024 | −1.158 | 1.00 | 17.74 | C |
| ATOM | 257 | CE2 | TYR | 56 | 8.457 | 11.273 | −2.105 | 1.00 | 18.06 | C |
| ATOM | 258 | CZ | TYR | 56 | 9.627 | 11.763 | −2.651 | 1.00 | 18.15 | C |
| ATOM | 259 | OH | TYR | 56 | 10.268 | 11.055 | −3.637 | 1.00 | 17.16 | O |
| ATOM | 260 | C | TYR | 56 | 7.506 | 15.830 | 2.034 | 1.00 | 18.40 | C |
| ATOM | 261 | O | TYR | 56 | 7.708 | 16.974 | 1.632 | 1.00 | 20.22 | O |
| ATOM | 262 | N | LEU | 57 | 6.666 | 15.559 | 3.034 | 1.00 | 18.61 | N |
| ATOM | 263 | CA | LEU | 57 | 5.964 | 16.652 | 3.699 | 1.00 | 19.85 | C |
| ATOM | 264 | CB | LEU | 57 | 4.869 | 16.162 | 4.655 | 1.00 | 20.61 | C |
| ATOM | 265 | CG | LEU | 57 | 3.644 | 15.424 | 4.115 | 1.00 | 23.15 | C |
| ATOM | 266 | CD1 | LEU | 57 | 2.757 | 14.911 | 5.243 | 1.00 | 23.67 | C |
| ATOM | 267 | CD2 | LEU | 57 | 2.843 | 16.320 | 3.162 | 1.00 | 21.07 | C |
| ATOM | 268 | C | LEU | 57 | 6.942 | 17.560 | 4.425 | 1.00 | 19.93 | C |
| ATOM | 269 | O | LEU | 57 | 6.778 | 18.777 | 4.429 | 1.00 | 20.07 | O |
| ATOM | 270 | N | GLY | 58 | 7.970 | 16.968 | 5.023 | 1.00 | 18.96 | N |
| ATOM | 271 | CA | GLY | 58 | 8.959 | 17.764 | 5.724 | 1.00 | 19.61 | C |
| ATOM | 272 | C | GLY | 58 | 9.735 | 18.612 | 4.736 | 1.00 | 20.66 | C |
| ATOM | 273 | O | GLY | 58 | 9.973 | 19.801 | 4.968 | 1.00 | 19.89 | O |
| ATOM | 274 | N | GLN | 59 | 10.132 | 18.003 | 3.622 | 1.00 | 21.02 | N |
| ATOM | 275 | CA | GLN | 59 | 10.873 | 18.730 | 2.600 | 1.00 | 22.78 | C |
| ATOM | 276 | CB | GLN | 59 | 11.519 | 17.776 | 1.599 | 1.00 | 22.59 | C |
| ATOM | 277 | CG | GLN | 59 | 12.505 | 16.839 | 2.250 | 1.00 | 25.03 | C |
| ATOM | 278 | CD | GLN | 59 | 13.576 | 17.674 | 2.912 | 1.00 | 26.69 | C |
| ATOM | 279 | OE1 | GLN | 59 | 13.877 | 17.502 | 4.090 | 1.00 | 28.42 | O |
| ATOM | 280 | NE2 | GLN | 59 | 14.139 | 18.612 | 2.160 | 1.00 | 27.94 | N |
| ATOM | 281 | C | GLN | 59 | 9.980 | 19.745 | 1.900 | 1.00 | 21.11 | C |
| ATOM | 282 | O | GLN | 59 | 10.458 | 20.730 | 1.342 | 1.00 | 20.60 | O |
| ATOM | 283 | N | TYR | 60 | 8.675 | 19.504 | 1.943 | 1.00 | 20.96 | N |
| ATOM | 284 | CA | TYR | 60 | 7.725 | 20.427 | 1.340 | 1.00 | 21.51 | C |
| ATOM | 285 | CB | TYR | 60 | 6.350 | 19.786 | 1.207 | 1.00 | 20.18 | C |
| ATOM | 286 | CG | TYR | 60 | 5.290 | 20.727 | 0.684 | 1.00 | 19.26 | C |
| ATOM | 287 | CD1 | TYR | 60 | 5.127 | 20.946 | −0.677 | 1.00 | 18.65 | C |
| ATOM | 288 | CE1 | TYR | 60 | 4.145 | 21.796 | −1.148 | 1.00 | 18.43 | C |
| ATOM | 289 | CD2 | TYR | 60 | 4.444 | 21.390 | 1.563 | 1.00 | 18.15 | C |
| ATOM | 290 | CE2 | TYR | 60 | 3.465 | 22.238 | 1.106 | 1.00 | 19.04 | C |
| ATOM | 291 | CZ | TYR | 60 | 3.314 | 22.437 | −0.251 | 1.00 | 19.66 | C |
| ATOM | 292 | OH | TYR | 60 | 2.316 | 23.266 | −0.705 | 1.00 | 17.66 | O |
| ATOM | 293 | C | TYR | 60 | 7.631 | 21.661 | 2.221 | 1.00 | 21.23 | C |
| ATOM | 294 | O | TYR | 60 | 7.592 | 22.793 | 1.737 | 1.00 | 21.02 | O |
| ATOM | 295 | N | ILE | 61 | 7.615 | 21.414 | 3.525 | 1.00 | 20.45 | N |
| ATOM | 296 | CA | ILE | 61 | 7.514 | 22.463 | 4.518 | 1.00 | 19.88 | C |
| ATOM | 297 | CB | ILE | 61 | 7.305 | 21.841 | 5.913 | 1.00 | 16.63 | C |
| ATOM | 298 | CG2 | ILE | 61 | 7.405 | 22.907 | 6.990 | 1.00 | 15.17 | C |
| ATOM | 299 | CG1 | ILE | 61 | 5.961 | 21.112 | 5.956 | 1.00 | 14.67 | C |
| ATOM | 300 | CD1 | ILE | 61 | 5.660 | 20.431 | 7.295 | 1.00 | 13.50 | C |
| ATOM | 301 | C | ILE | 61 | 8.789 | 23.293 | 4.518 | 1.00 | 24.11 | C |
| ATOM | 302 | O | ILE | 61 | 8.779 | 24.463 | 4.915 | 1.00 | 24.81 | O |
| ATOM | 303 | N | MET | 62 | 9.882 | 22.695 | 4.052 | 1.00 | 27.53 | N |
| ATOM | 304 | CA | MET | 62 | 11.158 | 23.399 | 4.010 | 1.00 | 31.34 | C |
| ATOM | 305 | CB | MET | 62 | 12.331 | 22.454 | 4.293 | 1.00 | 34.73 | C |
| ATOM | 306 | CG | MET | 62 | 12.295 | 21.791 | 5.665 | 1.00 | 41.21 | C |
| ATOM | 307 | SD | MET | 62 | 13.705 | 20.685 | 5.949 | 1.00 | 45.94 | S |
| ATOM | 308 | CE | MET | 62 | 15.034 | 21.883 | 6.155 | 1.00 | 46.15 | C |
| ATOM | 309 | C | MET | 62 | 11.394 | 24.154 | 2.710 | 1.00 | 30.78 | C |
| ATOM | 310 | O | MET | 62 | 11.975 | 25.236 | 2.723 | 1.00 | 31.93 | O |
| ATOM | 311 | N | THR | 63 | 10.929 | 23.607 | 1.591 | 1.00 | 30.29 | N |
| ATOM | 312 | CA | THR | 63 | 11.146 | 24.278 | 0.318 | 1.00 | 31.93 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 313 | CB | THR | 63 | 10.913 | 23.331 | −0.879 | 1.00 | 32.45 | C |
| ATOM | 314 | OG1 | THR | 63 | 11.653 | 22.121 | −0.691 | 1.00 | 34.57 | O |
| ATOM | 315 | CG2 | THR | 63 | 11.383 | 23.992 | −2.168 | 1.00 | 33.58 | C |
| ATOM | 316 | C | THR | 63 | 10.222 | 25.476 | 0.164 | 1.00 | 30.66 | C |
| ATOM | 317 | O | THR | 63 | 10.550 | 26.430 | −0.535 | 1.00 | 32.12 | O |
| ATOM | 318 | N | LYS | 64 | 9.072 | 25.437 | 0.825 | 1.00 | 30.47 | N |
| ATOM | 319 | CA | LYS | 64 | 8.144 | 26.554 | 0.750 | 1.00 | 30.88 | C |
| ATOM | 320 | CB | LYS | 64 | 6.715 | 26.113 | 0.433 | 1.00 | 31.95 | C |
| ATOM | 321 | CG | LYS | 64 | 6.592 | 25.412 | −0.903 | 1.00 | 33.47 | C |
| ATOM | 322 | CD | LYS | 64 | 5.163 | 25.021 | −1.188 | 1.00 | 35.44 | C |
| ATOM | 323 | CE | LYS | 64 | 4.269 | 26.251 | −1.223 | 1.00 | 35.32 | C |
| ATOM | 324 | NZ | LYS | 64 | 2.851 | 25.905 | −1.507 | 1.00 | 36.49 | N |
| ATOM | 325 | C | LYS | 64 | 8.218 | 27.370 | 2.021 | 1.00 | 30.38 | C |
| ATOM | 326 | O | LYS | 64 | 7.504 | 28.356 | 2.190 | 1.00 | 31.61 | O |
| ATOM | 327 | N | ARG | 65 | 9.096 | 26.929 | 2.914 | 1.00 | 31.08 | N |
| ATOM | 328 | CA | ARG | 65 | 9.350 | 27.604 | 4.176 | 1.00 | 32.41 | C |
| ATOM | 329 | CB | ARG | 65 | 10.296 | 28.776 | 3.921 | 1.00 | 33.62 | C |
| ATOM | 330 | CG | ARG | 65 | 11.569 | 28.220 | 3.304 | 1.00 | 38.45 | C |
| ATOM | 331 | CD | ARG | 65 | 12.660 | 29.194 | 2.949 | 1.00 | 39.91 | C |
| ATOM | 332 | NE | ARG | 65 | 13.766 | 28.425 | 2.375 | 1.00 | 42.85 | N |
| ATOM | 333 | CZ | ARG | 65 | 14.793 | 28.944 | 1.713 | 1.00 | 43.34 | C |
| ATOM | 334 | NH1 | ARG | 65 | 14.878 | 30.255 | 1.530 | 1.00 | 45.53 | N |
| ATOM | 335 | NH2 | ARG | 65 | 15.729 | 28.146 | 1.221 | 1.00 | 43.64 | N |
| ATOM | 336 | C | ARG | 65 | 8.099 | 27.982 | 4.955 | 1.00 | 30.80 | C |
| ATOM | 337 | O | ARG | 65 | 7.856 | 29.145 | 5.259 | 1.00 | 28.75 | O |
| ATOM | 338 | N | LEU | 66 | 7.310 | 26.965 | 5.274 | 1.00 | 31.27 | N |
| ATOM | 339 | CA | LEU | 66 | 6.077 | 27.149 | 6.020 | 1.00 | 31.53 | C |
| ATOM | 340 | CB | LEU | 66 | 5.082 | 26.044 | 5.687 | 1.00 | 30.56 | C |
| ATOM | 341 | CG | LEU | 66 | 4.742 | 25.973 | 4.201 | 1.00 | 30.97 | C |
| ATOM | 342 | CD1 | LEU | 66 | 3.800 | 24.809 | 3.914 | 1.00 | 31.85 | C |
| ATOM | 343 | CD2 | LEU | 66 | 4.156 | 27.290 | 3.700 | 1.00 | 28.41 | C |
| ATOM | 344 | C | LEU | 66 | 6.391 | 27.171 | 7.507 | 1.00 | 32.00 | C |
| ATOM | 345 | O | LEU | 66 | 5.505 | 27.320 | 8.342 | 1.00 | 36.99 | O |
| ATOM | 346 | N | TYR | 67 | 7.669 | 27.018 | 7.822 | 1.00 | 32.16 | N |
| ATOM | 347 | CA | TYR | 67 | 8.147 | 27.010 | 9.196 | 1.00 | 29.34 | C |
| ATOM | 348 | CB | TYR | 67 | 9.300 | 26.023 | 9.365 | 1.00 | 30.19 | C |
| ATOM | 349 | CG | TYR | 67 | 10.505 | 26.362 | 8.517 | 1.00 | 30.32 | C |
| ATOM | 350 | CD1 | TYR | 67 | 11.362 | 27.393 | 8.877 | 1.00 | 31.21 | C |
| ATOM | 351 | CE1 | TYR | 67 | 12.453 | 27.726 | 8.097 | 1.00 | 31.23 | C |
| ATOM | 352 | CD2 | TYR | 67 | 10.775 | 25.668 | 7.348 | 1.00 | 31.49 | C |
| ATOM | 353 | CE2 | TYR | 67 | 11.867 | 25.995 | 6.559 | 1.00 | 31.76 | C |
| ATOM | 354 | CZ | TYR | 67 | 12.702 | 27.025 | 6.939 | 1.00 | 30.71 | C |
| ATOM | 355 | OH | TYR | 67 | 13.790 | 27.351 | 6.163 | 1.00 | 30.69 | O |
| ATOM | 356 | C | TYR | 67 | 8.584 | 28.410 | 9.599 | 1.00 | 26.76 | C |
| ATOM | 357 | O | TYR | 67 | 8.974 | 29.212 | 8.755 | 1.00 | 27.18 | O |
| ATOM | 358 | N | ASP | 68 | 8.505 | 28.710 | 10.887 | 1.00 | 26.00 | N |
| ATOM | 359 | CA | ASP | 68 | 8.931 | 30.012 | 11.376 | 1.00 | 24.98 | C |
| ATOM | 360 | CB | ASP | 68 | 8.536 | 30.213 | 12.832 | 1.00 | 24.44 | C |
| ATOM | 361 | CG | ASP | 68 | 8.916 | 31.581 | 13.354 | 1.00 | 25.82 | C |
| ATOM | 362 | OD1 | ASP | 68 | 8.229 | 32.064 | 14.280 | 1.00 | 27.13 | O |
| ATOM | 363 | OD2 | ASP | 68 | 9.876 | 32.189 | 12.829 | 1.00 | 23.05 | O |
| ATOM | 364 | C | ASP | 68 | 10.456 | 30.065 | 11.239 | 1.00 | 26.08 | C |
| ATOM | 365 | O | ASP | 68 | 11.171 | 29.230 | 11.809 | 1.00 | 20.81 | O |
| ATOM | 366 | N | GLU | 69 | 10.954 | 31.038 | 10.481 | 1.00 | 26.25 | N |
| ATOM | 367 | CA | GLU | 69 | 12.393 | 31.179 | 10.299 | 1.00 | 27.50 | C |
| ATOM | 368 | CB | GLU | 69 | 12.711 | 32.341 | 9.355 | 1.00 | 31.03 | C |
| ATOM | 369 | CG | GLU | 69 | 14.200 | 32.606 | 9.160 | 1.00 | 36.70 | C |
| ATOM | 370 | CD | GLU | 69 | 14.885 | 31.383 | 8.579 | 1.00 | 40.21 | C |
| ATOM | 371 | OE1 | GLU | 69 | 14.189 | 30.407 | 8.224 | 1.00 | 42.79 | O |
| ATOM | 372 | OE2 | GLU | 69 | 16.133 | 31.400 | 8.486 | 1.00 | 41.52 | O |
| ATOM | 373 | C | GLU | 69 | 13.155 | 31.330 | 11.617 | 1.00 | 25.94 | C |
| ATOM | 374 | O | GLU | 69 | 14.320 | 30.956 | 11.705 | 1.00 | 25.86 | O |
| ATOM | 375 | N | LYS | 70 | 12.493 | 31.856 | 12.645 | 1.00 | 23.46 | N |
| ATOM | 376 | CA | LYS | 70 | 13.141 | 32.048 | 13.937 | 1.00 | 23.45 | C |
| ATOM | 377 | CB | LYS | 70 | 12.882 | 33.449 | 14.490 | 1.00 | 26.70 | C |
| ATOM | 378 | CG | LYS | 70 | 13.362 | 34.567 | 13.582 | 1.00 | 28.84 | C |
| ATOM | 379 | CD | LYS | 70 | 14.858 | 34.477 | 13.329 | 1.00 | 31.67 | C |
| ATOM | 380 | CE | LYS | 70 | 15.327 | 35.607 | 12.415 | 1.00 | 33.30 | C |
| ATOM | 381 | NZ | LYS | 70 | 16.788 | 35.549 | 12.150 | 1.00 | 34.03 | N |
| ATOM | 382 | C | LYS | 70 | 12.762 | 30.989 | 14.965 | 1.00 | 22.06 | C |
| ATOM | 383 | O | LYS | 70 | 13.147 | 31.077 | 16.123 | 1.00 | 21.58 | O |
| ATOM | 384 | N | GLN | 71 | 11.995 | 29.993 | 14.541 | 1.00 | 21.15 | N |
| ATOM | 385 | CA | GLN | 71 | 11.588 | 28.913 | 15.436 | 1.00 | 20.20 | C |
| ATOM | 386 | CB | GLN | 71 | 10.497 | 29.383 | 16.407 | 1.00 | 20.24 | C |
| ATOM | 387 | CG | GLN | 71 | 10.110 | 28.357 | 17.460 | 1.00 | 20.50 | C |
| ATOM | 388 | CD | GLN | 71 | 9.029 | 28.928 | 18.363 | 1.00 | 20.46 | C |
| ATOM | 389 | OE1 | GLN | 71 | 8.365 | 29.908 | 18.019 | 1.00 | 24.60 | O |
| ATOM | 390 | NE2 | GLN | 71 | 8.865 | 28.330 | 19.535 | 1.00 | 18.17 | N |

TABLE 4-continued

| 1 | 2 | 3 | 4 | 5 | 6 | 7 | 8 | 9 | 10 | 11 |
|---|---|---|---|---|---|---|---|---|---|---|
| ATOM | 391 | C | GLN | 71 | 11.088 | 27.853 | 14.461 | 1.00 | 20.18 | C |
| ATOM | 392 | O | GLN | 71 | 9.880 | 27.643 | 14.280 | 1.00 | 20.12 | O |
| ATOM | 393 | N | GLN | 72 | 12.056 | 27.188 | 13.840 | 1.00 | 20.81 | N |
| ATOM | 394 | CA | GLN | 72 | 11.806 | 26.189 | 12.813 | 1.00 | 22.77 | C |
| ATOM | 395 | CB | GLN | 72 | 13.119 | 25.855 | 12.110 | 1.00 | 23.53 | C |
| ATOM | 396 | CG | GLN | 72 | 13.723 | 27.086 | 11.456 | 1.00 | 27.22 | C |
| ATOM | 397 | CD | GLN | 72 | 15.027 | 26.744 | 10.776 | 1.00 | 29.38 | C |
| ATOM | 398 | OE1 | GLN | 72 | 15.497 | 25.604 | 10.824 | 1.00 | 30.31 | O |
| ATOM | 399 | NE2 | GLN | 72 | 15.626 | 27.741 | 10.137 | 1.00 | 30.16 | N |
| ATOM | 400 | C | GLN | 72 | 11.028 | 24.940 | 13.195 | 1.00 | 21.80 | C |
| ATOM | 401 | O | GLN | 72 | 10.603 | 24.178 | 12.328 | 1.00 | 20.25 | O |
| ATOM | 402 | N | HIS | 73 | 10.829 | 24.737 | 14.488 | 1.00 | 20.18 | N |
| ATOM | 403 | CA | HIS | 73 | 10.076 | 23.585 | 14.949 | 1.00 | 21.21 | C |
| ATOM | 404 | CB | HIS | 73 | 10.627 | 23.080 | 16.287 | 1.00 | 22.75 | C |
| ATOM | 405 | CG | HIS | 73 | 10.662 | 24.117 | 17.366 | 1.00 | 24.88 | C |
| ATOM | 406 | CD2 | HIS | 73 | 11.670 | 24.911 | 17.801 | 1.00 | 25.16 | C |
| ATOM | 407 | ND1 | HIS | 73 | 9.565 | 24.435 | 18.136 | 1.00 | 26.05 | N |
| ATOM | 408 | CE1 | HIS | 73 | 9.895 | 25.378 | 19.001 | 1.00 | 27.37 | C |
| ATOM | 409 | NE2 | HIS | 73 | 11.167 | 25.684 | 18.818 | 1.00 | 27.33 | N |
| ATOM | 410 | C | HIS | 73 | 8.569 | 23.857 | 14.955 | 1.00 | 19.30 | C |
| ATOM | 411 | O | HIS | 73 | 7.762 | 23.018 | 15.353 | 1.00 | 15.05 | O |
| ATOM | 412 | N | ILE | 74 | 8.202 | 25.049 | 14.495 | 1.00 | 20.68 | N |
| ATOM | 413 | CA | ILE | 74 | 6.800 | 25.442 | 14.408 | 1.00 | 20.38 | C |
| ATOM | 414 | CB | ILE | 74 | 6.517 | 26.761 | 15.170 | 1.00 | 17.27 | C |
| ATOM | 415 | CG2 | ILE | 74 | 5.082 | 27.186 | 14.930 | 1.00 | 16.94 | C |
| ATOM | 416 | CG1 | ILE | 74 | 6.788 | 26.585 | 16.673 | 1.00 | 12.85 | C |
| ATOM | 417 | CD1 | ILE | 74 | 5.940 | 25.522 | 17.350 | 1.00 | 10.25 | C |
| ATOM | 418 | C | ILE | 74 | 6.433 | 25.631 | 12.931 | 1.00 | 22.21 | C |
| ATOM | 419 | O | ILE | 74 | 7.068 | 26.401 | 12.207 | 1.00 | 19.54 | O |
| ATOM | 420 | N | VAL | 75 | 5.406 | 24.914 | 12.489 | 1.00 | 22.66 | N |
| ATOM | 421 | CA | VAL | 75 | 4.968 | 24.994 | 11.106 | 1.00 | 20.85 | C |
| ATOM | 422 | CB | VAL | 75 | 4.656 | 23.596 | 10.552 | 1.00 | 19.84 | C |
| ATOM | 423 | CG1 | VAL | 75 | 4.268 | 23.697 | 9.081 | 1.00 | 17.74 | C |
| ATOM | 424 | CG2 | VAL | 75 | 5.870 | 22.678 | 10.745 | 1.00 | 19.97 | C |
| ATOM | 425 | C | VAL | 75 | 3.730 | 25.866 | 10.931 | 1.00 | 22.04 | C |
| ATOM | 426 | O | VAL | 75 | 2.682 | 25.605 | 11.523 | 1.00 | 19.88 | O |
| ATOM | 427 | N | HIS | 76 | 3.860 | 26.907 | 10.117 | 1.00 | 19.99 | N |
| ATOM | 428 | CA | HIS | 76 | 2.742 | 27.797 | 9.850 | 1.00 | 20.86 | C |
| ATOM | 429 | CB | HIS | 76 | 3.140 | 29.249 | 10.074 | 1.00 | 20.76 | C |
| ATOM | 430 | CG | HIS | 76 | 3.595 | 29.532 | 11.471 | 1.00 | 18.48 | C |
| ATOM | 431 | CD2 | HIS | 76 | 4.799 | 29.914 | 11.958 | 1.00 | 17.24 | C |
| ATOM | 432 | ND1 | HIS | 76 | 2.764 | 29.401 | 12.561 | 1.00 | 18.78 | N |
| ATOM | 433 | CE1 | HIS | 76 | 3.436 | 29.693 | 13.661 | 1.00 | 17.42 | C |
| ATOM | 434 | NE2 | HIS | 76 | 4.673 | 30.007 | 13.323 | 1.00 | 17.51 | N |
| ATOM | 435 | C | HIS | 76 | 2.250 | 27.541 | 8.429 | 1.00 | 22.01 | C |
| ATOM | 436 | O | HIS | 76 | 2.906 | 27.886 | 7.448 | 1.00 | 20.06 | O |
| ATOM | 437 | N | CYS | 77 | 1.076 | 26.934 | 8.333 | 1.00 | 25.10 | N |
| ATOM | 438 | CA | CYS | 77 | 0.503 | 26.582 | 7.049 | 1.00 | 27.53 | C |
| ATOM | 439 | CB | CYS | 77 | 0.499 | 25.055 | 6.882 | 1.00 | 26.53 | C |
| ATOM | 440 | SG | CYS | 77 | −0.321 | 24.144 | 8.202 | 1.00 | 29.08 | S |
| ATOM | 441 | C | CYS | 77 | −0.805 | 27.255 | 6.632 | 1.00 | 28.98 | C |
| ATOM | 442 | O | CYS | 77 | −1.442 | 26.851 | 5.660 | 1.00 | 28.62 | O |
| ATOM | 443 | N | SER | 78 | −1.206 | 28.283 | 7.377 | 1.00 | 31.46 | N |
| ATOM | 444 | CA | SER | 78 | −2.404 | 29.043 | 7.035 | 1.00 | 34.18 | C |
| ATOM | 445 | CB | SER | 78 | −2.859 | 29.936 | 8.186 | 1.00 | 32.67 | C |
| ATOM | 446 | OG | SER | 78 | −1.858 | 30.878 | 8.515 | 1.00 | 32.54 | O |
| ATOM | 447 | C | SER | 78 | −1.935 | 29.883 | 5.851 | 1.00 | 37.37 | C |
| ATOM | 448 | O | SER | 78 | −0.941 | 30.602 | 5.966 | 1.00 | 40.89 | O |
| ATOM | 449 | N | ASN | 79 | −2.637 | 29.782 | 4.725 | 1.00 | 38.16 | N |
| ATOM | 450 | CA | ASN | 79 | −2.281 | 30.491 | 3.490 | 1.00 | 38.25 | C |
| ATOM | 451 | CB | ASN | 79 | −1.490 | 31.788 | 3.729 | 1.00 | 41.43 | C |
| ATOM | 452 | CG | ASN | 79 | −2.269 | 32.814 | 4.535 | 1.00 | 44.32 | C |
| ATOM | 453 | OD1 | ASN | 79 | −1.804 | 33.293 | 5.568 | 1.00 | 47.01 | O |
| ATOM | 454 | ND2 | ASN | 79 | −3.464 | 33.155 | 4.062 | 1.00 | 45.45 | N |
| ATOM | 455 | C | ASN | 79 | −1.535 | 29.579 | 2.522 | 1.00 | 36.47 | C |
| ATOM | 456 | O | ASN | 79 | −1.050 | 30.026 | 1.481 | 1.00 | 36.50 | O |
| ATOM | 457 | N | ASP | 80 | −1.439 | 28.301 | 2.879 | 1.00 | 33.49 | N |
| ATOM | 458 | CA | ASP | 80 | −0.782 | 27.304 | 2.038 | 1.00 | 30.65 | C |
| ATOM | 459 | CB | ASP | 80 | 0.597 | 26.908 | 2.567 | 1.00 | 28.08 | C |
| ATOM | 460 | CG | ASP | 80 | 1.300 | 25.894 | 1.666 | 1.00 | 27.51 | C |
| ATOM | 461 | OD1 | ASP | 80 | 2.347 | 26.248 | 1.088 | 1.00 | 28.18 | O |
| ATOM | 462 | OD2 | ASP | 80 | 0.818 | 24.749 | 1.528 | 1.00 | 24.49 | O |
| ATOM | 463 | C | ASP | 80 | −1.696 | 26.089 | 1.926 | 1.00 | 30.18 | C |
| ATOM | 464 | O | ASP | 80 | −2.399 | 25.750 | 2.876 | 1.00 | 32.29 | O |
| ATOM | 465 | N | LEU | 81 | −1.701 | 25.447 | 0.763 | 1.00 | 29.44 | N |
| ATOM | 466 | CA | LEU | 81 | −2.547 | 24.279 | 0.548 | 1.00 | 28.49 | C |
| ATOM | 467 | CB | LEU | 81 | −2.242 | 23.632 | −0.806 | 1.00 | 30.75 | C |
| ATOM | 468 | CG | LEU | 81 | −3.069 | 22.396 | −1.179 | 1.00 | 32.89 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 469 | CD1 | LEU | 81 | −4.564 | 22.720 | −1.167 | 1.00 | 32.68 | C |
| ATOM | 470 | CD2 | LEU | 81 | −2.658 | 21.821 | −2.530 | 1.00 | 33.32 | C |
| ATOM | 471 | C | LEU | 81 | −2.428 | 23.240 | 1.667 | 1.00 | 27.48 | C |
| ATOM | 472 | O | LEU | 81 | −3.327 | 22.422 | 1.861 | 1.00 | 26.60 | O |
| ATOM | 473 | N | LEU | 82 | −1.328 | 23.284 | 2.411 | 1.00 | 25.83 | N |
| ATOM | 474 | CA | LEU | 82 | −1.121 | 22.326 | 3.485 | 1.00 | 25.93 | C |
| ATOM | 475 | CB | LEU | 82 | 0.335 | 22.334 | 3.953 | 1.00 | 27.37 | C |
| ATOM | 476 | CG | LEU | 82 | 0.714 | 21.341 | 5.051 | 1.00 | 26.40 | C |
| ATOM | 477 | CD1 | LEU | 82 | 0.391 | 19.918 | 4.617 | 1.00 | 28.04 | C |
| ATOM | 478 | CD2 | LEU | 82 | 2.183 | 21.459 | 5.440 | 1.00 | 25.48 | C |
| ATOM | 479 | C | LEU | 82 | −2.075 | 22.622 | 4.640 | 1.00 | 26.61 | C |
| ATOM | 480 | O | LEU | 82 | −2.394 | 21.736 | 5.434 | 1.00 | 24.04 | O |
| ATOM | 481 | N | GLY | 83 | −2.539 | 23.870 | 4.713 | 1.00 | 25.97 | N |
| ATOM | 482 | CA | GLY | 83 | −3.476 | 24.255 | 5.751 | 1.00 | 23.73 | C |
| ATOM | 483 | C | GLY | 83 | −4.816 | 23.613 | 5.437 | 1.00 | 24.97 | C |
| ATOM | 484 | O | GLY | 83 | −5.531 | 23.137 | 6.324 | 1.00 | 23.63 | O |
| ATOM | 485 | N | ASP | 84 | −5.155 | 23.592 | 4.154 | 1.00 | 26.10 | N |
| ATOM | 486 | CA | ASP | 84 | −6.404 | 22.994 | 3.705 | 1.00 | 28.17 | C |
| ATOM | 487 | CB | ASP | 84 | −6.695 | 23.378 | 2.259 | 1.00 | 29.18 | C |
| ATOM | 488 | CG | ASP | 84 | −6.829 | 24.868 | 2.065 | 1.00 | 31.27 | C |
| ATOM | 489 | OD1 | ASP | 84 | −6.896 | 25.604 | 3.073 | 1.00 | 30.35 | O |
| ATOM | 490 | OD2 | ASP | 84 | −6.856 | 25.298 | 0.891 | 1.00 | 33.57 | O |
| ATOM | 491 | C | ASP | 84 | −6.345 | 21.477 | 3.817 | 1.00 | 28.68 | C |
| ATOM | 492 | O | ASP | 84 | −7.369 | 20.818 | 3.992 | 1.00 | 29.33 | O |
| ATOM | 493 | N | LEU | 85 | −5.138 | 20.931 | 3.728 | 1.00 | 28.47 | N |
| ATOM | 494 | CA | LEU | 85 | −4.946 | 19.491 | 3.787 | 1.00 | 28.25 | C |
| ATOM | 495 | CB | LEU | 85 | −3.572 | 19.113 | 3.231 | 1.00 | 29.46 | C |
| ATOM | 496 | CG | LEU | 85 | −3.224 | 17.628 | 3.151 | 1.00 | 31.51 | C |
| ATOM | 497 | CD1 | LEU | 85 | −4.226 | 16.913 | 2.258 | 1.00 | 31.47 | C |
| ATOM | 498 | CD2 | LEU | 85 | −1.809 | 17.393 | 2.634 | 1.00 | 32.07 | C |
| ATOM | 499 | C | LEU | 85 | −5.125 | 19.006 | 5.229 | 1.00 | 27.80 | C |
| ATOM | 500 | O | LEU | 85 | −5.923 | 18.105 | 5.500 | 1.00 | 26.59 | O |
| ATOM | 501 | N | PHE | 86 | −4.386 | 19.618 | 6.149 | 1.00 | 25.85 | N |
| ATOM | 502 | CA | PHE | 86 | −4.466 | 19.262 | 7.561 | 1.00 | 25.42 | C |
| ATOM | 503 | CB | PHE | 86 | −3.153 | 19.569 | 8.288 | 1.00 | 25.61 | C |
| ATOM | 504 | CG | PHE | 86 | −1.984 | 18.745 | 7.833 | 1.00 | 24.56 | C |
| ATOM | 505 | CD1 | PHE | 86 | −0.723 | 18.972 | 8.362 | 1.00 | 25.69 | C |
| ATOM | 506 | CD2 | PHE | 86 | −2.158 | 17.687 | 6.955 | 1.00 | 25.22 | C |
| ATOM | 507 | CE1 | PHE | 86 | 0.343 | 18.158 | 8.033 | 1.00 | 24.12 | C |
| ATOM | 508 | CE2 | PHE | 86 | −1.096 | 16.866 | 6.620 | 1.00 | 24.92 | C |
| ATOM | 509 | CZ | PHE | 86 | 0.156 | 17.100 | 7.161 | 1.00 | 25.70 | C |
| ATOM | 510 | C | PHE | 86 | −5.626 | 19.871 | 8.342 | 1.00 | 25.22 | C |
| ATOM | 511 | O | PHE | 86 | −5.984 | 19.374 | 9.403 | 1.00 | 27.68 | O |
| ATOM | 512 | N | GLY | 87 | −6.220 | 20.936 | 7.821 | 1.00 | 25.48 | N |
| ATOM | 513 | CA | GLY | 87 | −7.308 | 21.572 | 8.538 | 1.00 | 24.46 | C |
| ATOM | 514 | C | GLY | 87 | −6.846 | 22.301 | 9.793 | 1.00 | 24.27 | C |
| ATOM | 515 | O | GLY | 87 | −7.577 | 22.374 | 10.778 | 1.00 | 25.23 | O |
| ATOM | 516 | N | VAL | 88 | −5.628 | 22.835 | 9.763 | 1.00 | 23.15 | N |
| ATOM | 517 | CA | VAL | 88 | −5.067 | 23.582 | 10.892 | 1.00 | 21.50 | C |
| ATOM | 518 | CB | VAL | 88 | −4.183 | 22.697 | 11.837 | 1.00 | 22.47 | C |
| ATOM | 519 | CG1 | VAL | 88 | −5.014 | 21.573 | 12.444 | 1.00 | 23.92 | C |
| ATOM | 520 | CG2 | VAL | 88 | −2.985 | 22.136 | 11.082 | 1.00 | 21.60 | C |
| ATOM | 521 | C | VAL | 88 | −4.200 | 24.704 | 10.341 | 1.00 | 19.98 | C |
| ATOM | 522 | O | VAL | 88 | −3.544 | 24.541 | 9.317 | 1.00 | 19.52 | O |
| ATOM | 523 | N | PRO | 89 | −4.196 | 25.871 | 11.001 | 1.00 | 21.92 | N |
| ATOM | 524 | CD | PRO | 89 | −4.796 | 26.279 | 12.289 | 1.00 | 20.40 | C |
| ATOM | 525 | CA | PRO | 89 | −3.366 | 26.958 | 10.488 | 1.00 | 21.32 | C |
| ATOM | 526 | CB | PRO | 89 | −4.009 | 28.164 | 11.135 | 1.00 | 21.47 | C |
| ATOM | 527 | CG | PRO | 89 | −4.109 | 27.664 | 12.548 | 1.00 | 21.05 | C |
| ATOM | 528 | C | PRO | 89 | −1.881 | 26.800 | 10.808 | 1.00 | 21.71 | C |
| ATOM | 529 | O | PRO | 89 | −1.029 | 27.350 | 10.114 | 1.00 | 20.80 | O |
| ATOM | 530 | N | SER | 90 | −1.579 | 26.025 | 11.845 | 1.00 | 22.01 | N |
| ATOM | 531 | CA | SER | 90 | −0.197 | 25.803 | 12.257 | 1.00 | 24.39 | C |
| ATOM | 532 | CB | SER | 90 | 0.475 | 27.107 | 12.704 | 1.00 | 25.95 | C |
| ATOM | 533 | OG | SER | 90 | −0.191 | 27.688 | 13.806 | 1.00 | 30.18 | O |
| ATOM | 534 | C | SER | 90 | −0.076 | 24.728 | 13.329 | 1.00 | 23.46 | C |
| ATOM | 535 | O | SER | 90 | −1.048 | 24.407 | 14.010 | 1.00 | 25.46 | O |
| ATOM | 536 | N | PHE | 91 | 1.119 | 24.161 | 13.462 | 1.00 | 23.68 | N |
| ATOM | 537 | CA | PHE | 91 | 1.375 | 23.126 | 14.463 | 1.00 | 22.17 | C |
| ATOM | 538 | CB | PHE | 91 | 0.869 | 21.755 | 14.002 | 1.00 | 22.00 | C |
| ATOM | 539 | CG | PHE | 91 | 1.527 | 21.265 | 12.739 | 1.00 | 23.50 | C |
| ATOM | 540 | CD1 | PHE | 91 | 1.133 | 21.751 | 11.497 | 1.00 | 23.67 | C |
| ATOM | 541 | CD2 | PHE | 91 | 2.575 | 20.360 | 12.798 | 1.00 | 21.96 | C |
| ATOM | 542 | CE1 | PHE | 91 | 1.775 | 21.342 | 10.339 | 1.00 | 22.42 | C |
| ATOM | 543 | CE2 | PHE | 91 | 3.220 | 19.949 | 11.645 | 1.00 | 23.74 | C |
| ATOM | 544 | CZ | PHE | 91 | 2.818 | 20.442 | 10.414 | 1.00 | 22.47 | C |
| ATOM | 545 | C | PHE | 91 | 2.862 | 23.032 | 14.812 | 1.00 | 21.03 | C |
| ATOM | 546 | O | PHE | 91 | 3.700 | 23.714 | 14.225 | 1.00 | 22.64 | O |

TABLE 4-continued

| 1 | 2 | 3 | 4 | 5 | 6 | 7 | 8 | 9 | 10 | 11 |
|---|---|---|---|---|---|---|---|---|---|---|
| ATOM | 547 | N | SER | 92 | 3.162 | 22.177 | 15.781 | 1.00 | 18.50 | N |
| ATOM | 548 | CA | SER | 92 | 4.517 | 21.909 | 16.234 | 1.00 | 17.97 | C |
| ATOM | 549 | CB | SER | 92 | 4.626 | 21.948 | 17.750 | 1.00 | 17.24 | C |
| ATOM | 550 | OG | SER | 92 | 5.941 | 21.622 | 18.147 | 1.00 | 15.01 | O |
| ATOM | 551 | C | SER | 92 | 4.938 | 20.538 | 15.718 | 1.00 | 19.41 | C |
| ATOM | 552 | O | SER | 92 | 4.134 | 19.607 | 15.711 | 1.00 | 16.66 | O |
| ATOM | 553 | N | VAL | 93 | 6.186 | 20.417 | 15.273 | 1.00 | 19.68 | N |
| ATOM | 554 | CA | VAL | 93 | 6.676 | 19.142 | 14.766 | 1.00 | 20.81 | C |
| ATOM | 555 | CB | VAL | 93 | 8.052 | 19.290 | 14.079 | 1.00 | 22.21 | C |
| ATOM | 556 | CG1 | VAL | 93 | 8.008 | 20.418 | 13.061 | 1.00 | 21.22 | C |
| ATOM | 557 | CG2 | VAL | 93 | 9.134 | 19.522 | 15.119 | 1.00 | 20.18 | C |
| ATOM | 558 | C | VAL | 93 | 6.819 | 18.131 | 15.897 | 1.00 | 21.81 | C |
| ATOM | 559 | O | VAL | 93 | 7.136 | 16.969 | 15.662 | 1.00 | 24.55 | O |
| ATOM | 560 | N | LYS | 94 | 6.579 | 18.568 | 17.127 | 1.00 | 22.80 | N |
| ATOM | 561 | CA | LYS | 94 | 6.696 | 17.670 | 18.267 | 1.00 | 23.16 | C |
| ATOM | 562 | CB | LYS | 94 | 7.400 | 18.364 | 19.431 | 1.00 | 25.99 | C |
| ATOM | 563 | CG | LYS | 94 | 6.681 | 19.571 | 19.966 | 1.00 | 29.97 | C |
| ATOM | 564 | CD | LYS | 94 | 7.486 | 20.206 | 21.088 | 1.00 | 34.85 | C |
| ATOM | 565 | CE | LYS | 94 | 8.855 | 20.641 | 20.553 | 1.00 | 34.82 | C |
| ATOM | 566 | NZ | LYS | 94 | 9.710 | 21.284 | 21.583 | 1.00 | 37.75 | N |
| ATOM | 567 | C | LYS | 94 | 5.343 | 17.088 | 18.669 | 1.00 | 20.95 | C |
| ATOM | 568 | O | LYS | 94 | 5.253 | 16.252 | 19.570 | 1.00 | 19.08 | O |
| ATOM | 569 | N | GLU | 95 | 4.297 | 17.538 | 17.983 | 1.00 | 19.27 | N |
| ATOM | 570 | CA | GLU | 95 | 2.937 | 17.055 | 18.212 | 1.00 | 18.96 | C |
| ATOM | 571 | CB | GLU | 95 | 1.919 | 18.145 | 17.873 | 1.00 | 18.81 | C |
| ATOM | 572 | CG | GLU | 95 | 2.046 | 19.387 | 18.743 | 1.00 | 21.00 | C |
| ATOM | 573 | CD | GLU | 95 | 1.017 | 20.418 | 18.319 | 1.00 | 22.03 | C |
| ATOM | 574 | OE1 | GLU | 95 | −0.095 | 20.444 | 18.888 | 1.00 | 20.78 | O |
| ATOM | 575 | OE2 | GLU | 95 | 1.338 | 21.228 | 17.429 | 1.00 | 23.38 | O |
| ATOM | 576 | C | GLU | 95 | 2.751 | 15.823 | 17.334 | 1.00 | 18.97 | C |
| ATOM | 577 | O | GLU | 95 | 2.008 | 15.853 | 16.359 | 1.00 | 17.30 | O |
| ATOM | 578 | N | HIS | 96 | 3.426 | 14.735 | 17.698 | 1.00 | 20.49 | N |
| ATOM | 579 | CA | HIS | 96 | 3.374 | 13.503 | 16.919 | 1.00 | 22.53 | C |
| ATOM | 580 | CB | HIS | 96 | 4.357 | 12.468 | 17.460 | 1.00 | 22.80 | C |
| ATOM | 581 | CG | HIS | 96 | 5.778 | 12.924 | 17.429 | 1.00 | 22.99 | C |
| ATOM | 582 | CD2 | HIS | 96 | 6.331 | 14.078 | 16.987 | 1.00 | 24.26 | C |
| ATOM | 583 | ND1 | HIS | 96 | 6.818 | 12.157 | 17.903 | 1.00 | 22.37 | N |
| ATOM | 584 | CE1 | HIS | 96 | 7.952 | 12.818 | 17.754 | 1.00 | 25.34 | C |
| ATOM | 585 | NE2 | HIS | 96 | 7.683 | 13.987 | 17.200 | 1.00 | 25.87 | N |
| ATOM | 586 | C | HIS | 96 | 2.016 | 12.865 | 16.703 | 1.00 | 23.09 | C |
| ATOM | 587 | O | HIS | 96 | 1.741 | 12.375 | 15.611 | 1.00 | 25.80 | O |
| ATOM | 588 | N | ARG | 97 | 1.153 | 12.871 | 17.712 | 1.00 | 23.57 | N |
| ATOM | 589 | CA | ARG | 97 | −0.145 | 12.253 | 17.509 | 1.00 | 22.11 | C |
| ATOM | 590 | CB | ARG | 97 | −0.852 | 11.940 | 18.829 | 1.00 | 22.67 | C |
| ATOM | 591 | CG | ARG | 97 | −2.215 | 11.295 | 18.608 | 1.00 | 25.29 | C |
| ATOM | 592 | CD | ARG | 97 | −2.946 | 10.947 | 19.895 | 1.00 | 24.16 | C |
| ATOM | 593 | NE | ARG | 97 | −4.238 | 10.344 | 19.586 | 1.00 | 25.87 | N |
| ATOM | 594 | CZ | ARG | 97 | −5.067 | 9.819 | 20.481 | 1.00 | 25.09 | C |
| ATOM | 595 | NH1 | ARG | 97 | −4.748 | 9.801 | 21.769 | 1.00 | 25.97 | N |
| ATOM | 596 | NH2 | ARG | 97 | −6.236 | 9.339 | 20.086 | 1.00 | 24.37 | N |
| ATOM | 597 | C | ARG | 97 | −1.019 | 13.095 | 16.596 | 1.00 | 20.82 | C |
| ATOM | 598 | O | ARG | 97 | −1.837 | 12.563 | 15.849 | 1.00 | 22.99 | O |
| ATOM | 599 | N | LYS | 98 | −0.833 | 14.409 | 16.638 | 1.00 | 19.91 | N |
| ATOM | 600 | CA | LYS | 98 | −1.614 | 15.294 | 15.787 | 1.00 | 19.73 | C |
| ATOM | 601 | CB | LYS | 98 | −1.487 | 16.749 | 16.228 | 1.00 | 20.60 | C |
| ATOM | 602 | CG | LYS | 98 | −2.252 | 17.723 | 15.331 | 1.00 | 23.23 | C |
| ATOM | 603 | CD | LYS | 98 | −2.091 | 19.164 | 15.794 | 1.00 | 23.00 | C |
| ATOM | 604 | CE | LYS | 98 | −2.611 | 19.344 | 17.205 | 1.00 | 24.33 | C |
| ATOM | 605 | NZ | LYS | 98 | −2.463 | 20.740 | 17.674 | 1.00 | 25.97 | N |
| ATOM | 606 | C | LYS | 98 | −1.181 | 15.160 | 14.331 | 1.00 | 18.95 | C |
| ATOM | 607 | O | LYS | 98 | −2.013 | 15.142 | 13.423 | 1.00 | 18.06 | O |
| ATOM | 608 | N | ILE | 99 | 0.126 | 15.047 | 14.120 | 1.00 | 16.71 | N |
| ATOM | 609 | CA | ILE | 99 | 0.664 | 14.935 | 12.777 | 1.00 | 18.14 | C |
| ATOM | 610 | CB | ILE | 99 | 2.205 | 15.049 | 12.794 | 1.00 | 18.88 | C |
| ATOM | 611 | CG2 | ILE | 99 | 2.764 | 14.887 | 11.382 | 1.00 | 17.52 | C |
| ATOM | 612 | CG1 | ILE | 99 | 2.612 | 16.408 | 13.372 | 1.00 | 16.52 | C |
| ATOM | 613 | CD1 | ILE | 99 | 4.102 | 16.610 | 13.445 | 1.00 | 18.05 | C |
| ATOM | 614 | C | ILE | 99 | 0.252 | 13.632 | 12.105 | 1.00 | 19.52 | C |
| ATOM | 615 | O | ILE | 99 | −0.096 | 13.633 | 10.929 | 1.00 | 20.84 | O |
| ATOM | 616 | N | TYR | 100 | 0.278 | 12.520 | 12.836 | 1.00 | 21.34 | N |
| ATOM | 617 | CA | TYR | 100 | −0.140 | 11.258 | 12.234 | 1.00 | 21.76 | C |
| ATOM | 618 | CB | TYR | 100 | 0.388 | 10.029 | 12.982 | 1.00 | 20.52 | C |
| ATOM | 619 | CG | TYR | 100 | 1.880 | 9.828 | 12.897 | 1.00 | 21.94 | C |
| ATOM | 620 | CD1 | TYR | 100 | 2.456 | 9.359 | 11.724 | 1.00 | 22.57 | C |
| ATOM | 621 | CE1 | TYR | 100 | 3.812 | 9.131 | 11.633 | 1.00 | 22.83 | C |
| ATOM | 622 | CD2 | TYR | 100 | 2.708 | 10.070 | 13.982 | 1.00 | 22.53 | C |
| ATOM | 623 | CE2 | TYR | 100 | 4.068 | 9.847 | 13.901 | 1.00 | 22.55 | C |
| ATOM | 624 | CZ | TYR | 100 | 4.613 | 9.374 | 12.724 | 1.00 | 22.83 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 625 | OH | TYR | 100 | 5.962 | 9.125 | 12.642 | 1.00 | 24.71 | O |
| ATOM | 626 | C | TYR | 100 | −1.637 | 11.164 | 12.051 | 1.00 | 22.16 | C |
| ATOM | 627 | O | TYR | 100 | −2.120 | 10.375 | 11.240 | 1.00 | 20.79 | O |
| ATOM | 628 | N | THR | 101 | −2.375 | 11.980 | 12.789 | 1.00 | 22.43 | N |
| ATOM | 629 | CA | THR | 101 | −3.818 | 11.949 | 12.659 | 1.00 | 20.93 | C |
| ATOM | 630 | CB | THR | 101 | −4.501 | 12.622 | 13.867 | 1.00 | 20.70 | C |
| ATOM | 631 | OG1 | THR | 101 | −4.220 | 11.862 | 15.049 | 1.00 | 21.16 | O |
| ATOM | 632 | CG2 | THR | 101 | −6.013 | 12.703 | 13.661 | 1.00 | 19.19 | C |
| ATOM | 633 | C | THR | 101 | −4.176 | 12.684 | 11.382 | 1.00 | 20.33 | C |
| ATOM | 634 | O | THR | 101 | −4.980 | 12.199 | 10.583 | 1.00 | 19.32 | O |
| ATOM | 635 | N | MET | 102 | −3.551 | 13.843 | 11.186 | 1.00 | 20.81 | N |
| ATOM | 636 | CA | MET | 102 | −3.803 | 14.664 | 10.006 | 1.00 | 21.77 | C |
| ATOM | 637 | CB | MET | 102 | −3.128 | 16.031 | 10.119 | 1.00 | 22.96 | C |
| ATOM | 638 | CG | MET | 102 | −3.563 | 16.875 | 11.305 | 1.00 | 25.26 | C |
| ATOM | 639 | SD | MET | 102 | −2.691 | 18.457 | 11.303 | 1.00 | 26.02 | S |
| ATOM | 640 | CE | MET | 102 | −1.054 | 17.961 | 11.843 | 1.00 | 25.10 | C |
| ATOM | 641 | C | MET | 102 | −3.326 | 13.982 | 8.735 | 1.00 | 21.84 | C |
| ATOM | 642 | O | MET | 102 | −3.959 | 14.101 | 7.689 | 1.00 | 22.57 | O |
| ATOM | 643 | N | ILE | 103 | −2.215 | 13.259 | 8.828 | 1.00 | 20.60 | N |
| ATOM | 644 | CA | ILE | 103 | −1.672 | 12.580 | 7.664 | 1.00 | 20.83 | C |
| ATOM | 645 | CB | ILE | 103 | −0.220 | 12.115 | 7.937 | 1.00 | 21.14 | C |
| ATOM | 646 | CG2 | ILE | 103 | 0.262 | 11.190 | 6.832 | 1.00 | 20.31 | C |
| ATOM | 647 | CG1 | ILE | 103 | 0.685 | 13.350 | 8.046 | 1.00 | 20.27 | C |
| ATOM | 648 | CD1 | ILE | 103 | 2.144 | 13.056 | 8.323 | 1.00 | 20.70 | C |
| ATOM | 649 | C | ILE | 103 | −2.568 | 11.414 | 7.248 | 1.00 | 20.54 | C |
| ATOM | 650 | O | ILE | 103 | −2.897 | 11.288 | 6.072 | 1.00 | 20.36 | O |
| ATOM | 651 | N | TYR | 104 | −2.974 | 10.569 | 8.194 | 1.00 | 20.06 | N |
| ATOM | 652 | CA | TYR | 104 | −3.879 | 9.475 | 7.843 | 1.00 | 18.57 | C |
| ATOM | 653 | CB | TYR | 104 | −4.007 | 8.411 | 8.939 | 1.00 | 17.25 | C |
| ATOM | 654 | CG | TYR | 104 | −2.810 | 7.512 | 9.145 | 1.00 | 18.10 | C |
| ATOM | 655 | CD1 | TYR | 104 | −2.836 | 6.214 | 8.649 | 1.00 | 19.08 | C |
| ATOM | 656 | CE1 | TYR | 104 | −1.795 | 5.339 | 8.849 | 1.00 | 18.97 | C |
| ATOM | 657 | CD2 | TYR | 104 | −1.688 | 7.920 | 9.851 | 1.00 | 17.72 | C |
| ATOM | 658 | CE2 | TYR | 104 | −0.621 | 7.043 | 10.059 | 1.00 | 20.75 | C |
| ATOM | 659 | CZ | TYR | 104 | −0.691 | 5.746 | 9.551 | 1.00 | 20.88 | C |
| ATOM | 660 | OH | TYR | 104 | 0.323 | 4.835 | 9.749 | 1.00 | 19.81 | O |
| ATOM | 661 | C | TYR | 104 | −5.259 | 9.907 | 7.370 | 1.00 | 19.95 | C |
| ATOM | 662 | O | TYR | 104 | −5.991 | 9.105 | 6.794 | 1.00 | 21.99 | O |
| ATOM | 663 | N | ARG | 105 | −5.626 | 11.162 | 7.602 | 1.00 | 17.59 | N |
| ATOM | 664 | CA | ARG | 105 | −6.915 | 11.623 | 7.121 | 1.00 | 17.20 | C |
| ATOM | 665 | CB | ARG | 105 | −7.491 | 12.768 | 7.959 | 1.00 | 16.31 | C |
| ATOM | 666 | CG | ARG | 105 | −7.847 | 12.404 | 9.383 | 1.00 | 17.10 | C |
| ATOM | 667 | CD | ARG | 105 | −8.413 | 13.609 | 10.125 | 1.00 | 16.21 | C |
| ATOM | 668 | NE | ARG | 105 | −8.799 | 13.284 | 11.495 | 1.00 | 16.48 | N |
| ATOM | 669 | CZ | ARG | 105 | −9.313 | 14.159 | 12.358 | 1.00 | 19.13 | C |
| ATOM | 670 | NH1 | ARG | 105 | −9.495 | 15.427 | 12.003 | 1.00 | 17.52 | N |
| ATOM | 671 | NH2 | ARG | 105 | −9.676 | 13.760 | 13.572 | 1.00 | 19.14 | N |
| ATOM | 672 | C | ARG | 105 | −6.798 | 12.023 | 5.663 | 1.00 | 17.20 | C |
| ATOM | 673 | O | ARG | 105 | −7.789 | 12.336 | 5.021 | 1.00 | 16.63 | O |
| ATOM | 674 | N | ASN | 106 | −5.574 | 11.989 | 5.147 | 1.00 | 19.37 | N |
| ATOM | 675 | CA | ASN | 106 | −5.302 | 12.366 | 3.766 | 1.00 | 20.38 | C |
| ATOM | 676 | CB | ASN | 106 | −4.507 | 13.663 | 3.704 | 1.00 | 20.43 | C |
| ATOM | 677 | CG | ASN | 106 | −5.251 | 14.812 | 4.339 | 1.00 | 20.58 | C |
| ATOM | 678 | OD1 | ASN | 106 | −6.143 | 15.390 | 3.723 | 1.00 | 23.31 | O |
| ATOM | 679 | ND2 | ASN | 106 | −4.885 | 15.160 | 5.562 | 1.00 | 17.80 | N |
| ATOM | 680 | C | ASN | 106 | −4.659 | 11.281 | 2.919 | 1.00 | 21.95 | C |
| ATOM | 681 | O | ASN | 106 | −4.027 | 11.558 | 1.896 | 1.00 | 20.86 | O |
| ATOM | 682 | N | LEU | 107 | −4.823 | 10.042 | 3.361 | 1.00 | 21.77 | N |
| ATOM | 683 | CA | LEU | 107 | −4.264 | 8.899 | 2.666 | 1.00 | 21.73 | C |
| ATOM | 684 | CB | LEU | 107 | −2.737 | 8.860 | 2.832 | 1.00 | 20.40 | C |
| ATOM | 685 | CG | LEU | 107 | −2.118 | 8.762 | 4.235 | 1.00 | 19.18 | C |
| ATOM | 686 | CD1 | LEU | 107 | −2.558 | 7.498 | 4.968 | 1.00 | 18.29 | C |
| ATOM | 687 | CD2 | LEU | 107 | −0.602 | 8.811 | 4.171 | 1.00 | 16.48 | C |
| ATOM | 688 | C | LEU | 107 | −4.943 | 7.622 | 3.150 | 1.00 | 24.57 | C |
| ATOM | 689 | O | LEU | 107 | −5.476 | 7.574 | 4.261 | 1.00 | 26.59 | O |
| ATOM | 690 | N | VAL | 108 | −4.950 | 6.604 | 2.300 | 1.00 | 24.85 | N |
| ATOM | 691 | CA | VAL | 108 | −5.535 | 5.314 | 2.637 | 1.00 | 23.27 | C |
| ATOM | 692 | CB | VAL | 108 | −6.585 | 4.884 | 1.594 | 1.00 | 25.05 | C |
| ATOM | 693 | CG1 | VAL | 108 | −6.727 | 3.374 | 1.592 | 1.00 | 26.97 | C |
| ATOM | 694 | CG2 | VAL | 108 | −7.923 | 5.523 | 1.917 | 1.00 | 23.65 | C |
| ATOM | 695 | C | VAL | 108 | −4.435 | 4.259 | 2.704 | 1.00 | 22.36 | C |
| ATOM | 696 | O | VAL | 108 | −3.534 | 4.240 | 1.866 | 1.00 | 23.25 | O |
| ATOM | 697 | N | VAL | 109 | −4.494 | 3.397 | 3.714 | 1.00 | 21.67 | N |
| ATOM | 698 | CA | VAL | 109 | −3.504 | 2.336 | 3.865 | 1.00 | 20.80 | C |
| ATOM | 699 | CB | VAL | 109 | −3.455 | 1.801 | 5.316 | 1.00 | 19.45 | C |
| ATOM | 700 | CG1 | VAL | 109 | −2.544 | 0.583 | 5.389 | 1.00 | 17.84 | C |
| ATOM | 701 | CG2 | VAL | 109 | −2.941 | 2.892 | 6.256 | 1.00 | 18.14 | C |
| ATOM | 702 | C | VAL | 109 | −3.787 | 1.173 | 2.910 | 1.00 | 21.74 | C |

TABLE 4-continued

| 1 | 2 | 3 | 4 | 5 | 6 | 7 | 8 | 9 | 10 | 11 |
|---|---|---|---|---|---|---|---|---|---|---|
| ATOM | 703 | O | VAL | 109 | −4.915 | 0.696 | 2.811 | 1.00 | 22.57 | O |
| ATOM | 704 | N | VAL | 110 | −2.754 | 0.739 | 2.195 | 1.00 | 22.61 | N |
| ATOM | 705 | CA | VAL | 110 | −2.871 | −0.365 | 1.249 | 1.00 | 23.79 | C |
| ATOM | 706 | CB | VAL | 110 | −1.791 | −0.279 | 0.158 | 1.00 | 22.99 | C |
| ATOM | 707 | CG1 | VAL | 110 | −1.997 | −1.377 | −0.864 | 1.00 | 23.58 | C |
| ATOM | 708 | CG2 | VAL | 110 | −1.828 | 1.081 | −0.495 | 1.00 | 24.01 | C |
| ATOM | 709 | C | VAL | 110 | −2.722 | −1.703 | 1.961 | 1.00 | 24.53 | C |
| ATOM | 710 | O | VAL | 110 | −3.639 | −2.521 | 1.944 | 1.00 | 28.90 | O |
| ATOM | 711 | OH2 | WAT | 901 | 6.275 | 31.112 | 15.565 | 1.00 | 15.47 | O |
| ATOM | 712 | OH2 | WAT | 902 | 0.081 | 30.036 | 10.221 | 1.00 | 17.32 | O |
| ATOM | 713 | OH2 | WAT | 903 | 0.127 | 15.519 | 19.408 | 1.00 | 7.93 | O |
| ATOM | 714 | OH2 | WAT | 904 | 7.030 | 2.992 | 5.951 | 1.00 | 1.12 | O |
| ATOM | 715 | OH2 | WAT | 905 | −8.260 | 9.003 | 4.793 | 1.00 | 16.56 | O |
| ATOM | 716 | OH2 | WAT | 906 | −0.287 | 23.410 | 17.398 | 1.00 | 20.45 | O |
| ATOM | 717 | OH2 | WAT | 907 | 11.907 | 15.641 | 5.635 | 1.00 | 12.75 | O |
| ATOM | 718 | OH2 | WAT | 908 | 6.231 | 3.121 | −2.803 | 1.00 | 30.59 | O |
| ATOM | 719 | OH2 | WAT | 909 | 14.427 | 27.473 | −1.777 | 1.00 | 32.06 | O |
| ATOM | 720 | OH2 | WAT | 910 | 1.367 | 29.323 | 5.015 | 1.00 | 30.79 | O |
| ATOM | 721 | OH2 | WAT | 911 | −3.588 | −4.814 | 0.678 | 1.00 | 24.03 | O |
| ATOM | 722 | OH2 | WAT | 912 | 3.828 | 6.836 | −11.268 | 1.00 | 35.90 | O |
| ATOM | 723 | OH2 | WAT | 913 | 8.152 | 2.609 | 8.906 | 1.00 | 34.73 | O |
| ATOM | 724 | OH2 | WAT | 914 | 2.691 | 4.733 | 10.966 | 1.00 | 33.58 | O |
| ATOM | 725 | OH2 | WAT | 916 | −5.458 | 26.444 | 7.758 | 1.00 | 45.56 | O |
| ATOM | 726 | OH2 | WAT | 917 | −8.076 | 13.274 | 16.506 | 1.00 | 48.77 | O |
| ATOM | 727 | OH2 | WAT | 918 | −7.491 | 17.267 | 10.217 | 1.00 | 40.88 | O |
| ATOM | 728 | OH2 | WAT | 919 | −3.101 | 7.362 | −4.725 | 1.00 | 53.52 | O |
| ATOM | 729 | OH2 | WAT | 920 | 1.887 | 19.751 | −8.003 | 1.00 | 32.67 | O |
| ATOM | 730 | OH2 | WAT | 921 | −8.379 | 15.505 | −1.840 | 1.00 | 19.94 | O |
| ATOM | 731 | OH2 | WAT | 922 | 12.181 | 19.059 | −4.016 | 1.00 | 25.92 | O |
| ATOM | 732 | OH2 | WAT | 923 | −8.305 | 16.544 | 7.450 | 1.00 | 29.31 | O |
| ATOM | 733 | OH2 | WAT | 924 | −10.379 | 14.823 | 6.843 | 1.00 | 19.67 | O |
| ATOM | 734 | C1 | SCH | 999 | 14.935 | 15.343 | 10.195 | 1.00 | 58.18 | C |
| ATOM | 735 | C2 | SCH | 999 | 13.897 | 15.023 | 11.252 | 1.00 | 58.15 | C |
| ATOM | 736 | O1 | SCH | 999 | 14.212 | 14.616 | 12.373 | 1.00 | 58.19 | O |
| ATOM | 737 | N1 | SCH | 999 | 12.629 | 15.230 | 10.832 | 1.00 | 57.26 | N |
| ATOM | 738 | C3 | SCH | 999 | 11.571 | 15.353 | 11.839 | 1.00 | 54.45 | C |
| ATOM | 739 | C4 | SCH | 999 | 10.855 | 14.032 | 12.129 | 1.00 | 55.03 | C |
| ATOM | 740 | O2 | SCH | 999 | 11.268 | 12.976 | 11.642 | 1.00 | 55.46 | O |
| ATOM | 741 | N2 | SCH | 999 | 9.780 | 14.154 | 12.934 | 1.00 | 56.28 | N |
| ATOM | 742 | C5 | SCH | 999 | 9.102 | 12.951 | 13.392 | 1.00 | 58.10 | C |
| ATOM | 743 | C6 | SCH | 999 | 10.025 | 12.199 | 14.360 | 1.00 | 59.43 | C |
| ATOM | 744 | O3 | SCH | 999 | 10.530 | 11.115 | 14.068 | 1.00 | 59.32 | O |
| ATOM | 745 | N3 | SCH | 999 | 10.203 | 12.847 | 15.527 | 1.00 | 61.53 | N |
| ATOM | 746 | C7 | SCH | 999 | 11.400 | 12.542 | 16.310 | 1.00 | 62.93 | C |
| ATOM | 747 | C8 | SCH | 999 | 11.113 | 11.660 | 17.534 | 1.00 | 62.40 | C |
| ATOM | 748 | O4 | SCH | 999 | 11.912 | 11.709 | 18.416 | 1.00 | 60.48 | O |
| ATOM | 749 | O5 | SCH | 999 | 10.616 | 10.479 | 17.100 | 1.00 | 62.41 | O |
| ATOM | 750 | C9 | SCH | 999 | 10.586 | 16.476 | 11.453 | 1.00 | 49.76 | C |
| ATOM | 751 | C10 | SCH | 999 | 12.105 | 13.839 | 16.718 | 1.00 | 64.21 | C |
| ATOM | 752 | C11 | SCH | 999 | 13.629 | 13.756 | 16.707 | 1.00 | 65.67 | C |
| ATOM | 753 | C12 | SCH | 999 | 14.196 | 14.646 | 17.803 | 1.00 | 66.24 | C |
| ATOM | 754 | O6 | SCH | 999 | 14.526 | 15.775 | 17.594 | 1.00 | 66.36 | O |
| ATOM | 755 | O7 | SCH | 999 | 14.290 | 14.052 | 19.016 | 1.00 | 65.17 | O |
| ATOM | 756 | C13 | SCH | 999 | 9.685 | 16.072 | 10.295 | 1.00 | 46.19 | C |
| ATOM | 757 | C14 | SCH | 999 | 8.313 | 16.472 | 10.068 | 1.00 | 43.66 | C |
| ATOM | 758 | C15 | SCH | 999 | 7.872 | 15.829 | 8.846 | 1.00 | 42.20 | C |
| ATOM | 759 | N4 | SCH | 999 | 8.951 | 15.079 | 8.368 | 1.00 | 43.85 | N |
| ATOM | 760 | C16 | SCH | 999 | 10.006 | 15.227 | 9.219 | 1.00 | 44.78 | C |
| ATOM | 761 | C17 | SCH | 999 | 7.411 | 17.318 | 10.780 | 1.00 | 43.03 | C |
| ATOM | 762 | C18 | SCH | 999 | 6.085 | 17.525 | 10.294 | 1.00 | 39.51 | C |
| ATOM | 763 | C19 | SCH | 999 | 5.651 | 16.887 | 9.095 | 1.00 | 39.12 | C |
| ATOM | 764 | C20 | SCH | 999 | 6.542 | 16.041 | 8.370 | 1.00 | 40.06 | C |
| ATOM | 765 | CL1 | SCH | 999 | 4.034 | 17.133 | 8.522 | 1.00 | 34.69 | CL |
| ATOM | 766 | C21 | SCH | 999 | 8.779 | 12.041 | 12.203 | 1.00 | 57.67 | C |
| ATOM | 767 | C22 | SCH | 999 | 7.820 | 13.335 | 14.135 | 1.00 | 58.12 | C |
| ATOM | 768 | C23 | SCH | 999 | 6.793 | 13.968 | 13.201 | 1.00 | 56.83 | C |
| ATOM | 769 | C24 | SCH | 999 | 7.749 | 12.676 | 11.271 | 1.00 | 57.14 | C |
| ATOM | 770 | C25 | SCH | 999 | 6.477 | 13.064 | 12.015 | 1.00 | 56.55 | C |
| END | | | | | | | | | | |

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A nucleic acid encoding a polypeptide comprising an amino acid sequence selected from the group consisting of SEQ ID NO: 6, SEQ ID NO: 10 and SEQ ID NO: 12.

2. The nucleic acid according to claim 1 comprising a nucleotide sequence selected from the group consisting of SEQ ID NO: 5, SEQ ID NO: 9, and SEQ ID NO: 11.

3. An expression vector comprising the nucleic acid according to claim 2, wherein said expression vector further comprises a transcriptional control sequence operatively linked to the nucleic acid.

4. A host cell comprising the expression vector according to claim 3.

5. A method for producing a modified Hdm2 protein comprising an amino acid sequence selected from the group consisting of SEQ ID NO: 6, SEQ ID NO: 10 and SEQ ID NO: 12, comprising culturing the host cell according to claim 4 in a culture medium under conditions in which the nucleic acid encoding the modified Hdm2 protein is expressed, thereby producing the modified Hdm2 protein.

6. The method according to claim 5 wherein the host cell is an *Escherichia coli* cell.

7. A method for obtaining a purified modified Hdm2 protein comprising an amino acid sequence selected from the group consisting of SEQ ID NO: 6, SEQ ID NO: 10 and SEQ ID NO: 12, comprising culturing the host cell of claim 4 in a culture medium under conditions in which the nucleic acid encoding the modified Hdm2 protein is expressed to thereby produce the modified Hdm2 protein; and purifying the modified Hdm2 protein from the culture medium.

* * * * *

SEQUENCE LISTING

<160> NUMBER OF SEQ ID NOS: 18

<210> SEQ ID NO 1
<211> LENGTH: 327
<212> TYPE: DNA
<213> ORGANISM: Homo sapiens

<400> SEQUENCE: 1
tcacagattc cagcttcgga acaagagacc ctggttagac caaagccatt gcttttgaag    60
ttattaaagt ctgttggtgc acaaaaagac acttatacta tgaaagaggt tcttttttat   120
cttggccagt atattatgac taaacgatta tatgatgaga agcaacaaca tattgtatat   180
tgttcaaatg atcttctagg agatttgttt ggcgtgccaa gcttctctgt gaaagagcac   240
aggaaaatat ataccatgat ctacaggaac ttggtagtag tcaatcagca ggaatcatcg   300
gactcaggta catctgtgag tgagaac                                      327

<210> SEQ ID NO 2
<211> LENGTH: 109
<212> TYPE: PRT
<213> ORGANISM: Homo sapiens

<400> SEQUENCE: 2

Ser Gln Ile Pro Ala Ser Glu Gln Glu Thr Leu Val Arg Pro Lys Pro
1               5                  10                  15

Leu Leu Leu Lys Leu Leu Lys Ser Val Gly Ala Gln Lys Asp Thr Tyr
            20                  25                  30

Thr Met Lys Glu Val Leu Phe Tyr Leu Gly Gln Tyr Ile Met Thr Lys
        35                  40                  45

Arg Leu Tyr Asp Glu Lys Gln Gln His Ile Val Tyr Cys Ser Asn Asp
    50                  55                  60

Leu Leu Gly Asp Leu Phe Gly Val Pro Ser Phe Ser Val Lys Glu His
65                  70                  75                  80

Arg Lys Ile Tyr Thr Met Ile Tyr Arg Asn Leu Val Val Val Asn Gln
                85                  90                  95

Gln Glu Ser Ser Asp Ser Gly Thr Ser Val Ser Glu Asn
            100                 105

<210> SEQ ID NO 3
<211> LENGTH: 327
<212> TYPE: DNA
<213> ORGANISM: Homo sapiens
<220> FEATURE:
<221> NAME/KEY: misc_feature
<222> LOCATION: (31)..(33)
<223> OTHER INFORMATION: a codon for an amino acid selected from the
      group consisting of L, K, R, Q, E, D, or S
<220> FEATURE:
<221> NAME/KEY: misc_feature
<222> LOCATION: (49)..(51)
<223> OTHER INFORMATION: a codon for an amino acid selected from the
      group consisting of L, K, R, Q, E, D, or S
<220> FEATURE:
<221> NAME/KEY: misc_feature
<222> LOCATION: (115)..(117)
<223> OTHER INFORMATION: a codon for an amino acid selected from the
      group consisting of F, H, Y, K, R, Q, E, D, or S
<220> FEATURE:
<221> NAME/KEY: misc_feature
<222> LOCATION: (178)..(180)
<223> OTHER INFORMATION: a codon for an amino acid selected from the
      group consisting of H, Y, K, R, Q, E, D, or S -continued

```
<220> FEATURE:
<221> NAME/KEY: misc_feature
<222> LOCATION: (193)..(195)
<223> OTHER INFORMATION: a codon for an amino acid selected from the
      group consisting of L, K, R, Q, E, D, S, P, or A
<220> FEATURE:
<221> NAME/KEY: misc_feature
<222> LOCATION: (217)..(219)
<223> OTHER INFORMATION: a codon for an amino acid selected from the
      group consisting of P, K, R, Q, E, D, or S
<220> FEATURE:
<221> NAME/KEY: misc_feature
<222> LOCATION: (262)..(264)
<223> OTHER INFORMATION: a codon for an amino acid selected from the
      group consisting of Y, K, R, Q, E, D, S or N

<400> SEQUENCE: 3
tcacagattc cagcttcgga acaagagacc nnngttagac caaagccann ncttttgaag      60
ttattaaagt ctgttggtgc acaaaaagac acttatacta tgaagaggt tcttnnntat      120 cttggccagt atattatgac taaacgatta tatgatgaga agcaacaaca tattgtannn     180
tgttcaaatg atnnnctagg agatttgttt ggcgtgnnna gcttctctgt gaaagagcac     240
aggaaaatat ataccatgat cnnnaggaac ttggtagtag tcaatcagca ggaatcatcg     300
gactcaggta catctgtgag tgagaac                                         327

<210> SEQ ID NO 4
<211> LENGTH: 109
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: X can be L, K, R, Q, E, D, or S
<220> FEATURE:
<221> NAME/KEY: MISC_FEATURE
<222> LOCATION: (17)..(17)
<223> OTHER INFORMATION: X can be L, K, R, Q, E, D, or S
<220> FEATURE:
<221> NAME/KEY: MISC_FEATURE
<222> LOCATION: (39)..(39)
<223> OTHER INFORMATION: X can be F, H, Y, K, R, Q, E, D, or S
<220> FEATURE:
<221> NAME/KEY: MISC_FEATURE
<222> LOCATION: (60)..(60)
<223> OTHER INFORMATION: X can be H, Y, K, R, Q, E, D, or S
<220> FEATURE:
<221> NAME/KEY: MISC_FEATURE
<222> LOCATION: (65)..(65)
<223> OTHER INFORMATION: X can be L, K, R, Q, E, D, S, P, or A
<220> FEATURE:
<221> NAME/KEY: MISC_FEATURE
<222> LOCATION: (73)..(73)
<223> OTHER INFORMATION: X can be P, K, R, Q, E, D, or S
<220> FEATURE:
<221> NAME/KEY: MISC_FEATURE
<222> LOCATION: (88)..(88)
<223> OTHER INFORMATION: X can be Y, K, R, Q, E, D, S or N

<400> SEQUENCE: 4

Ser Gln Ile Pro Ala Ser Glu Gln Glu Thr Xaa Val Arg Pro Lys Pro
1               5                   10                  15

Xaa Leu Leu Lys Leu Leu Lys Ser Val Gly Ala Gln Lys Asp Thr Tyr
            20                  25                  30

Thr Met Lys Glu Val Leu Xaa Tyr Leu Gly Gln Tyr Ile Met Thr Lys
        35                  40                  45

Arg Leu Tyr Asp Glu Lys Gln Gln His Ile Val Xaa Cys Ser Asn Asp
    50                  55                  60

Xaa Leu Gly Asp Leu Phe Gly Val Xaa Ser Phe Ser Val Lys Glu His
65                  70                  75                  80
```

```
Arg Lys Ile Tyr Thr Met Ile Xaa Arg Asn Leu Val Val Val Asn Gln
            85                  90                  95

Gln Glu Ser Ser Asp Ser Gly Thr Ser Val Ser Glu Asn
        100                 105
```

<210> SEQ ID NO 5
<211> LENGTH: 327
<212> TYPE: DNA
<213> ORGANISM: Homo sapiens

<400> SEQUENCE: 5

```
tcacagattc cagcttcgga acaagagacc ctggttagac caaagccatt gcttttgaag    60
ttattaaagt ctgttggtgc acaaaaagac acttatacta tgaaagaggt tctttttat   120
cttggccagt atattatgac taaacgatta tatgatgaga agcaacaaca tattgtacat   180
tgttcaaatg atcttctagg agatttgttt ggcgtgccaa gcttctctgt gaaagagcac   240
aggaaaatat ataccatgat ctacaggaac ttggtagtag tcaatcagca ggaatcatcg   300
gactcaggta catctgtgag tgagaac                                       327
```

<210> SEQ ID NO 6
<211> LENGTH: 109
<212> TYPE: PRT
<213> ORGANISM: Homo sapiens

<400> SEQUENCE: 6

```
Ser Gln Ile Pro Ala Ser Glu Gln Glu Thr Leu Val Arg Pro Lys Pro
1               5                   10                  15

Leu Leu Leu Lys Leu Leu Lys Ser Val Gly Ala Gln Lys Asp Thr Tyr
            20                  25                  30

Thr Met Lys Glu Val Leu Phe Tyr Leu Gly Gln Tyr Ile Met Thr Lys
        35                  40                  45

Arg Leu Tyr Asp Glu Lys Gln Gln His Ile Val His Cys Ser Asn Asp
    50                  55                  60

Leu Leu Gly Asp Leu Phe Gly Val Pro Ser Phe Ser Val Lys Glu His
65                  70                  75                  80

Arg Lys Ile Tyr Thr Met Ile Tyr Arg Asn Leu Val Val Val Asn Gln
            85                  90                  95

Gln Glu Ser Ser Asp Ser Gly Thr Ser Val Ser Glu Asn
        100                 105
```

<210> SEQ ID NO 7
<211> LENGTH: 327
<212> TYPE: DNA
<213> ORGANISM: Homo sapiens

<400> SEQUENCE: 7

```
tcacagattc cagcttcgga acaagagacc ctggttagac caaagccatt gcttttgaag    60
ttattaaagt ctgttggtgc acaaaaagac acttatacta tgaaagaggt tctttattat   120
cttggccagt atattatgac taaacgatta tatgatgaga agcaacaaca tattgtatat   180
tgttcaaatg atcttctagg agatttgttt ggcgtgccaa gcttctctgt gaaagagcac   240
aggaaaatat ataccatgat ctacaggaac ttggtagtag tcaatcagca ggaatcatcg   300
gactcaggta catctgtgag tgagaac                                       327
```

<210> SEQ ID NO 8
<211> LENGTH: 109
<212> TYPE: PRT
<213> ORGANISM: Homo sapiens

```
<400> SEQUENCE: 8

Ser Gln Ile Pro Ala Ser Glu Gln Glu Thr Leu Val Arg Pro Lys Pro
1               5                   10                  15

Leu Leu Leu Lys Leu Leu Lys Ser Val Gly Ala Gln Lys Asp Thr Tyr
                20                  25                  30

Thr Met Lys Glu Val Leu Tyr Tyr Leu Gly Gln Tyr Ile Met Thr Lys
                35                  40                  45

Arg Leu Tyr Asp Glu Lys Gln Gln His Ile Val Tyr Cys Ser Asn Asp
        50                  55                  60

Leu Leu Gly Asp Leu Phe Gly Val Pro Ser Phe Ser Val Lys Glu His
65                  70                  75                  80

Arg Lys Ile Tyr Thr Met Ile Tyr Arg Asn Leu Val Val Val Asn Gln
                    85                  90                  95

Gln Glu Ser Ser Asp Ser Gly Thr Ser Val Ser Glu Asn
                100                 105

<210> SEQ ID NO 9
<211> LENGTH: 327
<212> TYPE: DNA
<213> ORGANISM: Homo sapiens

<400> SEQUENCE: 9
tcacagattc cagcttcgga acaagagacc ctggttagac caaagccatt gcttttgaag     60
ttattaaagt ctgttggtgc acaaaaagac acttatacta tgaaagaggt tctttattat    120
cttggccagt atattatgac taaacgatta tatgatgaga agcaacaaca tattgtacat    180
tgttcaaatg atcttctagg agatttgttt ggcgtgccaa gcttctctgt gaaagagcac    240
aggaaaatat ataccatgat ctacaggaac ttggtagtag tcaatcagca ggaatcatcg    300
gactcaggta catctgtgag tgagaac                                        327

<210> SEQ ID NO 10
<211> LENGTH: 109
<212> TYPE: PRT
<213> ORGANISM: Homo sapiens

<400> SEQUENCE: 10

Ser Gln Ile Pro Ala Ser Glu Gln Glu Thr Leu Val Arg Pro Lys Pro
1               5                   10                  15

Leu Leu Leu Lys Leu Leu Lys Ser Val Gly Ala Gln Lys Asp Thr Tyr
                20                  25                  30

Thr Met Lys Glu Val Leu Tyr Tyr Leu Gly Gln Tyr Ile Met Thr Lys
                35                  40                  45

Arg Leu Tyr Asp Glu Lys Gln Gln His Ile Val His Cys Ser Asn Asp
        50                  55                  60

Leu Leu Gly Asp Leu Phe Gly Val Pro Ser Phe Ser Val Lys Glu His
65                  70                  75                  80

Arg Lys Ile Tyr Thr Met Ile Tyr Arg Asn Leu Val Val Val Asn Gln
                    85                  90                  95

Gln Glu Ser Ser Asp Ser Gly Thr Ser Val Ser Glu Asn
                100                 105

<210> SEQ ID NO 11
<211> LENGTH: 327
<212> TYPE: DNA
<213> ORGANISM: Homo sapiens
```

```
<400> SEQUENCE: 11
tcacagattc cagcttcgga acaagagacc aaggttagac caaagccaaa gcttttgaag      60
ttattaaagt ctgttggtgc acaaaaagac acttatacta tgaaagaggt tcttcattat     120
cttggccagt atattatgac taaacgatta tatgatgaga agcaacaaca tattgtaaag     180
tgttcaaatg ataaactagg agatttgttt ggcgtgaaaa gcttctctgt gaaagagcac     240
aggaaaatat ataccatgat ctacaggaac ttggtagtag tcaatcagca ggaatcatcg     300
gactcaggta catctgtgag tgagaac                                         327

<210> SEQ ID NO 12
<211> LENGTH: 109
<212> TYPE: PRT
<213> ORGANISM: Homo sapiens

<400> SEQUENCE: 12

Ser Gln Ile Pro Ala Ser Glu Gln Glu Thr Lys Val Arg Pro Lys Pro
1               5                   10                  15

Lys Leu Leu Lys Leu Leu Lys Ser Val Gly Ala Gln Lys Asp Thr Tyr
            20                  25                  30

Thr Met Lys Glu Val Leu His Tyr Leu Gly Gln Tyr Ile Met Thr Lys
        35                  40                  45

Arg Leu Tyr Asp Glu Lys Gln Gln His Ile Val Lys Cys Ser Asn Asp
    50                  55                  60

Lys Leu Gly Asp Leu Phe Gly Val Lys Ser Phe Ser Val Lys Glu His
65                  70                  75                  80

Arg Lys Ile Tyr Thr Met Ile Tyr Arg Asn Leu Val Val Val Asn Gln
                85                  90                  95

Gln Glu Ser Ser Asp Ser Gly Thr Ser Val Ser Glu Asn
            100                 105

<210> SEQ ID NO 13
<211> LENGTH: 43
<212> TYPE: DNA
<213> ORGANISM: artificial sequence
<220> FEATURE:
<223> OTHER INFORMATION: primer

<400> SEQUENCE: 13
ctatgaaaga ggttctttat tatcttggcc agtatattat gac                        43

<210> SEQ ID NO 14
<211> LENGTH: 43
<212> TYPE: DNA
<213> ORGANISM: artificial sequence
<220> FEATURE:
<223> OTHER INFORMATION: primer

<400> SEQUENCE: 14
gtcataatat actggccaag ataataaaga acctctttca tag                        43

<210> SEQ ID NO 15
<211> LENGTH: 44
<212> TYPE: DNA
<213> ORGANISM: artificial sequence
<220> FEATURE:
<223> OTHER INFORMATION: primer

<400> SEQUENCE: 15
gagaagcaac aacatattgt acattgttca aatgatcttc tagg                       44
```

```
<210> SEQ ID NO 16
<211> LENGTH: 44
<212> TYPE: DNA
<213> ORGANISM: artificial sequence
<220> FEATURE:
<223> OTHER INFORMATION: primer

<400> SEQUENCE: 16
cctagaagat catttgaaca atgtacaata tgttgttgct tctc         44

<210> SEQ ID NO 17
<211> LENGTH: 29
<212> TYPE: DNA
<213> ORGANISM: artificial sequence
<220> FEATURE:
<223> OTHER INFORMATION: primer

<400> SEQUENCE: 17
caggaacttg gtagtagtca atcagcagg                           29

<210> SEQ ID NO 18
<211> LENGTH: 30
<212> TYPE: DNA
<213> ORGANISM: artificial sequence
<220> FEATURE:
<223> OTHER INFORMATION: primer

<400> SEQUENCE: 18
gactactacc aagttcctgg agatcatggt                          30
```